US010937209B2

(12) United States Patent
Lee et al.

(10) Patent No.: US 10,937,209 B2
(45) Date of Patent: Mar. 2, 2021

(54) TOMOGRAPHY IMAGING APPARATUS AND METHOD OF RECONSTRUCTING TOMOGRAPHY IMAGE

(71) Applicants: HITACHI, LTD., Tokyo (JP); KOREA ADVANCED INSTITUTE OF SCIENCE AND TECHNOLOGY, Daejeon (KR)

(72) Inventors: Duhgoon Lee, Yongin-si (KR); Jong Beom Ra, Daejeon (KR); Kyoung-yong Lee, Hwaseong-si (KR); Toshihiro Rifu, Tokyo (KR); Seungeon Kim, Incheon (KR); Seokhwan Jang, Daejeon (KR)

(73) Assignees: HITACHI, LTD., Tokyo (JP); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 76 days.

(21) Appl. No.: 15/738,741

(22) PCT Filed: Aug. 3, 2016

(86) PCT No.: PCT/KR2016/008535
§ 371 (c)(1),
(2) Date: Dec. 21, 2017

(87) PCT Pub. No.: WO2017/023105
PCT Pub. Date: Feb. 9, 2017

(65) Prior Publication Data
US 2018/0182135 A1    Jun. 28, 2018

(30) Foreign Application Priority Data
Aug. 5, 2015 (KR) .................. 10-2015-0110658

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/5264* (2013.01); *G06T 7/285* (2017.01);
(Continued)

(58) Field of Classification Search
CPC ..... G06T 7/285; G06T 11/006; G06T 11/008; G06T 2207/10076; G06T 2207/10081;
(Continued)

(56) References Cited

U.S. PATENT DOCUMENTS 6,934,357 B2   8/2005   Boyd et al.
7,630,528 B2   12/2009  Kohler et al.
(Continued)

FOREIGN PATENT DOCUMENTS

JP   2006-75590 A    3/2006
JP   2010-227171 A   10/2010
(Continued)

OTHER PUBLICATIONS

Kim et al. "Cardiac motion correction based on partial angle reconstructed images in x-ray CT." Medical physics 42.5 (Apr. 2015): 2560-2571. (Year: 2015).*
(Continued)

*Primary Examiner* — Katrina R Fujita
(74) *Attorney, Agent, or Firm* — Cooper & Dunham LLP

(57) ABSTRACT

Provided are a tomography imaging apparatus and a method of reconstructing a tomography image which may more accurately measure a motion of an object to be tomography-imaged. In detail, the tomography imaging apparatus and the method of reconstructing a tomography image may obtain
(Continued)

information indicating a motion of a moving object according to a time, may perform motion correction based on the obtained motion information, and may reconstruct a target image with reduced motion artifacts.

20 Claims, 27 Drawing Sheets

(51) Int. Cl.
*A61B 6/00* (2006.01)
*G06T 7/285* (2017.01)

(52) U.S. Cl.
CPC .......... *G06T 11/006* (2013.01); *A61B 6/4291* (2013.01); *A61B 6/5205* (2013.01); *A61B 6/56* (2013.01); *G06T 2207/10076* (2013.01); *G06T 2207/10081* (2013.01); *G06T 2207/20192* (2013.01); *G06T 2207/30048* (2013.01); *G06T 2211/412* (2013.01); *G06T 2211/421* (2013.01)

(58) Field of Classification Search
CPC . G06T 2207/20192; G06T 2207/30048; G06T 2211/412; G06T 2211/421; A61B 6/032; A61B 6/4291; A61B 6/5205; A61B 6/5264; A61B 6/56
See application file for complete search history.

(56) References Cited

U.S. PATENT DOCUMENTS

| | | | |
|---|---|---|---|
| 7,672,490 B2 | 3/2010 | Kohler et al. | |
| 7,907,764 B2 | 3/2011 | Matsuoka | |
| 8,094,772 B2 | 1/2012 | Grass et al. | |
| 8,184,883 B2 | 5/2012 | Grass et al. | |
| 8,224,056 B2 | 7/2012 | Pack et al. | |
| 8,553,962 B2 | 10/2013 | Allmendinger et al. | |
| 8,792,700 B2* | 7/2014 | Riddell | G06T 11/006 382/131 |
| 8,811,707 B2* | 8/2014 | Jackson | G06T 11/003 382/131 |
| 9,001,960 B2* | 4/2015 | Nett | G06T 5/001 378/4 |
| 9,035,941 B2 | 5/2015 | Endo et al. | |
| 9,576,391 B2 | 2/2017 | Ra et al. | |
| 9,959,631 B2* | 5/2018 | Ra | A61B 6/032 |
| 10,052,078 B2* | 8/2018 | Brendel | G06T 7/215 |
| 10,685,452 B2* | 6/2020 | Bippus | G06T 7/35 |
| 2002/0025017 A1 | 2/2002 | Stergiopoulos et al. | |
| 2004/0208276 A1* | 10/2004 | Kaufman | A61B 6/032 378/4 |
| 2008/0253636 A1* | 10/2008 | Deller | A61B 6/037 382/131 |
| 2011/0038517 A1* | 2/2011 | Mistretta | A61B 6/02 382/128 |
| 2011/0142315 A1* | 6/2011 | Hsieh | A61B 6/032 382/131 |
| 2012/0093281 A1 | 4/2012 | Zamyatin et al. | |
| 2014/0316247 A1 | 10/2014 | Hwang et al. | |
| 2015/0243045 A1 | 8/2015 | Ra et al. | |

FOREIGN PATENT DOCUMENTS

| | | |
|---|---|---|
| JP | 2010-233961 A | 10/2010 |
| KR | 10-2014-0126815 A | 11/2014 |
| KR | 10-2015-0099375 A | 8/2015 |
| KR | 10-1582093 B1 | 1/2016 |
| WO | 2013/124777 A1 | 8/2013 |
| WO | 2014006556 A1 | 1/2014 |

OTHER PUBLICATIONS

Bruder et al. "Can motion compensated reconstruction improve 'best phase' reconstruction in Cardiac CT?." Medical Imaging 2013: Physics of Medical Imaging. vol. 8668. International Society for Optics and Photonics, 2013. (Year: 2013).*
Communication dated Jul. 3, 2018, issued by the European Patent Office in counterpart European Application No. 16833341.7.
Holt, K.M., "Geometric Calibration of Third-Generation Computed Tomography Scanners From Scans of Unknown Objects Using Complementary Rays"., Sep. 1, 2007, IEEE International Conference ON, pp. IV129-IV132 (4 pages total).
Zamyatin et al., "Motion weighting in helical computed tomography with wide cone angle", Oct. 30, 2010, IEEE, pp. 2860-2863 (4 pages total).
Schretter, C., "Correction of Non-Periodic Motion in Computed Tomography", Apr. 28, 2010; (143 total pages).
Communication dated Jan. 11, 2017, issued by the Korean Intellectual property Office in counterpart Korean Patent Application No. 10-2015-0110658.
Search Report dated Nov. 10, 2016, issued by the International Searching Authority in counterpart International Patent Application No. PCT/KR2016/008535 (PCT/ISA/210 and PCT/ISA/220).
Written Opinion dated Nov. 10, 2016, issued by the International Searching Authority in counterpart International Patent Application No. PCT/KR2016/008535 (PCT/ISA/237).

* cited by examiner

[Fig. 1]
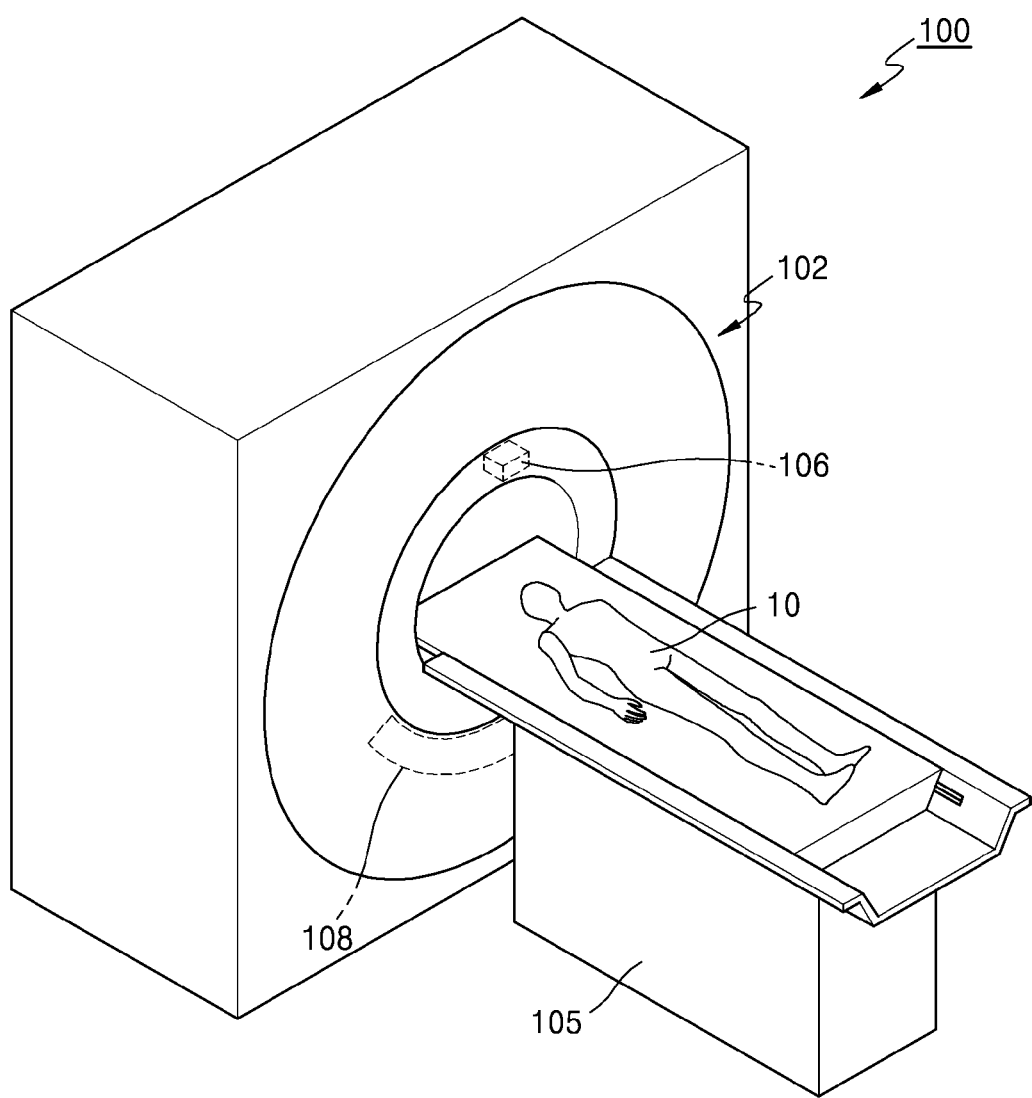

[Fig. 2]
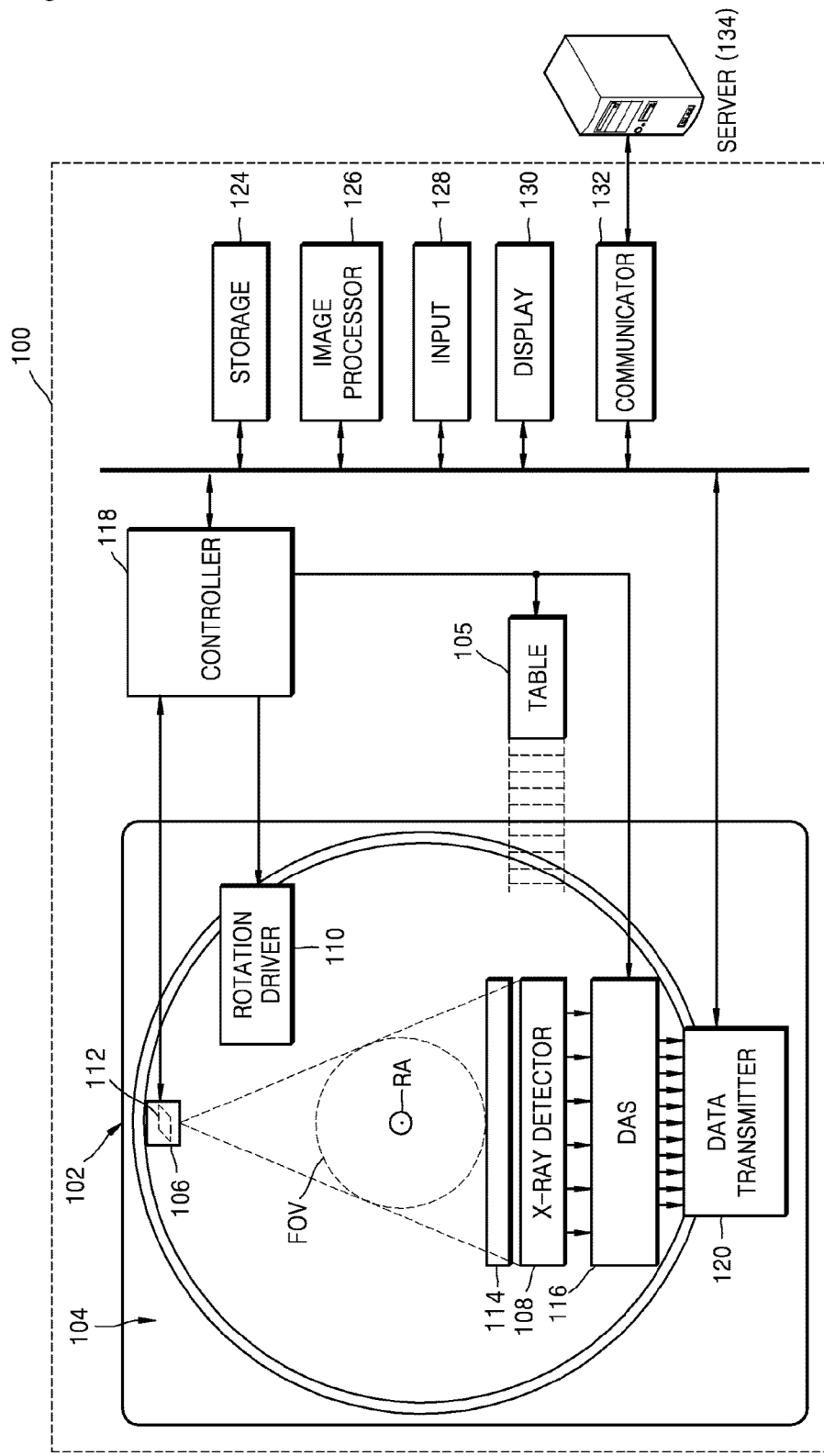

[Fig. 3]
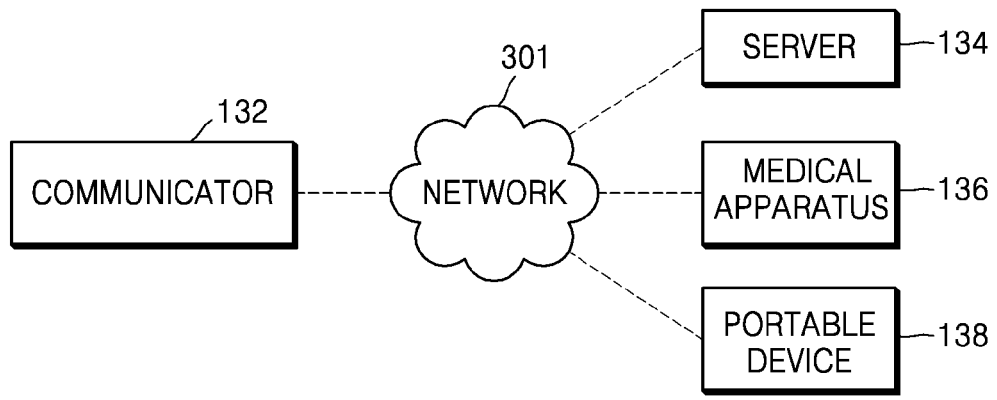
[Fig. 4]
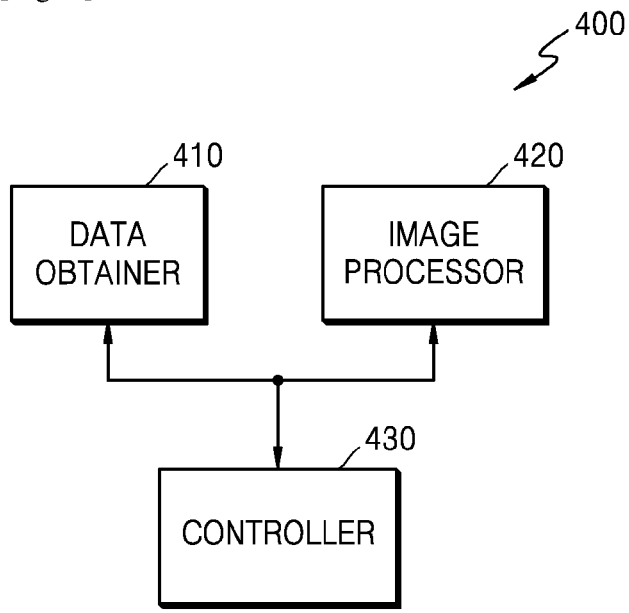
[Fig. 5]
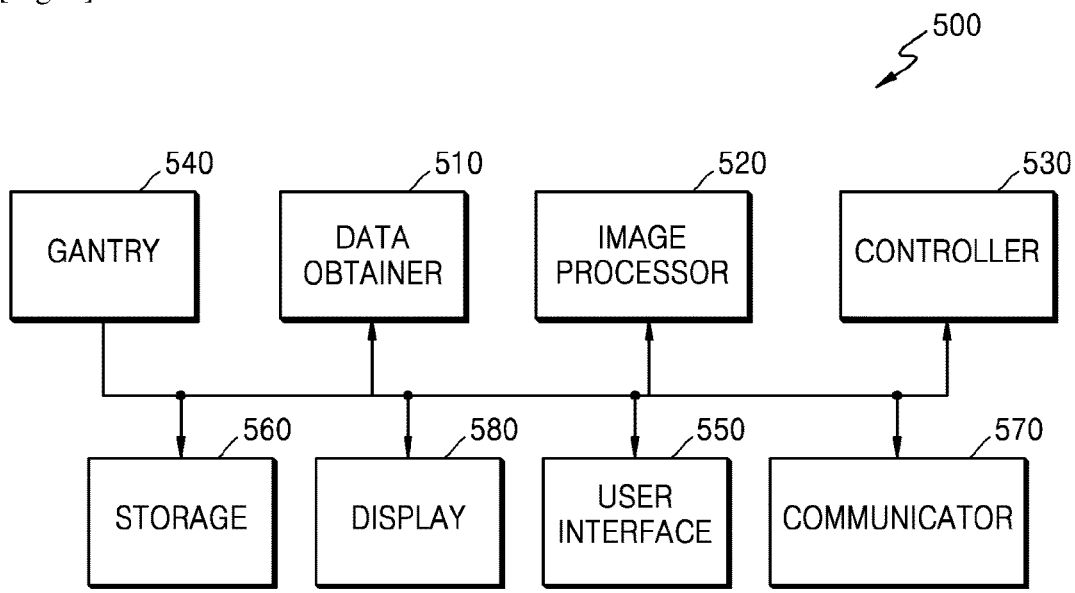

[Fig. 6]
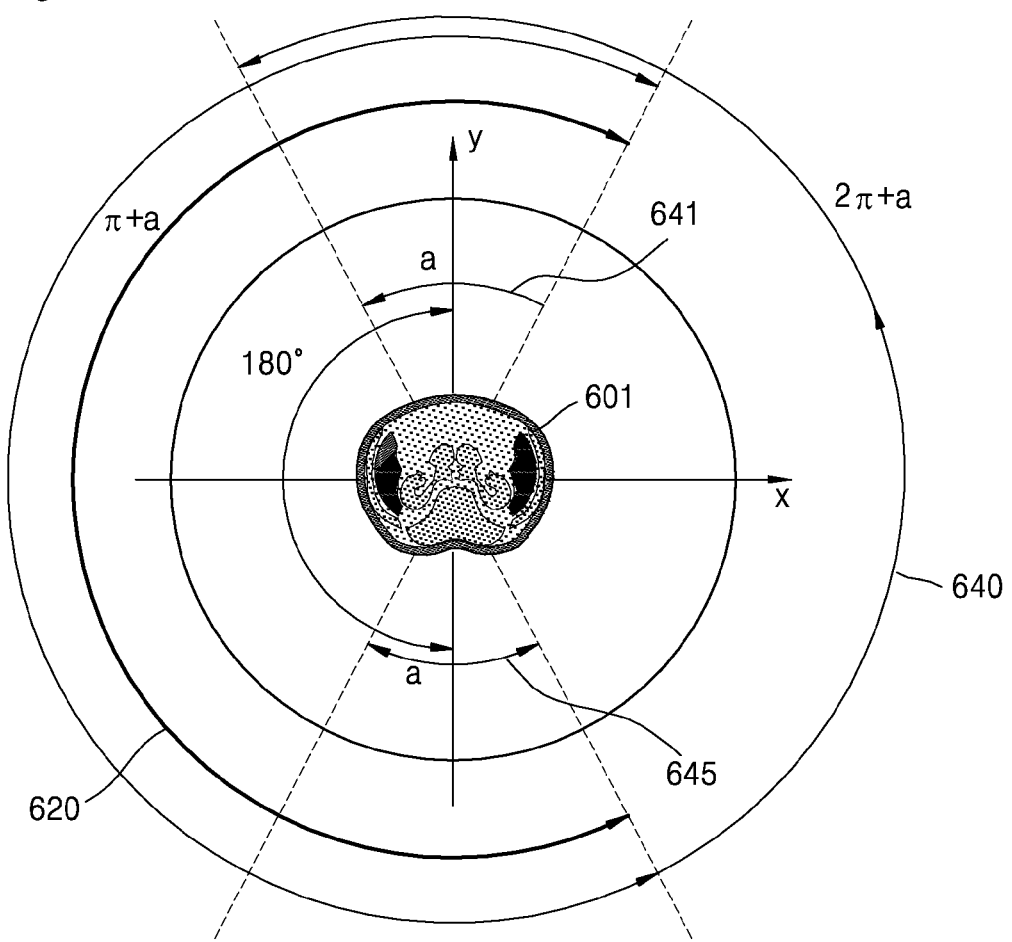

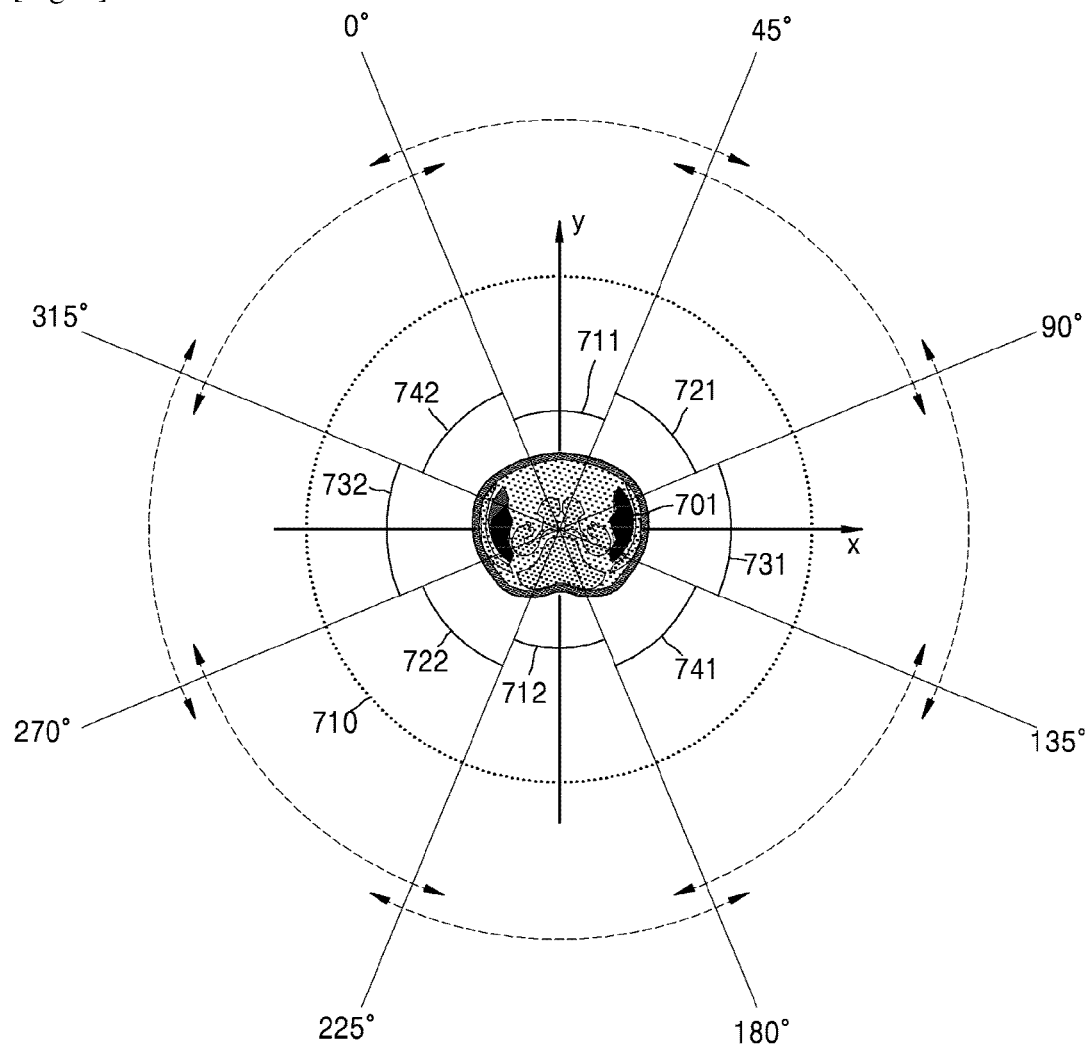
[Fig. 7]

[Fig. 8]
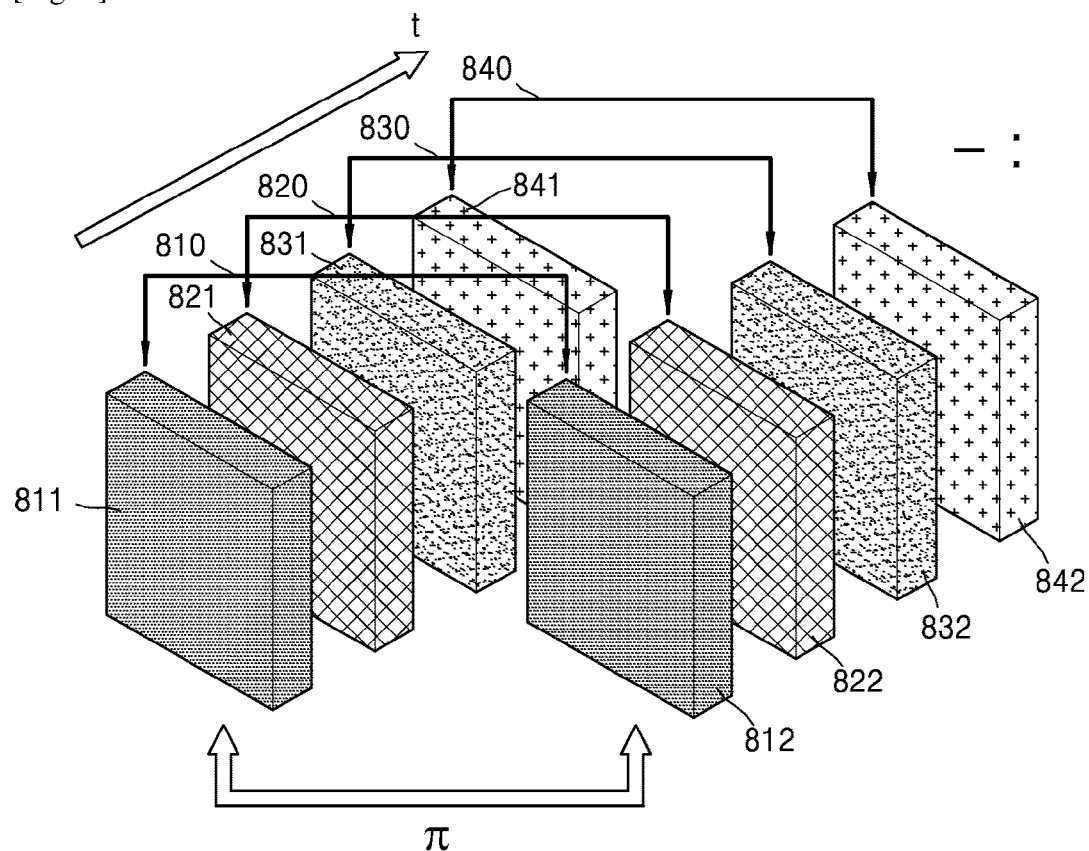
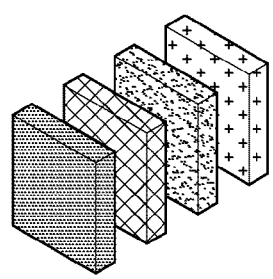 : PAR images

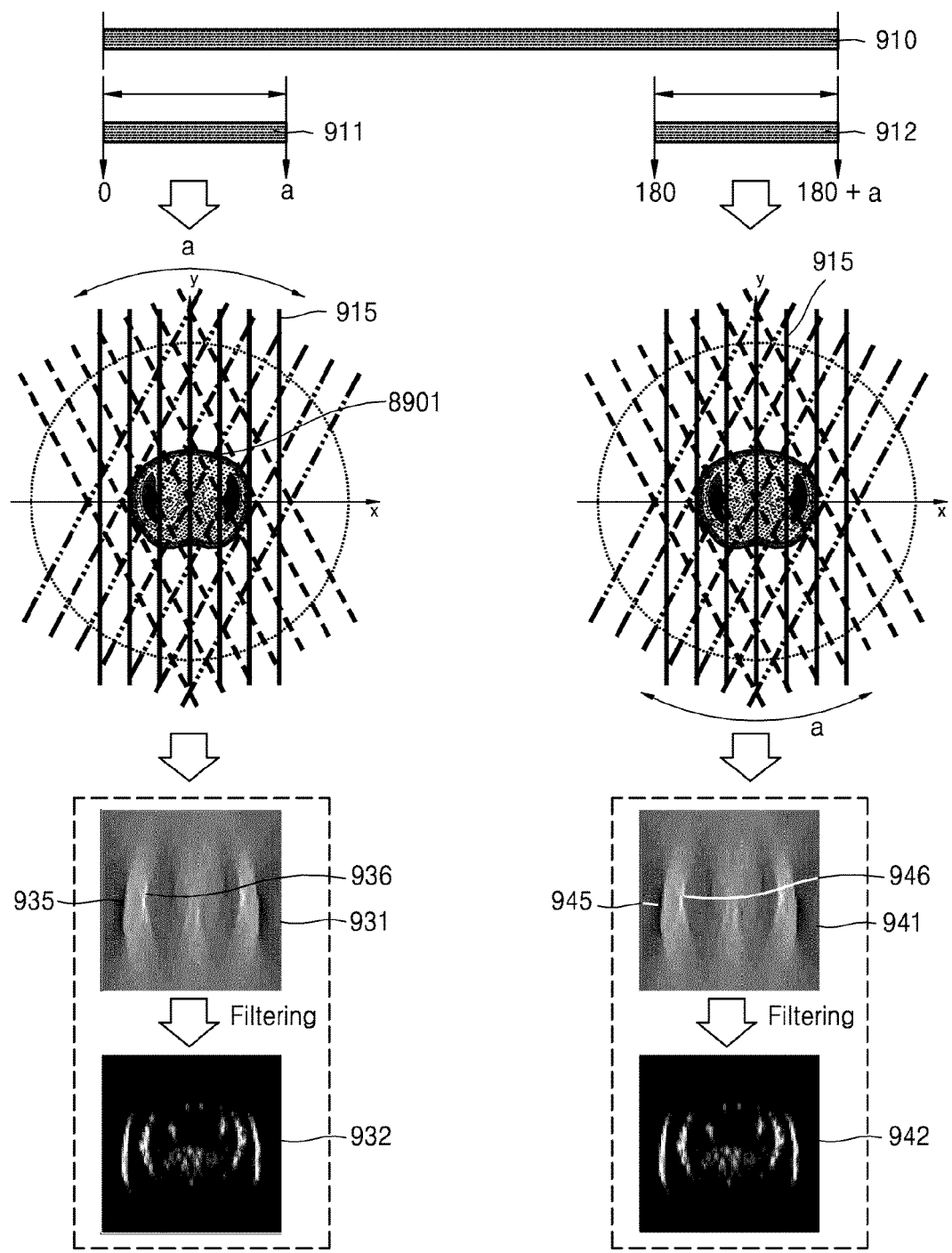

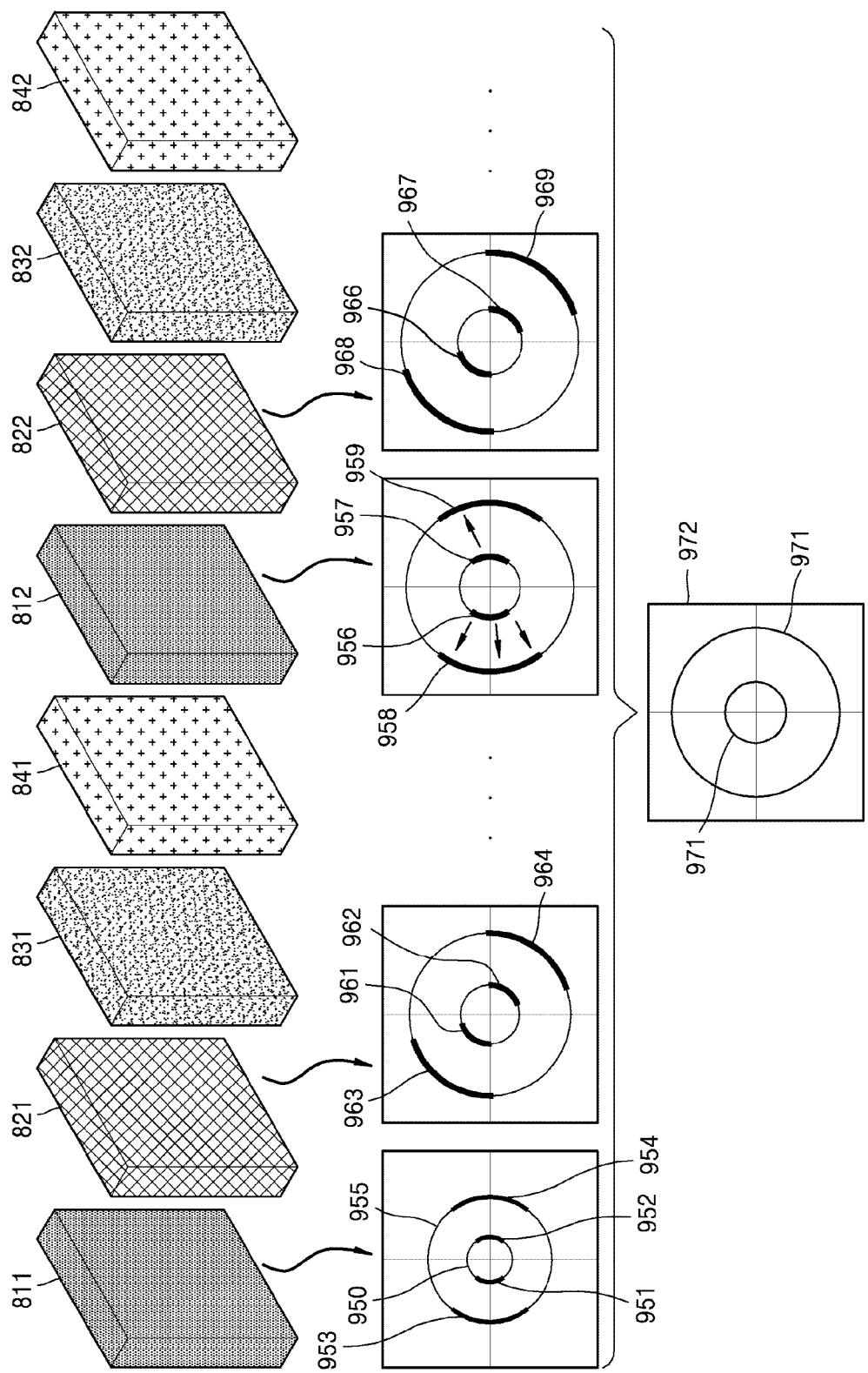
[Fig. 9B]

[Fig. 10]
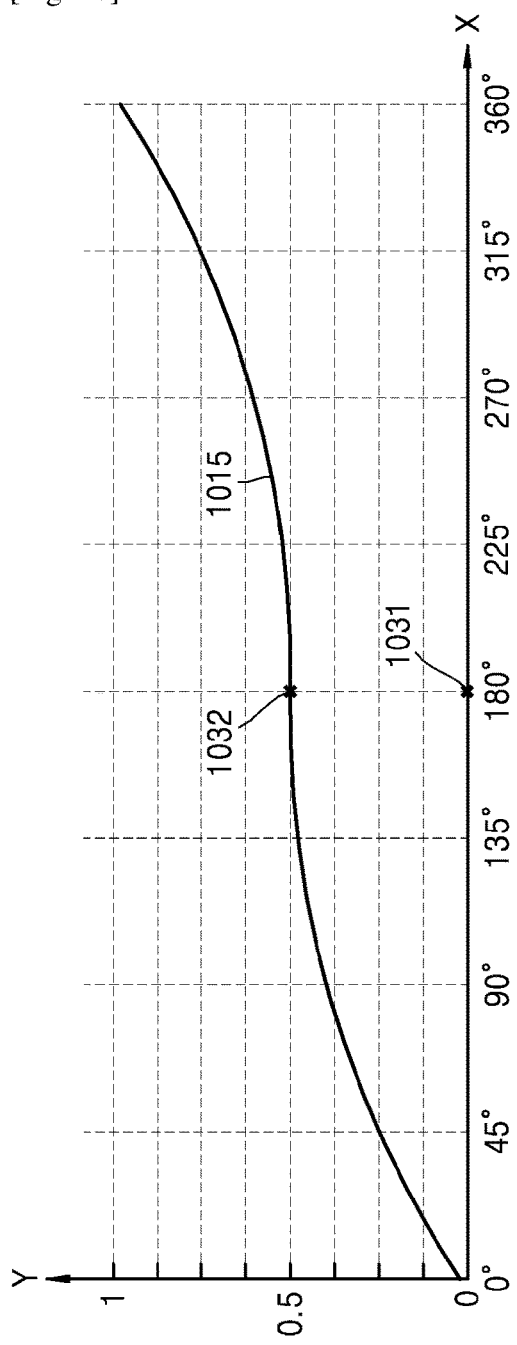
[Fig. 11A]
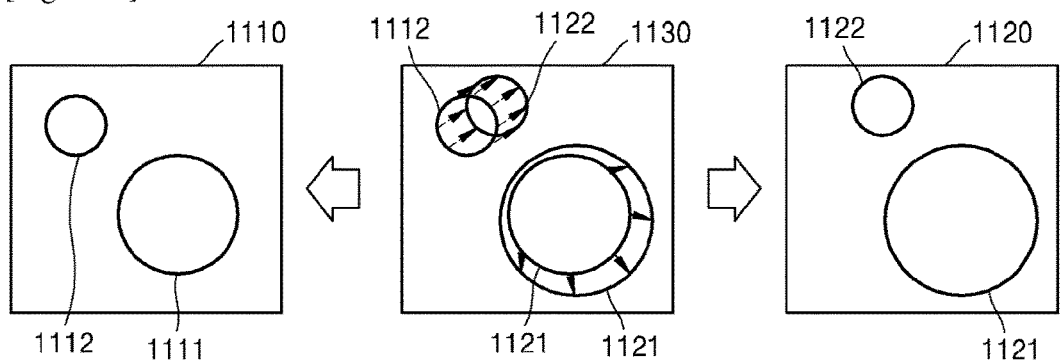

[Fig. 11B]
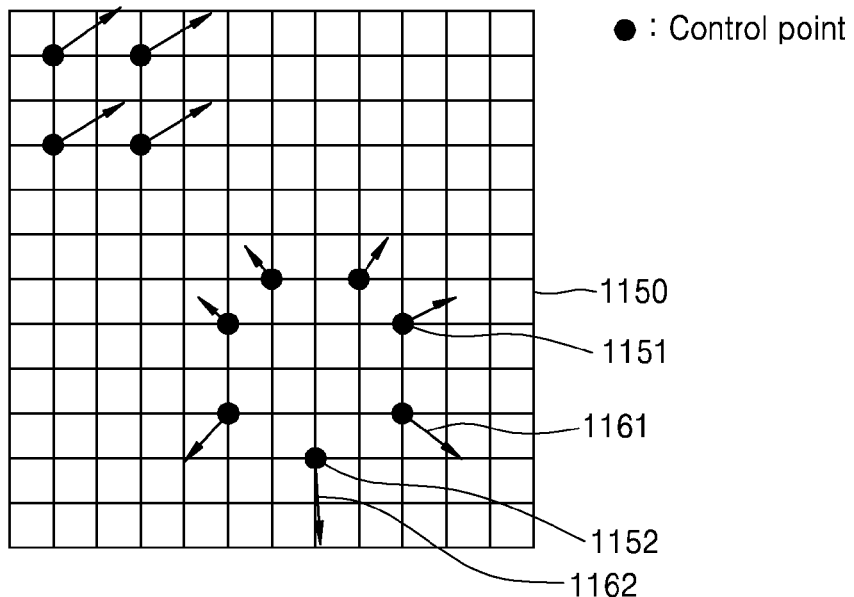
[Fig. 11C]
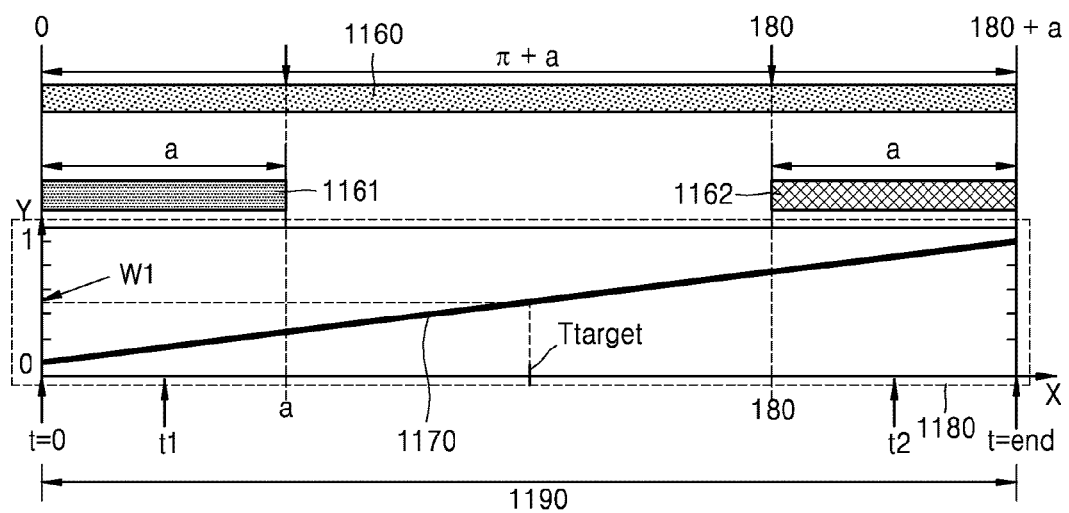

[Fig. 12]
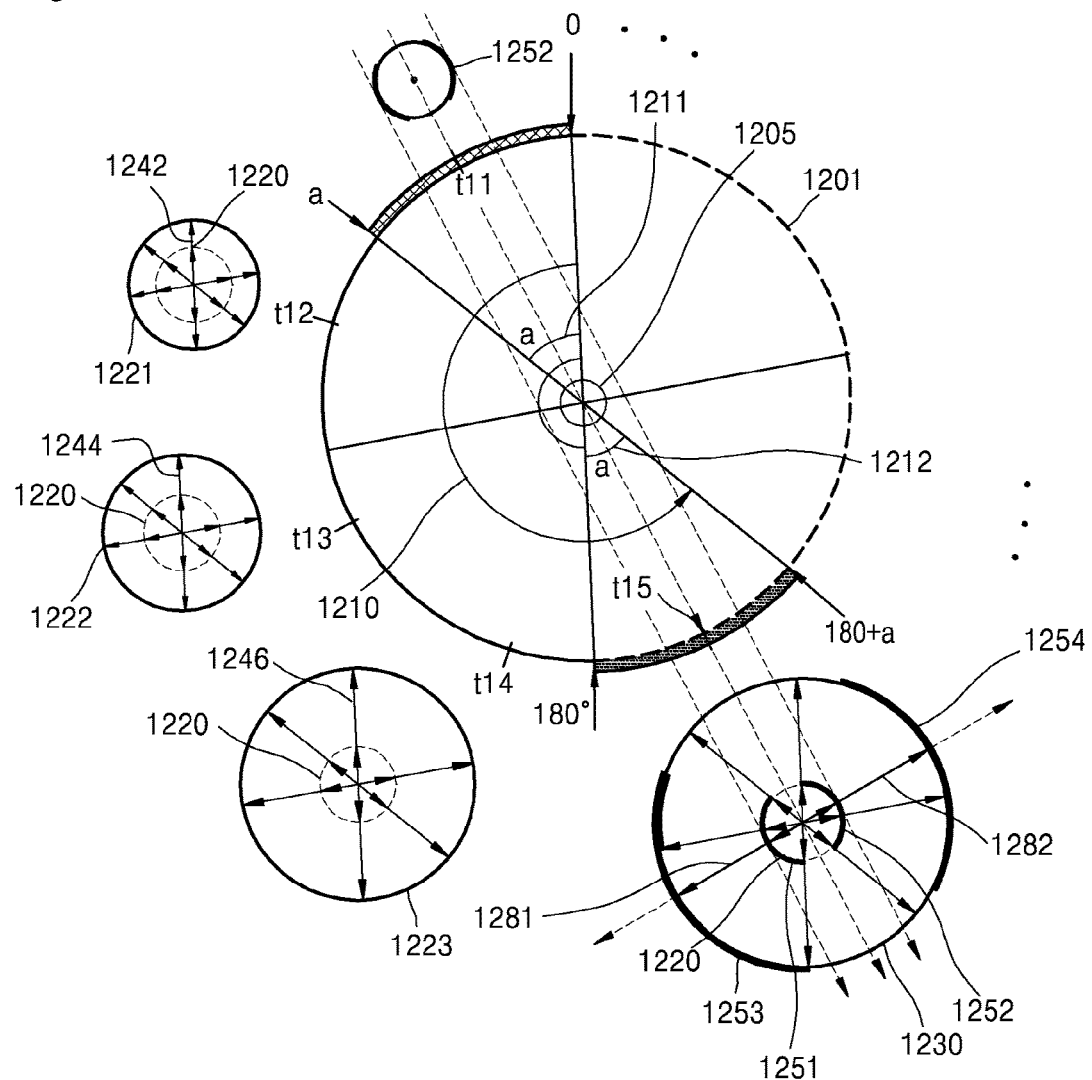

[Fig. 13]
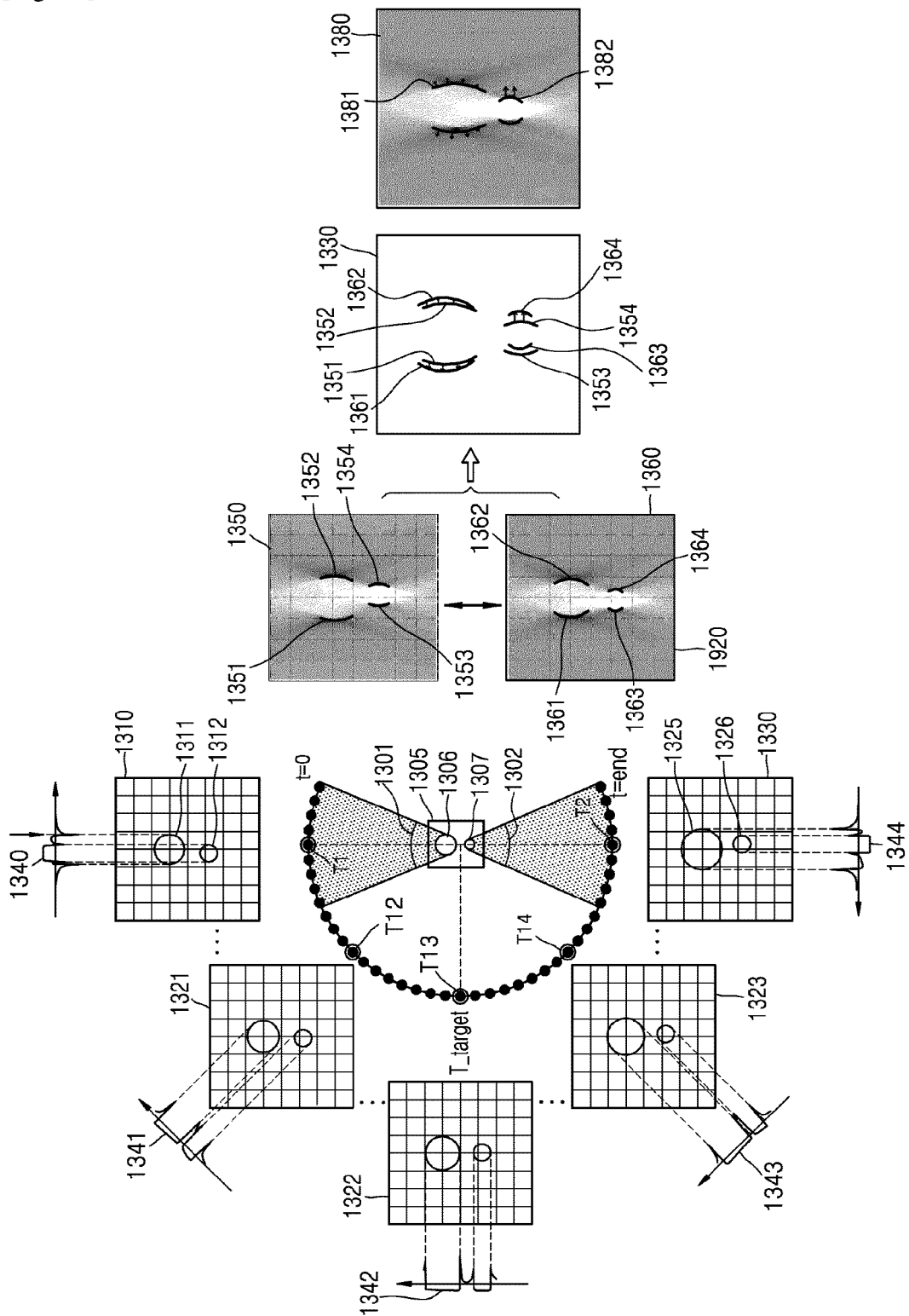

[Fig. 14]
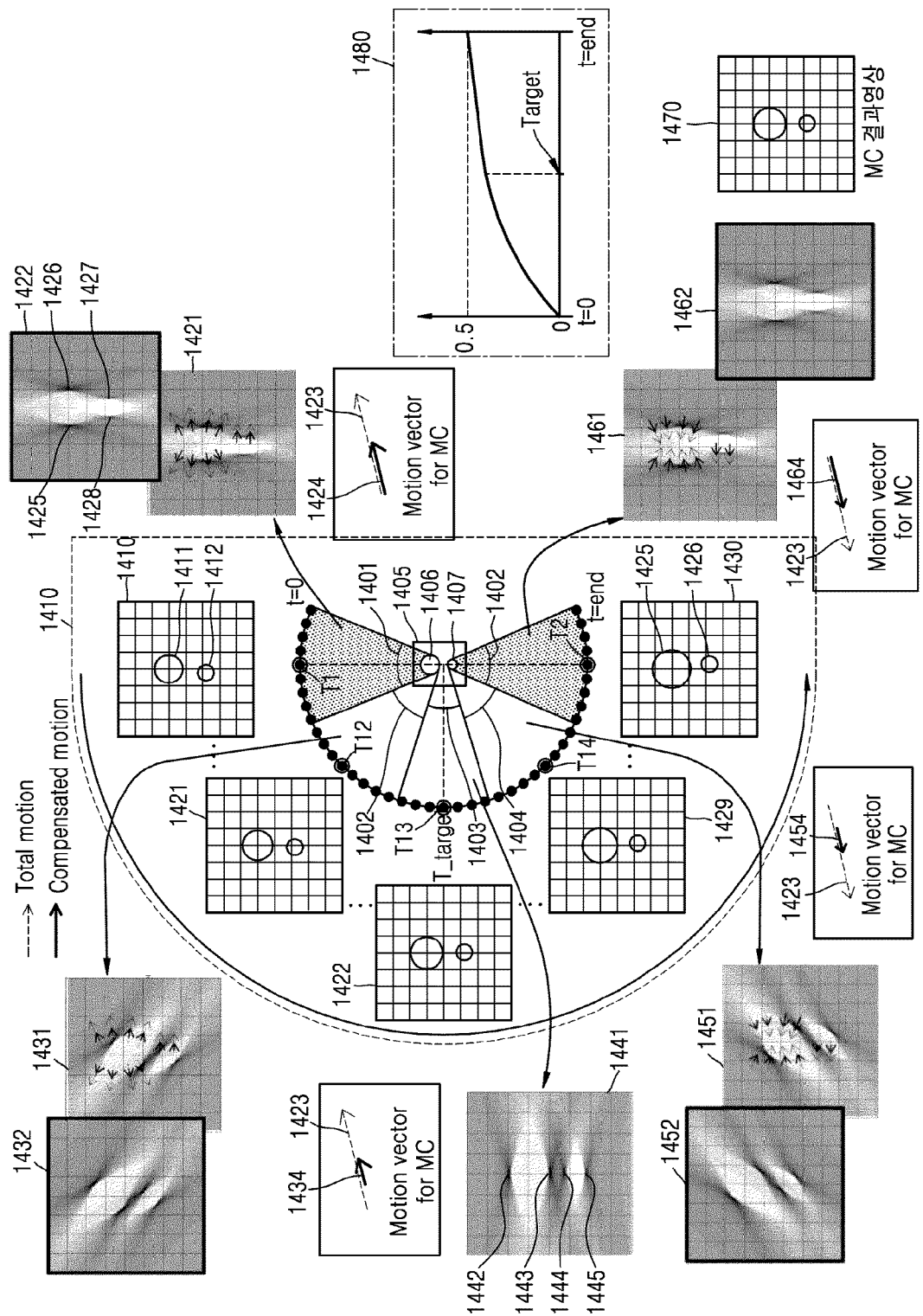

[Fig. 15]
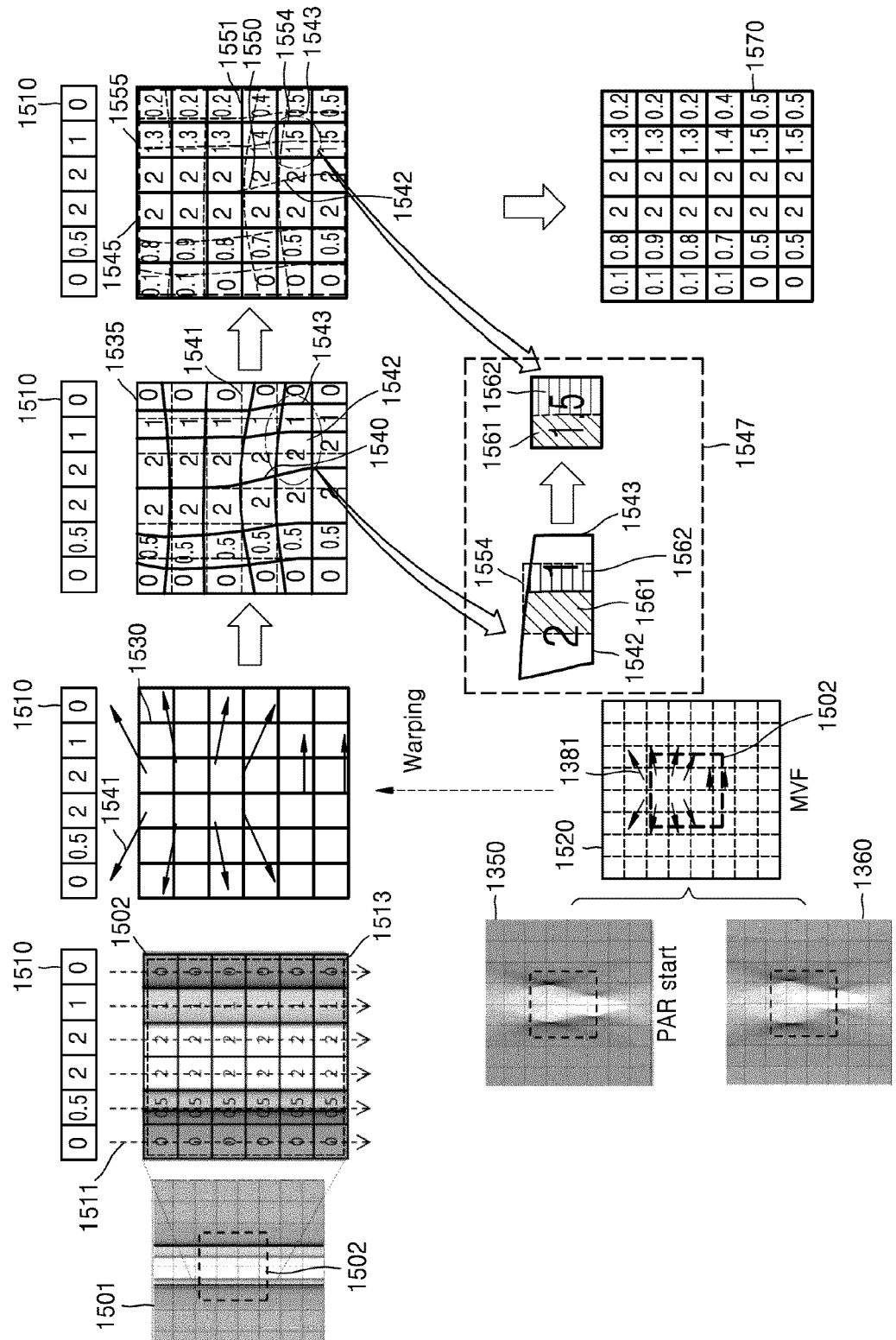

[Fig. 16]
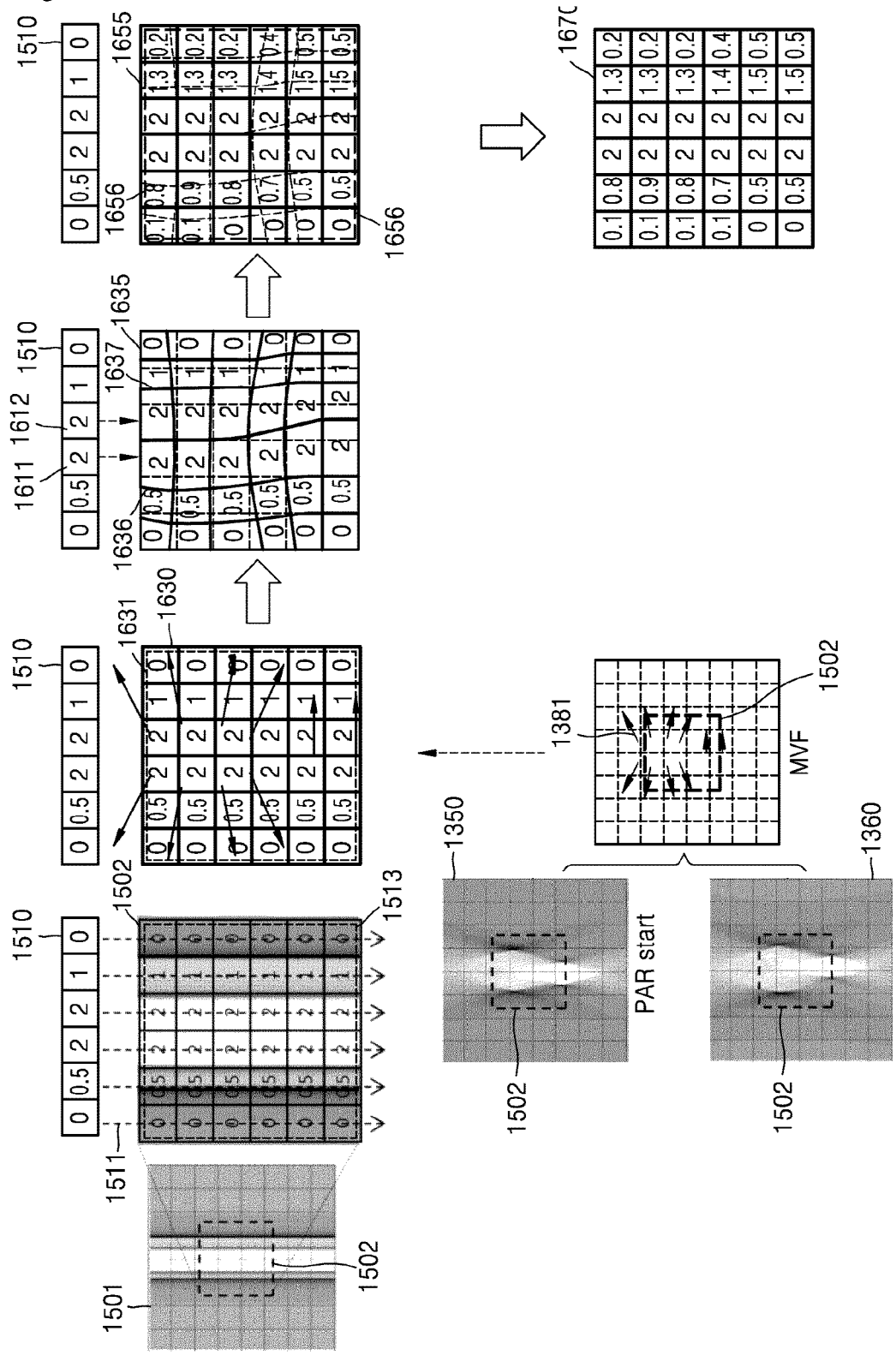

[Fig. 17]
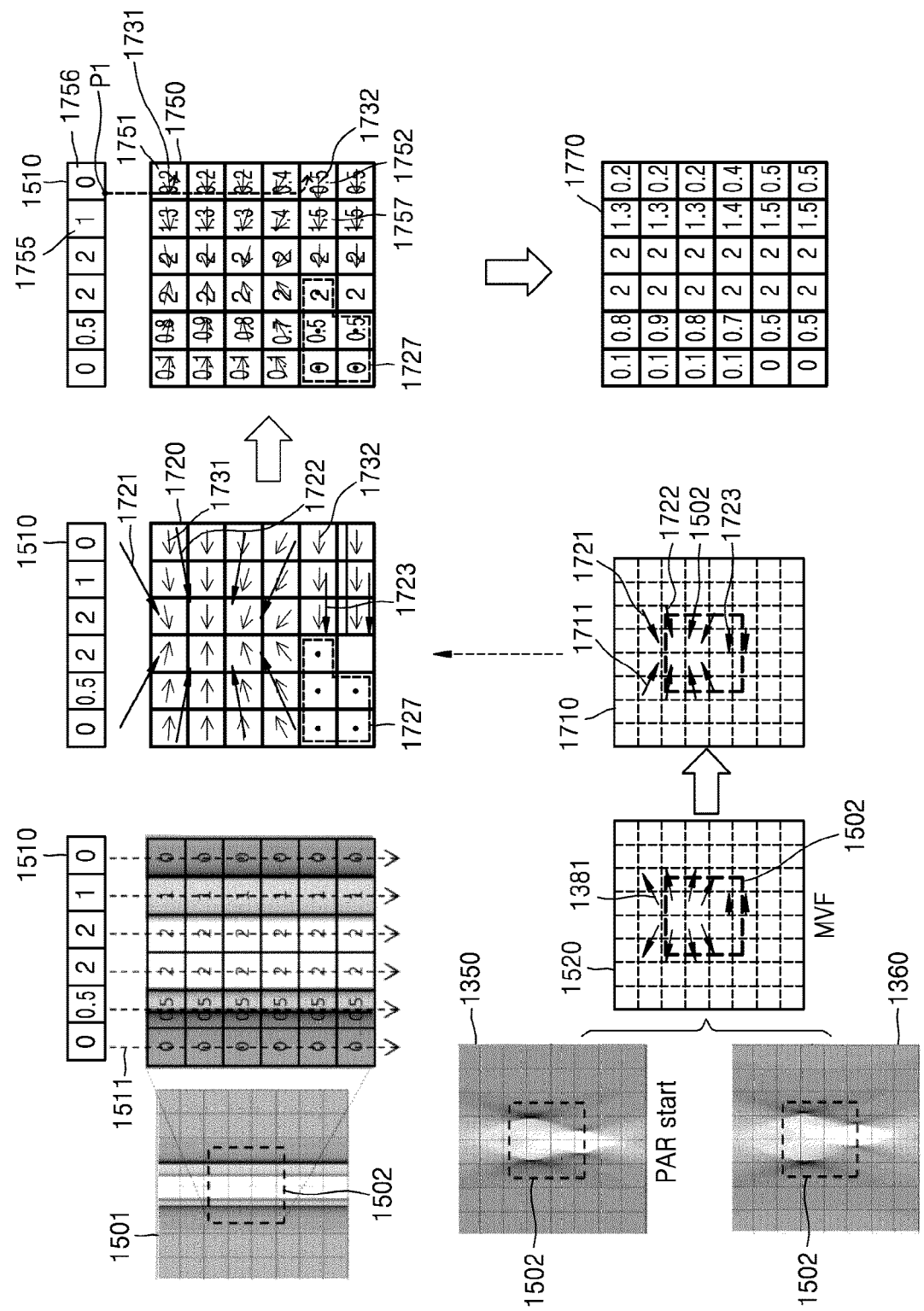

[Fig. 18A]
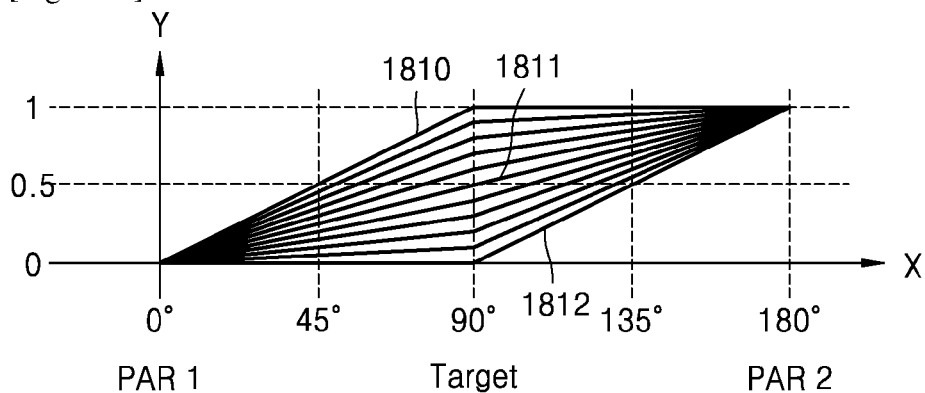
[Fig. 18B]
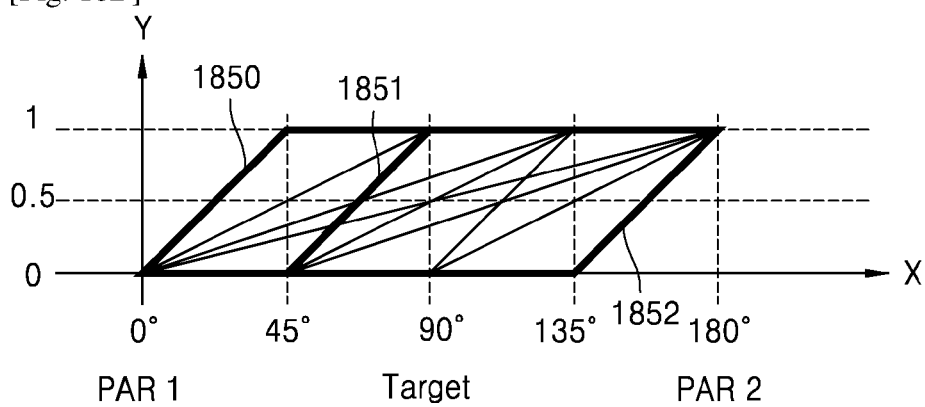
[Fig. 19]
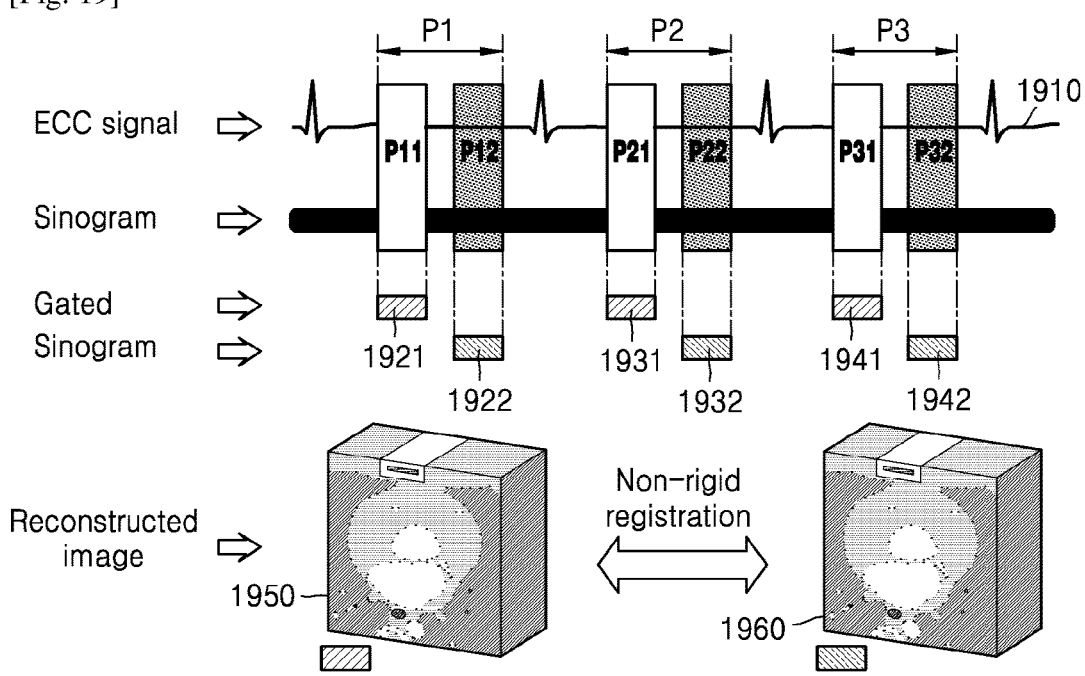

[Fig. 20A]
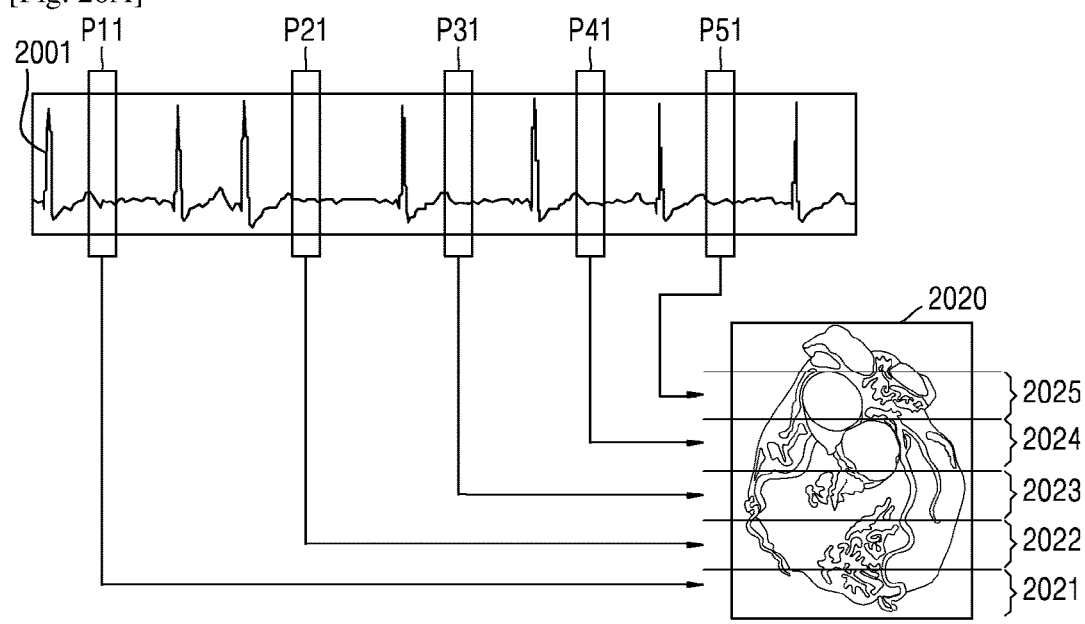
[Fig. 20B]
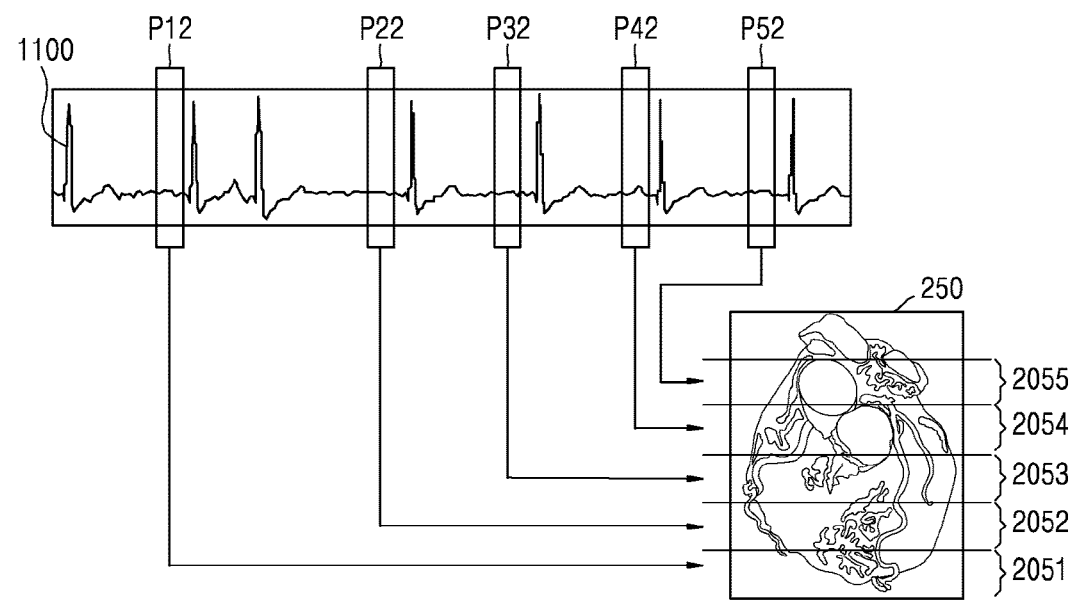

[Fig. 21]
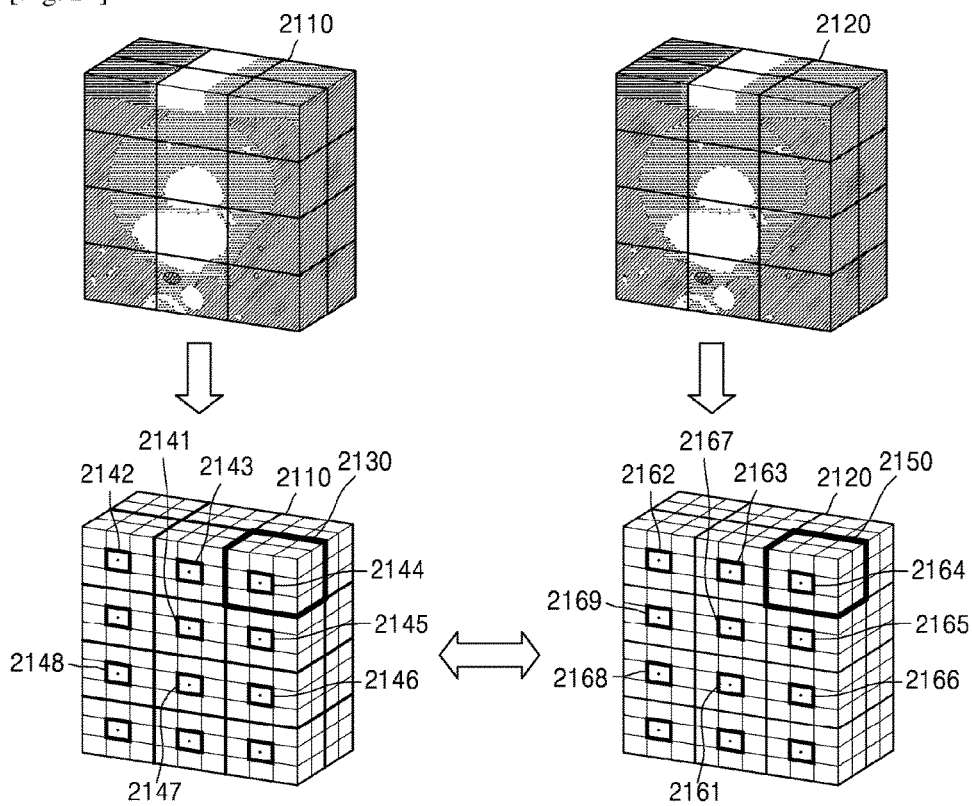
[Fig. 22A]
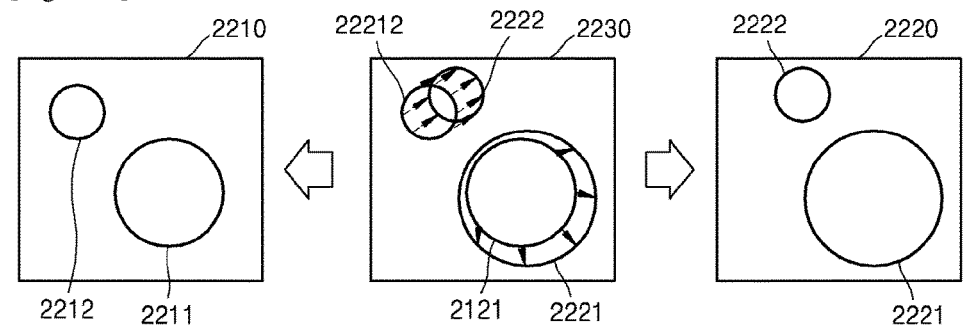
[Fig. 22B]
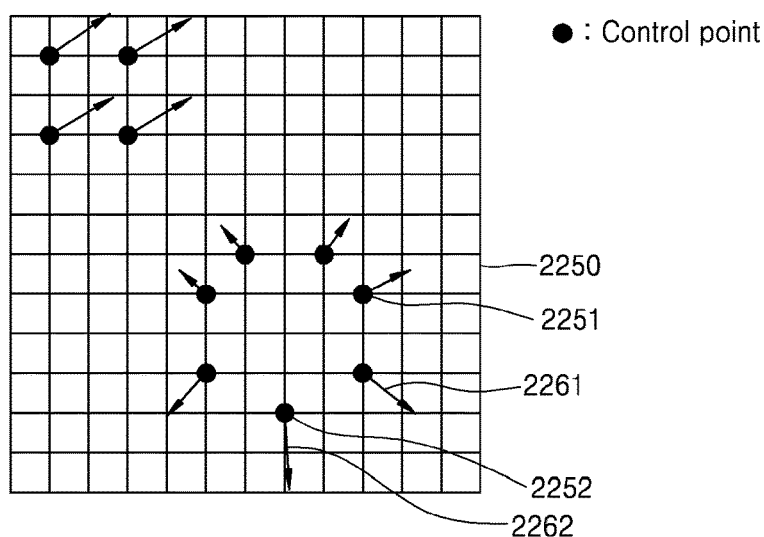

[Fig. 22C]
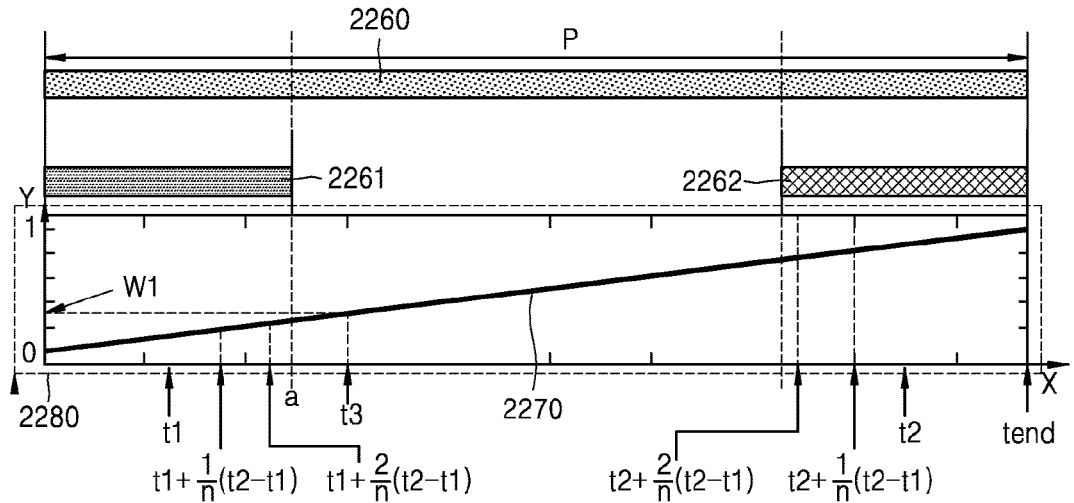
[Fig. 23A]
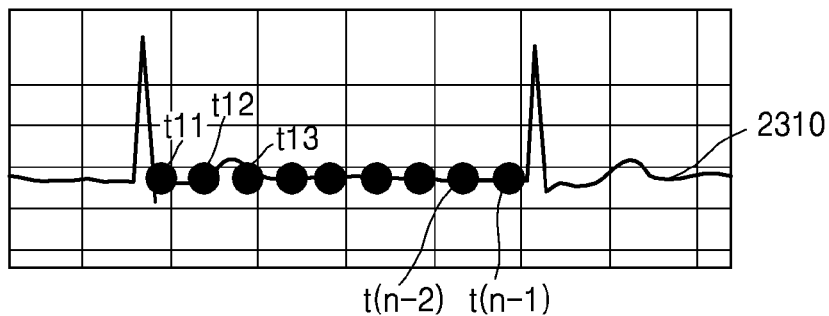
[Fig. 23B]
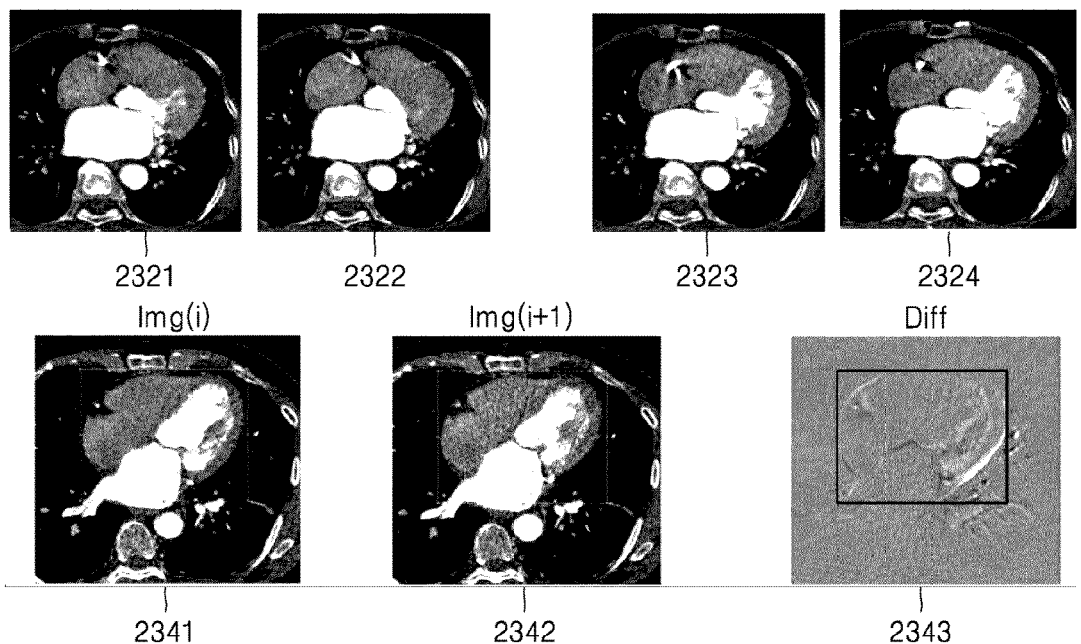

[Fig. 23C]
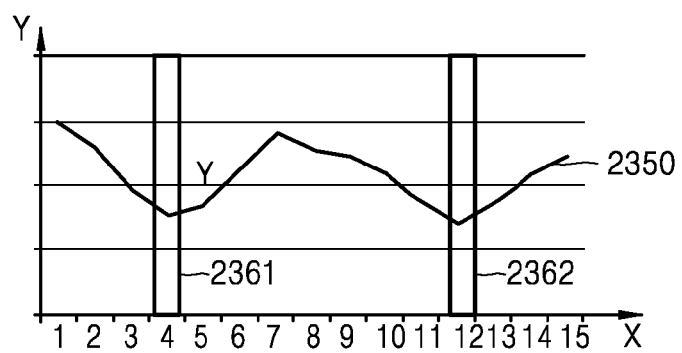

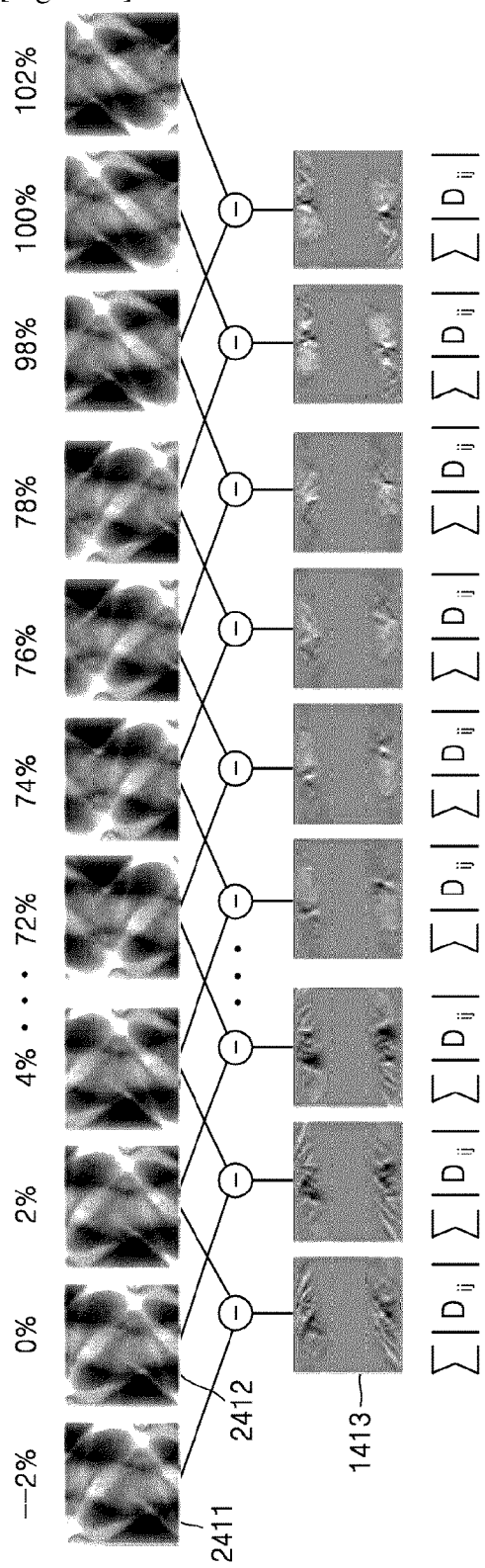
[Fig. 24A]

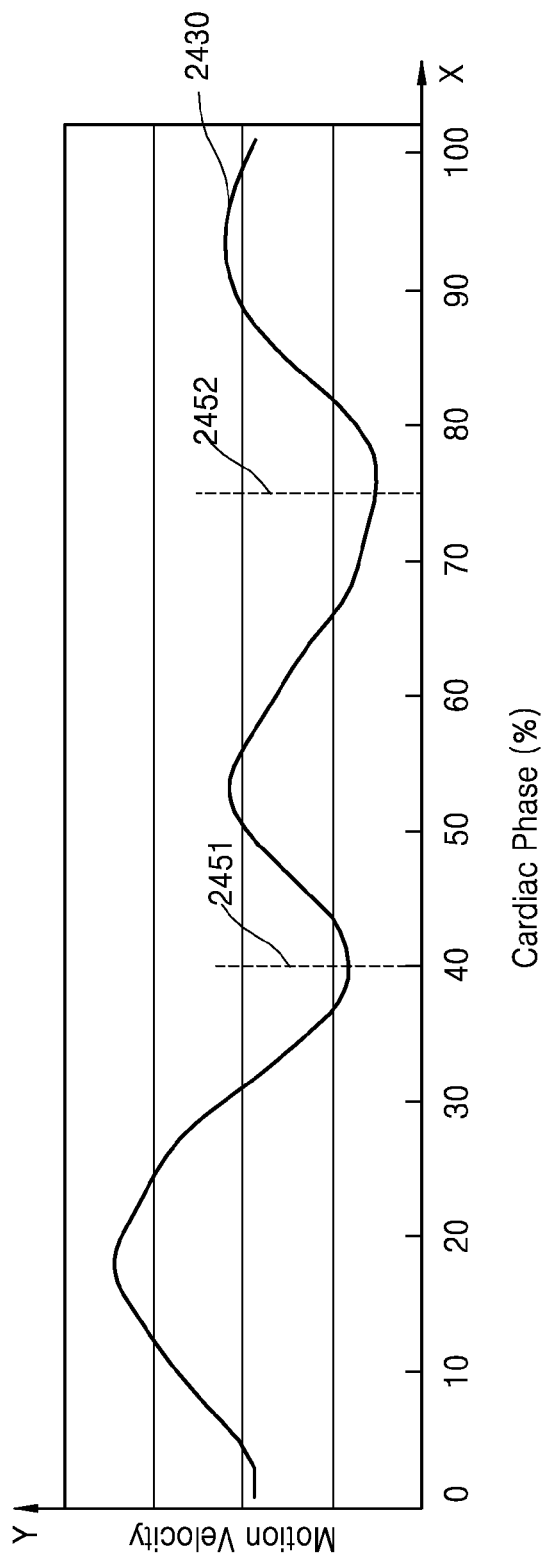
[Fig. 24B]

[Fig. 25]
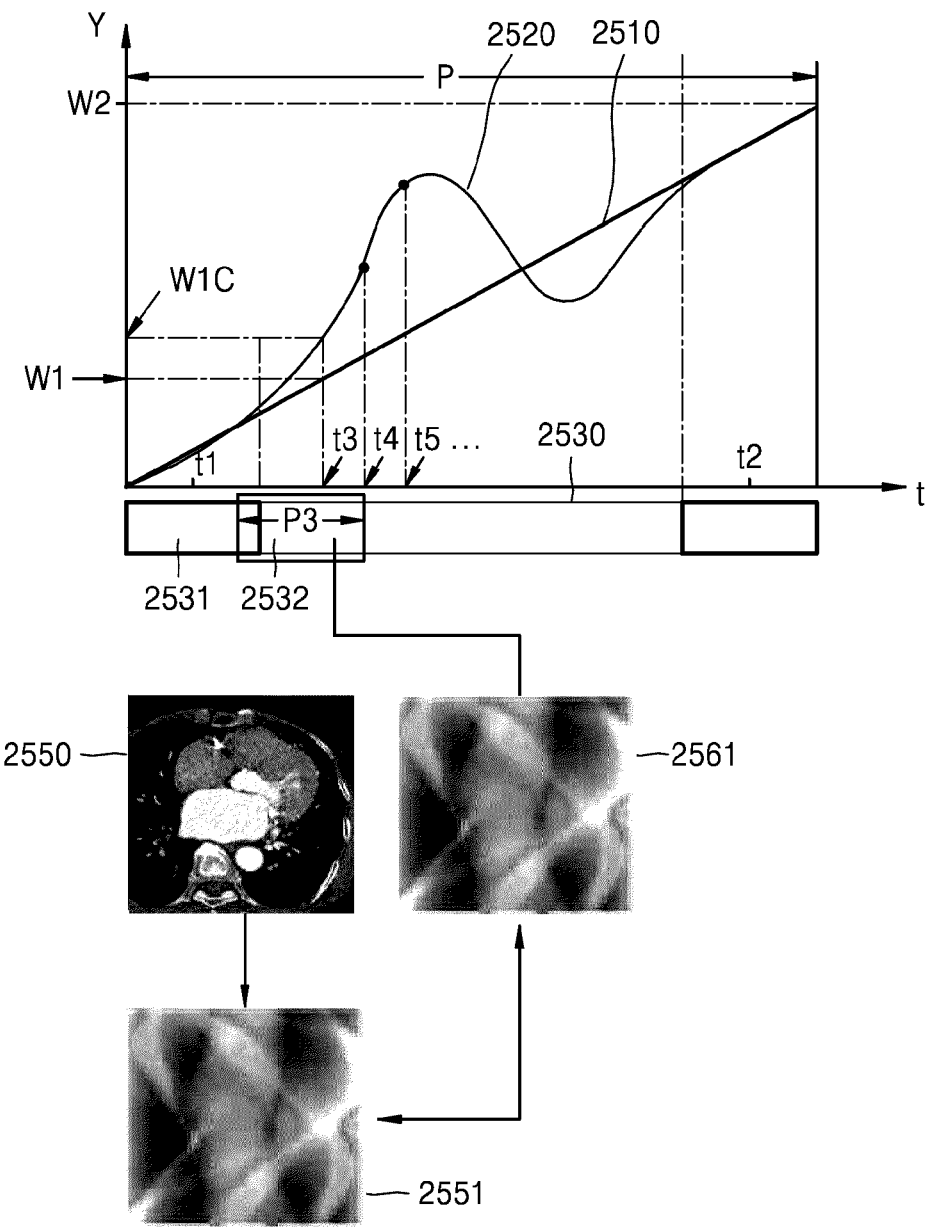

[Fig. 26]
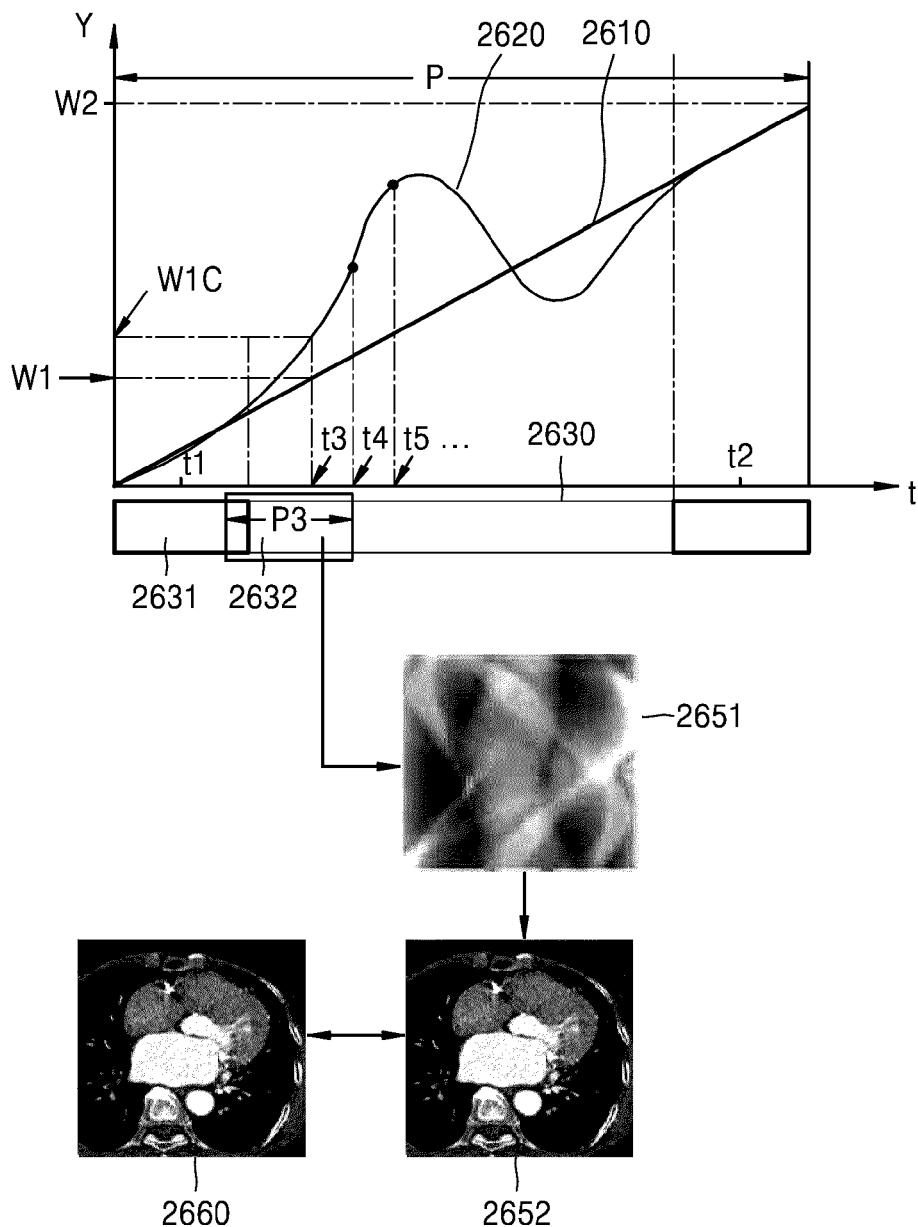

[Fig. 27]
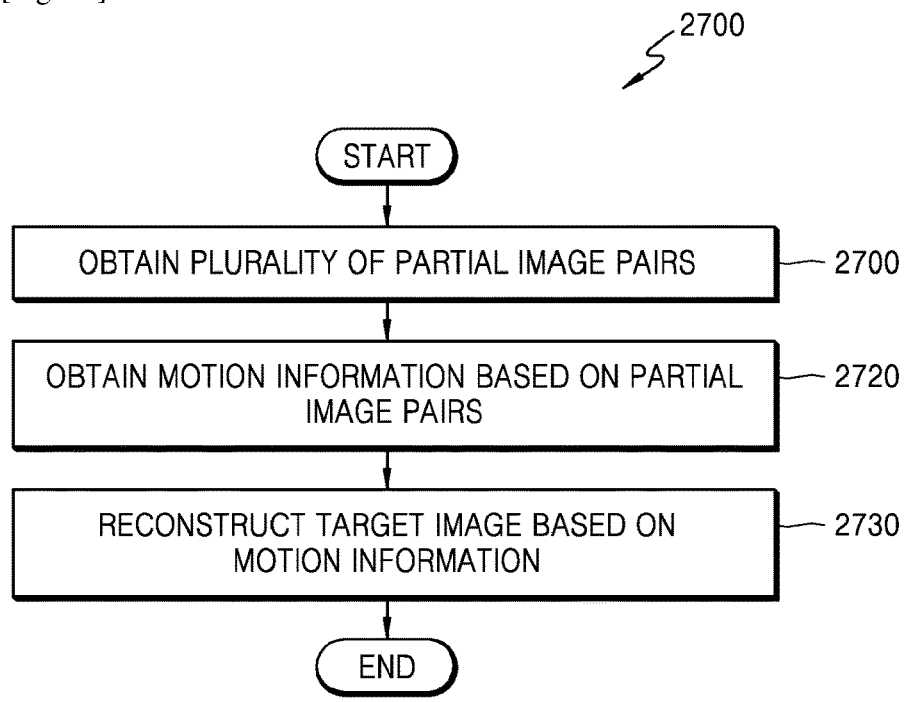
[Fig. 28]
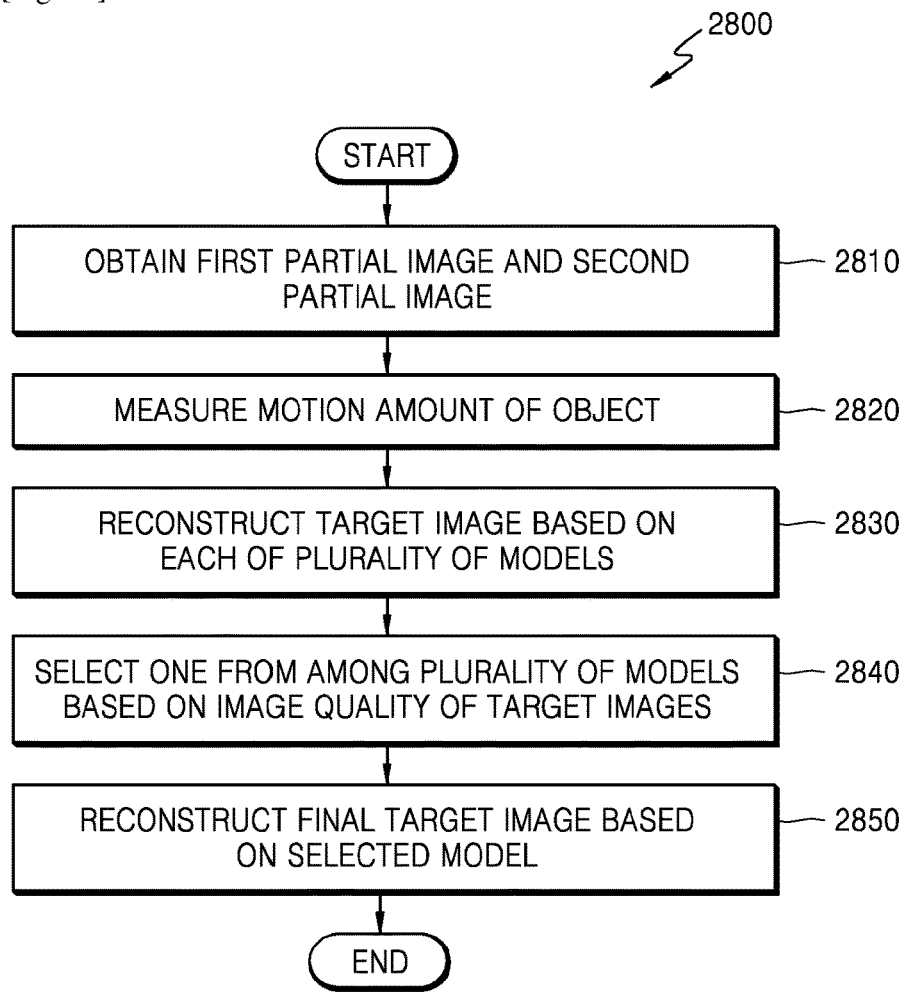

[Fig. 29]
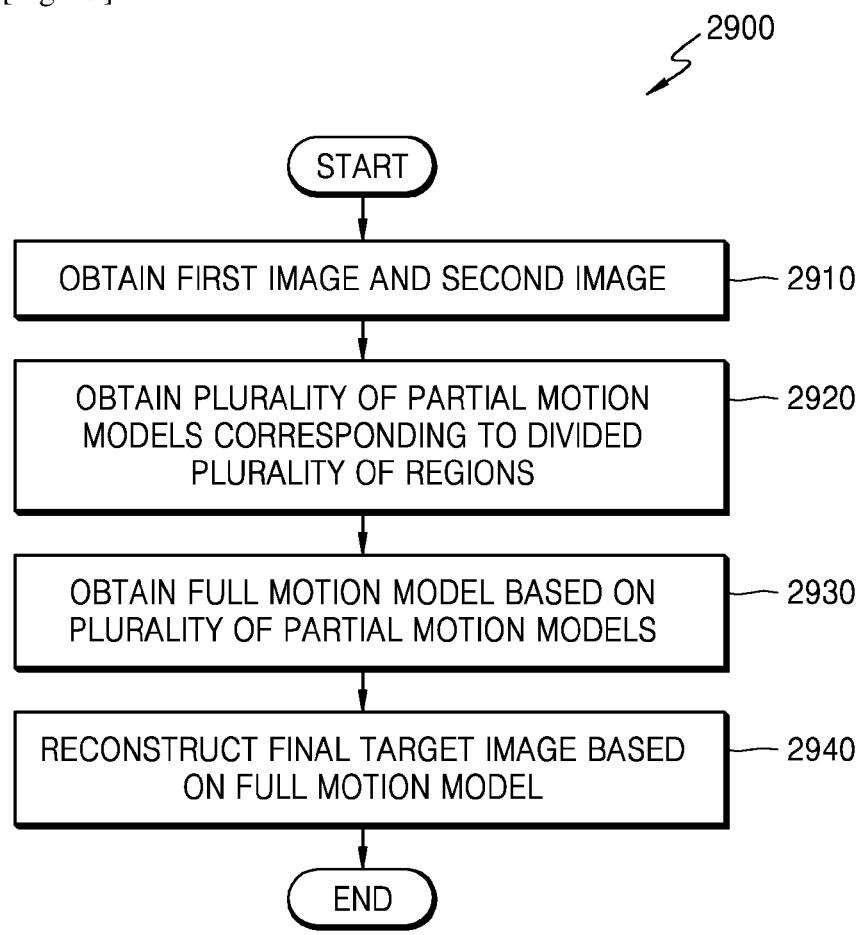

US 10,937,209 B2

TOMOGRAPHY IMAGING APPARATUS AND METHOD OF RECONSTRUCTING TOMOGRAPHY IMAGE

TECHNICAL FIELD

The present disclosure relates to tomography imaging apparatuses and methods of reconstructing tomography images, and more particularly, to tomography imaging apparatuses and methods of reconstructing tomography images by performing tomography imaging on moving objects.

BACKGROUND ART

Medical imaging apparatuses are devices for obtaining images of internal structures of objects. Medical image processing apparatuses that are non-invasive examination apparatuses obtain images of structures, internal organs, and flows of fluids in bodies and show the obtained images to users. The users, such as doctors, may examine patients' health and diagnose diseases by using medical images output from the medical image processing apparatuses.

Tomography imaging apparatuses are representative apparatuses for projecting X-rays to patients and obtaining images of the patients who are objects. In detail, examples of tomography imaging apparatuses may include computed tomography (CT) imaging apparatuses.

A CT imaging apparatus from among medical image processing apparatuses may provide a cross-sectional image of an object and may visualize internal structures (e.g., organs such as the kidney and the lung) of the object in such a manner that the internal structures do not overlap one another unlike in the case of general X-ray apparatuses, and thus is widely used to precisely diagnose a disease. Hereinafter, a medical image obtained by a tomography imaging apparatus is referred to as a tomography image. In detail, a medical image obtained by a tomography imaging apparatus is referred to as a CT image.

In order to obtain a tomography image, a tomography imaging apparatus performs tomography imaging on an object and obtains raw data. The tomography imaging apparatus reconstructs a tomography image by using the obtained raw data. The raw data may be projection data obtained by projecting X-rays to the object or a sinogram that is a set of projection data.

For example, in order to obtain a CT image, an operation of reconstructing an image by using raw data obtained by using CT imaging has to be performed.

In detail, an X-ray source included in a CT imaging apparatus performs CT imaging by rotating about an object and obtains raw data. In order to reconstruct one cross-sectional CT image, the X-ray source has to obtain raw data by making a half-rotation or a full-rotation or more. When a time taken to obtain raw data needed to reconstruct one cross-sectional CT image is one cycle time, one cycle time of a general CT imaging apparatus is equal to or greater than 0.2 seconds.

When an object to be CT-imaged moves fast, a motion of the object occurs even in one cycle time. Due to the motion of the object, motion artifacts occur when a CT image is reconstructed.

Also, a three-dimensional (3D) CT image may be reconstructed by using a plurality of cross-sectional CT images. Accordingly, more motions of an object occur while raw data needed to reconstruct a 3D CT image is obtained.

Once motion artifacts occur, an edge of an object in a reconstructed CT image may be blurred or a reconstructed image may be unclear. Accordingly, motion artifacts in a CT image reduce the quality of a CT image, thereby reducing an accuracy with which a user such as a doctor may read the CT image and diagnose a disease.

Accordingly, when a moving object is to be CT-imaged, it is important to reconstruct a CT image with reduced motion artifacts.

DISCLOSURE

Technical Solution

Provided are tomography imaging apparatuses and methods of reconstructing tomography images which may more accurately measure motions of objects.

Provided are tomography imaging apparatuses and methods of reconstructing tomography images which may effectively reduce motion artifacts in the reconstructed tomography images and may improve the quality of the reconstructed tomography images.

Advantageous Effects

As described above, a tomography imaging apparatus and a method of reconstructing a tomography image according to the one or more embodiments may increase an accuracy in measuring a motion of an object and may improve image quality of a reconstructed target image by performing motion correction.

DESCRIPTION OF DRAWINGS

These and/or other aspects will become apparent and more readily appreciated from the following description of the embodiments, taken in conjunction with the accompanying drawings in which:

FIG. 1 is a schematic view of a computer tomography (CT) system;

FIG. 2 is a block diagram illustrating a structure of the CT system;

FIG. 3 is a block diagram for explaining communication performed by a communicator;

FIG. 4 is a block diagram of a tomography imaging apparatus according to an embodiment;

FIG. 5 is a block diagram of a tomography imaging apparatus according to another embodiment;

FIG. 6 is a view for explaining a reconstruction method used for tomography imaging;

FIG. 7 is a view for explaining an operation of the tomography imaging apparatus according to an embodiment;

FIG. 8 is a view for explaining an operation performed by the tomography imaging apparatus to obtain information indicating a motion of an object according to an embodiment;

FIG. 9A is a view for explaining a partial image pair reconstructed by the tomography imaging apparatus according to another embodiment;

FIG. 9B is a view for explaining an operation performed by the tomography imaging apparatus to obtain information indicating a motion of an object according to another embodiment;

FIG. 10 is a graph for explaining an operation performed by the tomography imaging apparatus to obtain information indicating a motion of an object according to another embodiment;

FIGS. 11A through 11C are views for explaining an operation performed by the tomography imaging apparatus to obtain information indicating a motion of an object according to another embodiment;

FIG. 12 is a view of for explaining a motion of an object estimated based on information indicating a motion of the object;

FIG. 13 is a view for explaining an operation of measuring a motion of an object according to an embodiment;

FIG. 14 is a view for explaining an operation of reconstructing a target image according to another embodiment;

FIG. 15 is a view for explaining a warping operation used to reconstruct a target image according to an embodiment;

FIG. 16 is a view for explaining a warping operation used to reconstruct a target image according to another embodiment;

FIG. 17 is a view for explaining an operation of reconstructing a target image according to another embodiment;

FIGS. 18A and 18B are views illustrating a plurality of models used in the tomography imaging apparatus according to an embodiment;

FIG. 19 is a view for explaining an operation of the tomography imaging apparatus according to another embodiment;

FIGS. 20A and 20B are views for explaining an operation of obtaining a first image and a second image used to measure a motion of an object;

FIG. 21 is a view for explaining an operation of measuring a motion by using a first image and a second image according to an embodiment;

FIGS. 22A through 22C are views for explaining an operation of measuring a motion by using a first image and a second image according to another embodiment;

FIGS. 23A through 23C are views for explaining an operation of setting points of time of a first image and a second image according to an embodiment;

FIGS. 24A and 24B are views for explaining an operation of setting points of time of a first image and a second image according to another embodiment;

FIG. 25 is a view for explaining an operation of correcting a full motion model according to an embodiment;

FIG. 26 is a view for explaining an operation of correcting a full motion model according to another embodiment;

FIG. 27 is a flowchart of a method of reconstructing a tomography image according to an embodiment;

FIG. 28 is a flowchart of a method of reconstructing a tomography image according to another embodiment; and FIG. 29 is a flowchart of a method of reconstructing a tomography image according to another embodiment.

BEST MODE

Additional aspects will be set forth in part in the description which follows and, in part, will be apparent from the description, or may be learned by practice of the presented embodiments.

According to an aspect of an embodiment, a tomography imaging apparatus includes: a data obtainer configured to obtain data by performing tomography imaging on a moving object; an image processor configured to divide the data into a plurality of data pairs corresponding to a plurality of facing partial angle pairs and to reconstruct a partial image pair by using each of the plurality of data pairs; and a controller configured to obtain motion information indicating a motion of the object in a full section including the plurality of facing partial angle pairs based on a plurality of the partial image pairs corresponding to the plurality of data pairs and to control a target image indicating the object at a target point of time to be reconstructed based on the motion information.

Each of the plurality of facing partial angle pairs may include a first angle section having a value less than 180° and a second angle section facing the first angle section.

Each of the plurality of partial image pairs may include a first partial image reconstructed by using data obtained in the first angle section and a second partial image reconstructed by using data obtained in the second angle section.

The controller may obtain the motion information indicating a motion of a surface of the object in the full section based on the plurality of partial image pairs.

The controller may obtain the motion information indicating a motion of the object according to a time so that each of partial images included in the plurality of partial image pairs has a shape at a first point of time included in the full section.

The image processor may reconstruct a three-dimensional (3D) partial image pair indicating the object in a 3D space.

The motion information may be information indicating a motion of the object in the 3D space and a four-dimensional (4D) space including a time point.

The controller may estimate a motion amount of the object at the target point of time based on the motion information and control the target image to be reconstructed based on the estimated motion amount.

The controller may reconstruct the target image by warping a plurality of images according to views indicating parts of the object based on the motion information.

The full section may have a value equal to or greater than 360°.

According to an aspect of another embodiment, a method of reconstructing a tomography image includes: dividing data obtained by performing tomography imaging on a moving object into a plurality of data pairs corresponding to a plurality of facing partial angle pairs and reconstructing a partial image pair by using each of the plurality of data pairs; obtaining motion information indicating a motion of the object in a full section including the plurality of facing partial angle pairs based on a plurality of the partial image pairs corresponding to the plurality of data pairs; and reconstructing a target image indicating the object at a target point of time based on the motion information.

According to an aspect of another embodiment, a tomography imaging apparatus includes: a data obtainer configured to obtain a first partial image and a second partial image respectively corresponding to a first point of time and a second point of time by using pieces of data obtained in a first angle section and a second angle section that face each other by performing tomography imaging on a moving object; an image processor configured to measure a motion amount of the object between the first point of time and the second point of time by using the first partial image and the second partial image and to reconstruct a target image indicating the object at a target point of time between the first point of time and the second point of time based on each of a plurality of models indicating a motion of the object between the first point of time and the second point of time set based on the motion amount; and a controller configured to measure image quality of a plurality of the target images respectively based on the plurality of models, to select one from among the plurality of models based on the measured image quality, and to control a final target image indicating the object at the target point of time to be reconstructed based on the selected model.

At least one of the plurality of models may include a model indicating a motion shape of the object that moves at a non-constant velocity between the first point of time and the second point of time.

The plurality of models may have a same motion amount between the first point of time and the second point of time and different motion shapes of the object for a time between the first point of time and the second point of time.

The first partial image may be a partial image reconstructed by using data obtained in the first angle section that has a value less than 180° and the first partial image may indicate the object at the first point of time, and the second partial image may be a partial image reconstructed by using data obtained in a second angle section that has a value less than 180° and faces the first angle section and the second partial image may indicate the object at the second point of time.

The controller may measure image quality of the plurality of target images that are motion-corrected respectively based on the plurality of models, select a model corresponding to a first target image with highest image quality from among the plurality of target images, and control the final target image that is motion-corrected to be reconstructed based on the selected model.

The image quality may be measured by using an image quality metric for measuring at least one value from among an image blur amount and an image resolution.

According to an aspect of another embodiment, a method of reconstructing a tomography image includes: obtaining a first partial image and a second partial image respectively corresponding to a first point of time and a second point of time by using pieces of data obtained in a first angle section and a second angle section that face each other by performing tomography imaging on a moving object; measuring a motion amount of the object between the first point of time and the second point of time by using the first partial image and the second partial image; reconstructing a target image indicating the object at a target point of time between the first point of time and the second point of time based on each of a plurality of models indicating a motion of the object between the first point of time and the second point of time set based on the motion amount; measuring image quality of a plurality of the target images respectively reconstructed based on the plurality of models and selecting one from among the plurality of models based on the measured image quality; and reconstructing a final target image indicating the object at the target point of time based on the selected model.

According to an aspect of another embodiment, a tomography imaging apparatus includes: a data obtainer configured to obtain a first image corresponding to a first point of time and a second image corresponding to a second point of time by performing tomography imaging on a moving object; a controller configured to divide each of the first image and the second image into a plurality of regions, to obtain a partial motion model corresponding to each of the plurality of regions and indicating a motion of the object between the first point of time and the second point of time, and to obtain a full motion model indicating a motion of the object in a full region including the plurality of regions based on a plurality of the partial motion models respectively corresponding to the plurality of regions; and an image processor configured to reconstruct a target image indicating the object at a target point of time between the first point of time and the second point of time based on the full motion model.

The controller may obtain the full motion model indicating a motion of each of a plurality of voxels included in the full region for the first point of time and the second point of time by interpolating at least two from among the plurality of partial motion models.

The full motion model may include information indicating a space-variant motion of each of the plurality of voxels included in the full region.

The controller may estimate a target image corresponding to the target point of time based on the full motion model, compare the estimated target image with the target image reconstructed by using data obtained by using the tomography imaging, and correct the full motion model based on a result of the comparison.

The data obtainer may select two points of time in a time section during which a motion of the object is smallest as the first point of time and the second point of time.

According to an aspect of another embodiment, a method of reconstructing a tomography image includes: obtaining a first image corresponding to a first point of time and a second image corresponding to a second point of time by performing tomography imaging on a moving object; dividing each of the first image and the second image into a plurality of regions, and obtaining a partial motion model corresponding to each of the plurality of regions and indicating a motion of the object between the first point of time and the second point of time by using the first image and second image; obtaining a full motion model indicating a motion of the object in a full region including the plurality of regions based on a plurality of the partial motion models respectively corresponding to the plurality of regions; and reconstructing a target image indicating the object at a target point of time between the first point of time and the second point of time based on the full motion model.

MODE FOR INVENTION

Advantages and features of one or more embodiments and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept according to an embodiments to one of ordinary skill in the art, and the inventive concept will only be defined by the appended claims. Like reference numerals refer to like elements throughout the specification.

Hereinafter, the terms used in the specification will be briefly defined, and the embodiments will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

As used herein, the term "and/or" includes any and all combinations of one or more of the associated listed items.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medical image expert, or a technician who repairs a medical apparatus.

Since a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an embodiment will now be described with reference to FIGS. 1 and 2. The CT system 100 may include various types of devices.

FIG. 1 is a schematic view of the CT system 100. Referring to FIG. 1, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

FIG. 2 is a block diagram illustrating a structure of the CT system 100.

The CT system 100 may include the gantry 102, the table 105, a controller 118, a storage 124, an image processor 126, an input 128, a display 130, and a communicator 132.

As described above, the object 10 may be positioned on the table 105. In the present embodiment, the table 105 may move in a predetermined direction (e.g., at least one of up, down, right, and left directions), and movement of the table 105 may be controlled by the controller 118.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, a solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation velocity. The rotating frame 104 may receive the driving signal and power from the rotation driver 110 while the rotating frame 104 contacts the rotation driver 110 via a slip ring (not shown). Also, the rotating frame 104 may receive the driving signal and power from the rotation driver 110 via wireless communication.

The X-ray generator 106 may receive a voltage and current from a power distribution unit (PDU) (not shown) via a slip ring (not shown) and then a high voltage generator (not shown), and may generate and emit an X-ray. When the high voltage generator applies a predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detector 108 may be positioned to face the X-ray generator 106. The X-ray detector 108 may include a plurality of X-ray detecting devices. Each of the plurality of X-ray detecting devices may establish one channel but one or more embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be collected wiredly or wirelessly by the DAS 116. Also, the electrical signals generated by the X-ray detector 108 may be provided to an analog-to-digital converter (not shown) via an amplifier (not shown).

According to a slice thickness or the number of slices, only some of a plurality of pieces of data collected by the X-ray detector 108 may be provided to the image processor 126 via the data transmitter 120, or the image processor 126 may select only some of the plurality of pieces of data.

Such a digital signal may be provided to the image processor 126 via the data transmitter 120. The digital signal may be provided to the image processor 126 wiredly or wirelessly.

The controller 118 may control an operation of each of the elements in the CT system 100. For example, the controller 118 may control operations of the table 105, the rotation driver 110, the collimator 112, the DAS 116, the storage 124, the image processor 126, the input 128, the display 130, the communicator 132, and the like.

The image processor 126 may receive data acquired by the DAS 116 (e.g., raw data that is data before processing), via the data transmitter 120, and may perform pre-processing.

The pre-processing may include, for example, an operation of correcting a sensitivity irregularity between channels and an operation of correcting signal loss due to a rapid decrease in signal strength or due to the presence of an X-ray absorbing material such as metal.

Data output from the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-ray that has passed through the object 10. For convenience of explanation, a group of a plurality of pieces of projection data that are simultaneously obtained from all channels at the same imaging angle is referred to as a projection data set.

The storage 124 may include at least one storage medium from among a flash memory-type storage medium, a hard disk-type storage medium, a multimedia card micro-type storage medium, a card-type memory (e.g., an SD card, an XD memory, and the like), a random-access memory (RAM), a static a random access memory (SRAM), read-only memory (ROM), an electrically erasable programmable ROM (EEPROM), a programmable ROM (PROM), a magnetic memory, a magnetic disc, and an optical disc.

The image processor 126 may reconstruct a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The input 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input 128 may include a device for receiving a predetermined input from an external source. For example, the input 128 may include a microphone, a keyboard, a mouse, a joystick, a touchpad, a touch pen, a voice recognition device, a gesture recognition device, or the like.

The display 130 may display an X-ray image reconstructed by the image processor 126.

Exchanges of data, power, or the like between the aforementioned elements may be performed by using at least one of wired communication, wireless communication, and optical communication.

The communicator 132 may perform communication with an external device, an external medical apparatus, etc. via a server 134 or the like. The communication will now be described with reference to FIG. 3.

FIG. 3 is a block diagram for explaining communication performed by the communicator 132.

The communicator 132 may be wiredly or wirelessly connected to a network 301 and therefore may perform communication with the server 134, a medical apparatus 136, or a portable device 138. The communicator 132 may exchange data with a hospital server or other medical apparatuses in a hospital connected via a picture archiving and communications system (PACS). Also, the communicator 132 may perform data communication with the portable device 138 or the like, according to the digital imaging and communications in medicine (DICOM) standard.

The communicator 132 may transmit and receive data related to diagnosing the object 10, via the network 301. Also, the communicator 132 may transmit and receive a medical image obtained from the medical apparatus 136 such as a magnetic resonance imaging (MRI) apparatus, an X-ray apparatus, or the like.

Furthermore, the communicator 132 may receive a diagnosis history or a medical treatment schedule about a patient from the server 134 and may use the diagnosis history or the medical treatment schedule to diagnose the patient. Also, the communicator 132 may perform data communication not only with the server 134 or the medical apparatus 136 in a hospital but also with the portable device 138 of a user or patient.

Also, the communicator 132 may transmit information about a device error, information about a quality control status, or the like to a system manager or a service manager via the network 301, and may receive a feedback regarding the information from the system manager or service manager.

As described with reference to FIGS. 1 through 3, the image processor 126 may reconstruct a tomography image by using data obtained by using tomography imaging, for example, projection data or a sinogram.

FIG. 4 is a block diagram of a tomography imaging apparatus 400 according to an embodiment.

Referring to FIG. 4, the tomography imaging apparatus 400 may include a data obtainer 410, an image processor 420, and a controller 430.

The tomography imaging apparatus 400 may be included in the CT system 100 of FIGS. 1 and 2. Alternatively, the tomography imaging apparatus 400 may be included in the medical apparatus 136 or the portable device 138 of FIG. 3 and may operate by being connected to the CT system 100. In detail, the tomography imaging apparatus 400 may be any medical imaging apparatus for reconstructing an image by using data obtained by using rays transmitted through an object. Hereinafter, data obtained by using tomography imaging may be referred to as 'tomography data'. For example, examples of tomography data may include projection data obtained by using tomography imaging, a sinogram, and a tomography image reconstructed by using the projection data or the sinogram.

That is, the tomography imaging apparatus 40 may be any medical imaging apparatus for reconstructing a tomography image by using projection data obtained by using rays transmitted through an object. In detail, the tomography imaging apparatus 400 may be a CT apparatus, an optical coherence tomography (OCT) apparatus, or a position emission tomography (PET)-CT apparatus. Accordingly, a tomography image obtained by the tomography imaging apparatus 400 according to an embodiment may be a CT image, an OCT image, or a PET image. The following will be explained on the assumption that a CT image is used as a tomography image. Also, when the tomography imaging apparatus 400 is included in the CT system 100 of FIG. 1 or 2, the data obtainer 410, the image processor 420, and the controller 430 of FIG. 4 may be respectively included in the gantry 102, the image processor 126, and the controller 118 of FIG. 2. Hereinafter, a repeated explanation of the same elements and operations of the tomography imaging apparatus 400 as those in FIGS. 1 and 2 will not be given.

The data obtainer 410 obtains data obtained by using tomography imaging. That is, the data obtainer 410 may obtain tomography data. The data obtained by the data obtainer 410 may be raw data or a tomography image generated by using the raw data. Also, the raw data may be projection data obtained by projecting radiation, for example, X-rays, to an object or a sinogram that is a set of projection data. Also, the tomography image may be an image generated by performing filtered back projection on the projection data or the sinogram.

In detail, when the X-ray generator 106 emits X-rays to an object at a predetermined position, a point of view or a direction at or in which the X-ray generator 106 sees the object is referred to as a view. Projection data is raw data obtained to correspond to one view, and a sinogram is raw data obtained by sequentially arranging a plurality of pieces of projection data corresponding to a plurality of views. For example, when the X-ray generator 106 performs tomography imaging by emitting X-rays to the object while moving by every 2°, a point at which the X-ray generator 106 emits X-rays to the object is referred to as a view. For example, when the X-ray generator 106 emits X-rays at each of 90 views for a 180°-angle section, 90 pieces of projection data respectively corresponding to the 90 views are obtained. A sinogram corresponding to the 180°-angle section may be obtained by sequentially arranging the 90 pieces of projection data.

Also, a tomography image may be a complete image showing the whole of a object or an incomplete image showing only a part of the object.

In detail, the data obtainer 410 may receive external data obtained by using tomography imaging, and in this case, the data obtainer 410 may receive at least one of raw data and a tomography image from a tomography imaging apparatus such as the CT system 100 of FIG. 1. Alternatively, the data obtainer 410 may obtain raw data obtained on its own by using tomography imaging, and in this case, the data obtainer 410 may correspond to the gantry 102 of FIG. 2.

The controller 430 controls an overall operation for reconstructing a tomography image. In detail, the controller 430 may obtain information indicating at least one of a motion of an object according to a time point or a motion amount of the object according to a time, and may control a target image to be reconstructed by performing motion correction on the object based on the obtained information.

The tomography imaging apparatus 400 reconstructs a tomography image by using tomography data. In detail, the tomography imaging apparatus 400 may reconstruct a tomography image by using at least one of a half reconstruction method, a full reconstruction method, and a partial angle reconstruction (PAR) method. A method of reconstructing a tomography image will be explained below in detail with reference to FIG. 6.

According to an embodiment, the tomography imaging apparatus 400 operates as follows.

The data obtainer 410 obtains data obtained by performing tomography imaging on a moving object. That is, the data obtainer 410 obtains tomography data.

The image processor 420 reconstructs a tomography image by using at least one of a half reconstruction method, a full reconstruction method, and a PAR method. The image processor 420 may reconstruct a complete image showing the whole of the object by using a half reconstruction method or a full reconstruction method or may reconstruct a partial image showing only a part of the object by using a PAR method.

In an embodiment, the image processor 420 divides the data obtained by the data obtainer 410 into a plurality of data pairs corresponding to a plurality of facing partial angle pairs, and reconstructs a partial image pair by using each of the plurality of data pairs.

The controller 430 obtains motion information indicating a motion of the object in a full section including the plurality of facing partial angle pairs based on the plurality of partial image pairs corresponding to the plurality of data pairs, and controls a target image indicating the object at a target point of time to be reconstructed based on the motion information.

Also, according to an embodiment, the tomography imaging apparatus 400 may operate as follows.

The data obtainer 410 may obtain a first partial image and a second partial image respectively corresponding to a first point of time and a second point of time by using pieces of data obtained in a first angle section and a second angle section that face each other by performing tomography imaging on a moving object.

The image processor 420 may measure a motion amount of the object for the first point of time and the second point of time by using the first partial image and the second partial image, and may reconstruct a target image indicating the object at a target point of time between the first point of time and the second point of time based on a plurality of models indicating a motion of the object between the first point of time and the second point of time set based on the measured motion amount.

The controller 430 may measure image quality of a plurality of the target images respectively reconstructed based on the plurality of models, may select one from among the plurality of models based on the measured image quality, and may control a final target image indicating the object at a target point of time to be reconstructed based on the selected model.

Also, according to an embodiment, the tomography imaging apparatus 400 may operate as follows.

The data obtainer 410 may obtain a first image corresponding to a first point of time and a second image corresponding to a second point of time by performing tomography imaging on an object.

The controller 430 may divide each of the first image and the second image into a plurality of regions, and may obtain a partial motion model indicating a motion of the object between the first point of time and the second point of time by using the first image and the second image in each of the plurality of regions. The controller 430 may obtain a full motion model indicating a motion of the object in a full region including the plurality of regions based on a plurality of the partial motion models respectively corresponding to the plurality of regions.

The image processor 420 may reconstruct a target image indicating the object at a target point of time between the first point of time and the second point of time based on the full motion model.

A detailed operation of the tomography imaging apparatus 400 according to an embodiment will now be explained in detail with reference to FIGS. 5 through 26.

FIG. 5 is a block diagram of a tomography imaging apparatus 500 according to another embodiment. In FIG. 5, a data obtainer 510, an image processor 520, and a controller 530 respectively correspond to the data obtainer 410, the image processor 420, and the controller 430 of FIG. 4, and thus a repeated explanation thereof will not be given.

The tomography imaging apparatus 500 of FIG. 5 may further include at least one of a gantry 540, a user interface 550, a storage 560, a communicator 570, and a display 580, when compared to the tomography imaging apparatus 400 of FIG. 4. The gantry 540, the user interface 550, the storage 560, the communicator 570, and the display 580 included in the tomography imaging apparatus 500 are respectively the same as the gantry 102, the input 128, the storage 124, the communicator 132, and the display 130 of the CT system 100 of FIG. 2 in operations and configurations, and thus a repeated explanation thereof will not be given.

The gantry 540 includes the X-ray generator 106 (see FIG. 2), the X-ray detector 108 (see FIG. 2), and the DAS 116 (see FIG. 2). The gantry 540 projects X-rays to an object, detects X-rays transmitted through the object, and generates raw data corresponding to the detected X-rays.

In detail, the X-ray generator 106 generates X-rays. The X-ray generator 106 projects X-rays to the object while rotating about the object. The X-ray detector 108 detects X-rays transmitted through the object. The DAS 116 generates raw data corresponding to the detected X-rays. The raw data may be projection data obtained by projecting radiation to the object or a sinogram that is a set of projection data.

The tomography imaging apparatus 500 may use any of a PAR method, a full reconstruction method, and a half reconstruction method in order to reconstruct a tomography image.

In detail, the gantry 540 may obtain raw data by performing tomography imaging by using at least one of a half reconstruction method, a full reconstruction method, and a PAR method. The data obtainer 510 reconstructs a tomography image by using the raw data transmitted from the gantry 540 or a tomography system to which the data obtainer 510 is connected.

The display 580 displays a predetermined screen. In detail, the display 580 may display a user interface screen needed to perform tomography imaging or a reconstructed tomography image. In detail, the display 580 may display a user interface screen including at least one of information indicating a motion of the object, for example, motion information, a plurality of models, a selected model, and a full motion model.

Also, the display 580 may be any device by using which a user may visually recognize predetermined data. Examples of the display 580 may include a cathode ray tube (CRT) display, a liquid crystal display (LCD) display, a plasma display panel (PDP) display, an organic light-emitting diode (OLED) display, a field emission display (FED), a light-emitting diode (LED) display, a vacuum fluorescent display (VFD), a digital light processing (DLP) display, a flat panel display (FPD), a 3D display, and a transparent display.

The user interface 550 generates and outputs a user interface screen for receiving a predetermined command or data from the user, and receives a predetermined command or data from the user through the user interface screen. In detail, the user interface screen output from the user interface 550 is output to the display 580. The display 580 may display the user interface screen. The user may see the user interface screen displayed on the display 580, and may recognize predetermined information and may input a predetermined command or data.

The user interface 550 may include a mouse, a keyboard, an input device including hard keys for inputting predetermined data, and a touchpad. For example, the user may input predetermined data or a command by manipulating at least one of the mouse, the keyboard, the input device, and the touchpad included in the user interface 550.

The storage 560 may store various data and/or a program needed to reconstruct a tomography image. In detail, the storage 560 may store data obtained according to tomography imaging. In detail, the storage 560 may store at least one of projection data and a sinogram that are raw data. Also, the storage 560 may store various data and a program needed to reconstruct a tomography image, and may store a finally reconstructed tomography image. Also, the storage 560 may store information indicating a motion or a motion amount of an object.

Also, the storage 560 may include at least one storage medium from among a flash memory-type storage medium, a hard disk-type storage medium, a multimedia card micro-type storage medium, a card type-memory (e.g., an SD card or an XD memory), a RAM, an SRAM, a ROM, an EEPROM, a PROM, a magnetic memory, a magnetic disc, and an optical disc.

The communicator 570 may communicate with an external device or an external medical apparatus. For example, the communicator 570 may be connected to an external tomography system, a tomography imaging apparatus, or a server. Also, the communicator 570 may correspond to the communicator 132 of FIG. 3, and thus a repeated explanation thereof will not be given.

In detail, the communicator 570 may be wiredly or wirelessly connected to the network 301 (see FIG. 3), and may communicate with an external device such as the server 134 (see FIG. 3), the medical apparatus 136 (see FIG. 3), or the portable device 138 (see FIG. 3). The communicator 570 may exchange data with a hospital server or other medical apparatuses in a hospital connected via a PACS.

Also, the communicator 570 may exchange data with an external device according to the DICOM standard.

In an embodiment, the communicator 570 may receive tomography data through the network 301 (see FIG. 3). Furthermore, the communicator 570 may receive a diagnosis history or a medical treatment schedule about a patient from the server 134 (see FIG. 3) and may use the diagnosis history or the medical treatment schedule to diagnose a health state of the patient. Also, the communicator 570 may exchange data with the portable device 138 (see FIG. 3) of the user or the patient as well as the server 134 (see FIG. 3) or the medical apparatus 136 (see FIG. 3) in a hospital.

As described above, the communicator 570 may transmit at least one of a tomography image reconstructed by the image processor 520 and information indicating a motion of the object obtained by the controller 530 to the server 134 (see FIG. 3) or the medical apparatus 136 (see FIG. 3) connected through the network 301 (see FIG. 3) so that data transmitted from an external hospital may be processed, used, or displayed.

An operation of the tomography imaging apparatus 400 or 500 according to an embodiment will now be explained in detail with reference to FIGS. 6 through 26. Also, in FIGS. 6 through 26, the following will be explained on the assumption that the tomography imaging apparatus 500 of FIG. 5 from among the tomography imaging apparatuses 500 and 600 is used.

FIG. 6 is a view for explaining a reconstruction method used for tomography imaging.

The tomography imaging apparatus 500 may reconstruct a tomography image by using at least one of a half reconstruction method, a full reconstruction method, and a PAR method.

A method in which the X-ray generator 106 reconstructs one tomography image by using raw data obtained by making a rotation that is equal to or greater than a half-rotation and less than a full-rotation is referred to as a half reconstruction method and a method in which the X-ray generator 106 reconstructs one tomography image by using raw data obtained by making a full-rotation is referred to as a full reconstruction method. Also, a method in which the X-ray generator 106 reconstructs one tomography image by using raw data obtained by making a rotation that is less than a half-rotation is referred to as a PAR method. A tomography image reconstructed by using a half reconstruction method or a full reconstruction method is a complete image showing the whole of an object whereas a tomography image reconstructed by using a PAR method is an incomplete image showing a part of the object. The incomplete image reconstructed by using the PAR method may be referred to as a 'partial image' or a 'partial angle image'.

Referring to FIG. 6, in a full reconstruction method, the X-ray generator 106 performs tomography imaging by rotating by an angle section 640, which is equal to or greater than a full-rotation, about an object 601. A tomography image is reconstructed by using data obtained in the angle section 640. In the full reconstruction method of FIG. 6, the X-ray generator 106 performs tomography imaging by rotating by 360+a°.

In a half reconstruction method, the X-ray generator 106 performs tomography imaging by rotating by an angle section 620, which is equal to or more greater than a half-rotation, about the object 601. A tomography image is reconstructed by using data obtained in the angle section 620. In the half reconstruction method of FIG. 6, the X-ray generator 106 performs tomography imaging by rotating by 180+a°. a° may be equal to or greater than 0° and may be a fan angle when tomography imaging is performed by using a cone beam.

In a PAR method, the X-ray generator 106 performs tomography imaging by rotating by an angle section 641 or 645 less than 180°, which is equal to or less than a half-rotation, about the object 601. A tomography image is reconstructed by using data obtained in the angle section 641 or 645. In the PAR method of FIG. 6, the X-ray generator 106 performs tomography imaging by rotating by a° that is less than 180°.

Also, an angle section in which pieces of projection data needed to reconstruct one tomography image are obtained may be referred to as 'one cycle angle section'. When a tomography image is reconstructed by using a full angle reconstruction method, one cycle angle section may be 360+a°. Also, when a tomography image is reconstructed by using a half reconstruction method, one cycle angle section may have a value of 180+a°.

The following will be explained on the assumption that a half reconstruction method is used to reconstruct a tomography image. Accordingly, one cycle angle section has a value of 180+a°.

In an embodiment, the tomography imaging apparatus 500 may reconstruct a target image with reduced motion artifacts or motion blur by performing motion correction on an object based on motion information indicating a motion of the object obtained based on a plurality of data pairs corresponding to facing partial angle pairs.

FIG. 7 is a view for explaining an operation of the tomography imaging apparatus 500 according to an embodiment.

The image processor 520 divides tomography data obtained by the data obtainer 510 into a plurality of data pairs.

Referring to FIG. 7, the image processor 520 may receive tomography data obtained when the X-ray generator 126 performs tomography imaging by making a full-rotation or more about an object 701. The image processor 520 divides the tomography data into a plurality of data pairs corresponding to a plurality of facing partial angle pairs, and reconstructs a partial image pair by using each of the plurality of data pairs. The partial image pair refers to an image pair reconstructed by using a PAR method. In detail, the data obtainer 510 may obtain tomography data obtained when the X-ray generator 126 makes a full-rotation or more according to various scan modes, and the image processor 520 may divide the tomography image obtained in an angle section corresponding to the full-rotation or more into a plurality of data pairs.

Examples of a scan mode used for tomography imaging may include a prospective mode and a retrospective mode. The scan mode may be divided according to whether a cardiac cycle of a patient to be imaged is constant or not. Also, electrocardiogram (ECG) gating may be used to obtain tomography data used to reconstruct an image. When a patient has a constant cardiac cycle, an ECG signal may be regularly gated by using a prospective mode, and a tomography image may be reconstructed by using tomography data of a section corresponding to the gated ECG signal. However, when a patient such as a person suffering from an irregular heart rhythm has a non-constant cardiac cycle, a cardiac cycle may be irregular and thus may not be uniformly detected as in a prospective mode. In this case, an ECG signal may be irregularly gated by using a retrospective mode. In the retrospective mode, tomography data may be obtained by projecting X-rays to an object in all cycles of an ECG signal or a predetermined continuous cycle, partial cycles for reconstructing a tomography image may be selected, and a tomography image may be reconstructed by using tomography data corresponding to the selected partial cycles.

The tomography imaging apparatus 500 according to an embodiment may divide tomography data obtained by scanning by 360° or more in a retrospective mode into a plurality of data pairs.

Each of a plurality of facing partial angle pairs may include a first angle section having a value less than 180° and a second angle section facing the first angle section. In detail, a partial angle pair refers to two partial angles in a conjugate angle relationship. An angle difference between two angle sections in a conjugate angle relationship is 180°. For example, one partial angle pair includes an angle section 711 that is a first angle section and an angle section 712 that is a second angle section, and the angle section 711 and the angle section 712 are in a conjugate angle relationship.

In detail, the image processor 520 may divide an angle section corresponding to a full-rotation or more into a plurality of facing partial angle pairs. In FIG. 7, one partial angle section has a value of 45°. Referring to FIG. 7, the image processor 520 may divide a 360°-angle section into 8 angle sections, that is, 4 partial angle pairs. In detail, the 360°-angle section may include a partial angle pair including an angle section 711 and an angle section 712, a partial angle pair including an angle section 721 and an angle section 722, a partial angle pair including an angle section 731 and an angle section 732, and a partial angle pair including an angle section 741 and an angle section 742.

In FIG. 7, the object 701 is, for example, the belly of a patient, and a cross-section of the belly is located on an xy plane. Also, although 0° that is a start point of the angle section 711 is not matched to the y-axis in FIG. 7, the start point of the angle section 711 may be matched to the y-axis.

Also, in FIG. 7, a full section including a plurality of partial angle pairs has a value of 360°. In detail, the full section including all of the partial angle pair including the angle section 711 and the angle section 712, the partial angle pair including the angle section 721 and the angle section 722, the partial angle pair including the angle section 731 and the angle section 732, and the partial angle pair including the angle section 741 and the angle section 742 may be a 360°-angle section.

Also, the full section may be an angle section as shown in FIG. 7, or may be a time section corresponding to the angle section. In detail, the full section may be a time section taken for the X-ray generator 106 to rotate by a 360°-angle section. For example, when it takes 2 seconds for the X-ray generator 106 to rotate by 360° and the X-ray generator 106 rotates at a constant velocity, the full section may be a 360°-angle section or a 2 sec-time section. In this case, an angle point of 0° included in the full section may correspond to a time point of 0 seconds, an angle point of 360° may correspond to a time point of 2 seconds, and an angle point of 180° may correspond to a time point of 1 second.

The image processor 520 reconstructs partial image pairs corresponding to the partial angle pairs. In detail, each of a plurality of partial image pairs reconstructed by the image processor 520 may include a first partial image reconstructed by using data obtained in the first angle section and a second partial image reconstructed by using data obtained in the second angle section.

Referring to FIG. 7, the image processor 520 may generate a partial image pair including a first partial image reconstructed by using tomography data obtained in the angle section 711 that is the first angle section and a second partial image reconstructed by using tomography data obtained in the angle section 712 that is the second angle section. The partial image pair including the first partial image and the second partial image will now be explained in detail with reference to FIGS. 8 and 9A.

FIG. 8 is a view for explaining an operation performed by the tomography imaging apparatus 500 to obtain information indicating a motion of an object according to an embodiment.

Referring to FIG. 8, the image processor 520 may obtain a plurality of partial image pairs 810, 820, 830, and 840 corresponding to a plurality of partial angle pairs.

In detail, the image processor 520 may generate the partial image pair 810 including a first partial image 811 reconstructed by using tomography data obtained in the angle section 711 and a second partial image 812 reconstructed by using tomography data obtained in the angle section 712.

Also, the image processor 520 may generate the partial image pair 820 including a first partial image 821 reconstructed by using tomography data obtained in the angle section 721 and a second partial image 822 reconstructed by using tomography data obtained in the angle section 722. Also, the image processor 520 may generate the partial image pair 830 including a first partial image 831 reconstructed by using tomography data obtained in the angle section 731 and a second partial image 832 reconstructed by using tomography data obtained in the angle section 732. Also, the image processor 520 may generate the partial image pair 840 including a first partial image 841 reconstructed by using tomography data obtained in the angle section 741 and a second partial image 842 reconstructed by using tomography data obtained in the angle section 742.

The controller 530 may obtain motion information indicating a motion of an object according to a time based on the plurality of partial image pairs corresponding to the plurality of data pairs. In detail, the motion information may be information indicating a motion of a surface of the object at a time point. The motion may be a difference of at least one of a shape, a size, and a position between the object included in the first partial image and the object included in the second partial image.

In detail, the controller 530 may obtain motion information indicating a motion of the object that is 3D-imaged at each time point by using each of the plurality of partial image pairs corresponding to the plurality of partial angle pairs.

In detail, the image processor 520 may reconstruct a 3D tomography image. In detail, the image processor 520 may generate a 3D partial image that expresses the object in a 3D space by using tomography data obtained in a partial angle section. Motion information obtained by the image processor 520 may be information indicating a motion of the object in a four-dimensional (4D) space including a 3D space and a time point and may be referred to as '4D motion information'.

The controller 530 may obtain motion information based on a plurality of partial images respectively corresponding to the plurality of partial angles included in a full section. The motion information may be information indicating a motion of a surface of the object in the full section. In detail, the motion information may be information indicating a motion of the surface of the object at each angle point or time point included in the full section.

An operation of obtaining a partial image pair and motion information will now be explained in detail with reference to FIGS. 9A, 9B, and 10.

FIG. 9A is a view for explaining a partial image pair reconstructed by the tomography imaging apparatus 500 according to another embodiment. In FIG. 9A, an angle section 910 may correspond to the angle section 620 of FIG. 6 and may have a value of 180+a°. The following will be explained on the assumption that a first angle section 911 and a second angle section 912 included in one partial angle pair respectively correspond to the angle section 711 that is a first angle section and the angle section 712 that is a second angle section included in a partial angle pair of FIG. 7.

In FIG. 9A, a first partial image 932 is reconstructed by using tomography data obtained in the first angle section 911 and a second partial image 942 is reconstructed by using tomography data obtained in the second angle section 912. The first partial image 932 and the second partial image 942 respectively correspond to the first partial image 811 and the second partial image 812 of FIG. 8. The first partial image 932 and the second partial image 942 may be 3D tomography images that express an object in a 3D space defined by the x, y, and z-axes. Alternatively, the first partial image 932 and the second partial image 942 may be a 2D tomography images that express the object in a 2D space defined by the x and y-axes.

In detail, the X-ray generator 106 may perform tomography imaging by rotating about an object 901 and may obtain projection data or a sinogram that is raw data corresponding to the first angle section 911. The X-ray generator 106 reconstructs a tomography image 931 by using the obtained raw data.

Raw data obtained in the first angle section 911 and the second angle section 912 may be data obtained by detecting X-rays projected to the object from a single source or a dual source. For example, when tomography imaging is performed by using a single source, the single source may perform tomography imaging by moving by the first angle section 911 and the second angle section 912. Alternatively, when tomography imaging is performed by using a dual source, at least one of a first source and a second source included in the dual source may perform tomography imaging by moving by at least one of the first angle section 911 and the second angle section 912. In detail, the first source may obtain raw data by rotating by the first angle section 911 and the second source may obtain raw data by rotating by the second angle section 912.

Also, various reconstruction methods may be used to reconstruct a tomography image by using tomography imaging. For example, filtered back projection or iterative reconstruction may be used by the tomography imaging apparatus 500 to reconstruct a tomography image.

Back projection is a method of projecting pieces of projection data obtained in a plurality of directions (views) back over a pixel surface, summing the pieces of projection data, and reconstructing an image. In detail, back projection may obtain an image similar to a real image by using pieces of projection data in a plurality of directions. Also, in order to remove artifacts in a reconstructed image and to improve image quality, filtering may be additionally performed.

Filtered back projection is an improved back projection method for removing artifacts or blur which may occur in back projection. Filtered back projection involves filtering raw data before back projection, performing back projection on the filtered raw data, and reconstructing a tomography image.

Filtered back projection is the most widely used method for reconstructing a tomography image, is simply performed, and is effectively performed with a small amount of calculation. Filtered back projection is the mathematical inverse of the Radon transform that is an operation of obtaining a sinogram from a 2D image and relatively easily converts a 2D image into a 3D image. In detail, filtered back projection is a method of filtering projection data by using a Shepp and Logan filter that is a high-pass filter, performing back projection, and reconstructing an image.

The following will be explained on the assumption that a tomography image is reconstructed by using filtered back projection.

Referring to FIG. 9A, the data obtainer 510 obtains the tomography image 931 by performing filtered back projection on raw data obtained in the first angle section 911. In detail, each of the first angle section 911 and the second angle section 912 has a value less than 180°. In order to more clearly show surfaces 935 and 936 of an object in the tomography image 931, the first partial image 932 that is finally reconstructed by filtering the tomography image 931 may be obtained. In detail, the first partial image 932 may be an incomplete image reconstructed by using a PAR method.

The image processor 520 may reconstruct the second partial image 942 in the same manner as that used to reconstruct the first partial image 932.

The tomography imaging apparatus 500 according to an embodiment uses a PAR method to obtain the first partial image 932 and the second partial image 942. Since the X-ray generator 106 performs tomography imaging by rotating at a constant velocity, an angle value when tomography data is obtained is proportional to a time value. That is, when a value of a predetermined angle section decreases, a time taken to obtain tomography data in the predetermined angle section decreases. Accordingly, assuming that a PAR method is used, as an angle section used to reconstruct the first partial image 932 and the second partial image 942 decreases, a time resolution may increase. Hence, since the first partial image 932 and the second partial image 942 are partial angle images with a high time resolution and few motion artifacts, the first partial image 932 and the second partial image 942 may clearly show a part of the object without blur.

In FIG. 9A, 2D tomography images, for example, the first partial image 932 and the second partial image 942, are reconstructed. Surfaces (e.g., 935 and 936, or 945 and 946) of the object in a 3D tomography image may be expressed as edges in a 2D tomography image, like in the first partial image 932 and the second partial image 942.

Since the first angle section 911 and the second angle section 912 are in a conjugate angle relationship and X-rays are projected in the same direction to the object in the first angle section 911 and the second angle section 912, the first angle section 911 and the second angle section 912 have the same view. Accordingly, a body part of the object reconstructed by using pieces of projection data obtained in the first angle section 911 and a body part of the object reconstructed by using pieces of projection data obtained in the second angle section 9+321 are the same.

Assuming that the object is a moving object, when data is obtained at different points of time, at least one of a position, a size, and a shape of the object is different due to a motion of the object. That is, a state of the object in the first angle section 911 and a state of the object in the second angle section 912 are different from each other.

As described above, since the first partial image 932 and the second partial image 942 are images of the same body part of the object, when the first partial image 932 and the second partial image 942 are compared with each other, a motion of the object which occurs in the first angle section 911 and the second angle section 912 may be measured.

FIG. 9B is a view for explaining an operation performed by the tomography imaging apparatus 500 to obtain information indicating a motion of an object according to another embodiment.

In FIG. 9B, the same elements as those in FIG. 8 are denoted by the same reference numerals. That is, referring to FIGS. 8 and 9B, the image processor 520 may reconstruct the partial image 811, the partial image 821, the partial image 831, the partial image 841, the partial image 812, the partial image 822, the partial image 832, and the partial image 842 based on pieces of data respectively obtained in the partial angle 711, the partial angle 721, the partial angle 731, the partial angle 741, the partial angle 712, the partial angle 722, the partial angle 732, and the partial angle 742. A partial image of FIG. 9B may be expressed by using a voxel value in a 3D image grid.

The controller 530 may obtain motion information indicating a motion of an object according to a time so that each of the partial images 811, 821, 831, 841, 812, 822, 832, and 842 included in a plurality of partial image pairs has a first shape, which may be predetermined, at a predetermined time point included in a full section.

In detail, the controller 530 may estimate a motion state of the object at a first point of time that is a predetermined point of time included between the partial angle 711 and the partial angle 712 based on a result of comparison between the partial image 811 and the partial image 812 that form one partial image pair. The controller 530 may estimate a motion state of the object at the first point of time that is a predetermined point of time included between the partial angle 721 and the partial angle 722 based on a result of comparison between the partial image 821 and the partial image 822 that form another partial image pair. Continuously, the controller 530 may estimate a motion state of the object at the first point of time that is a predetermined point of time included between the partial angle 731 and the partial angle 732 based on a result of comparison between the partial image 831 and the partial image 832 that form another partial image pair. Continuously, the controller 530 may estimate a motion state of the object at the first point of time that is a predetermined point of time included between the partial angle 741 and the partial angle 742 based on a result of comparison between the partial image 841 and the partial image 842 that form another partial image pair.

The controller 530 may estimate a final motion state of the object at the first point of time by interpolating the plurality of motion states of the object estimated by using the plurality of partial image pairs. The final motion state indicates a state of the object at the first point of time, and the controller 530 obtains motion information indicating the final motion state.

In FIG. 9B, edges such as an inner small circle 950 and an outer large circle 955 are shown. Also, a state of the object is changed due to a motion of the object according to a time. In detail, due to a motion of the object according to a time, at least one of a shape, a size, and a position of the object may be changed. In FIG. 9B, a shape of the object is maintained whereas a size of the object is changed.

For example, since the partial image 811 and the partial image 812 form a partial image pair corresponding to a facing partial angle pair, the partial image 811 and the partial image 812 are images of the same body part of the object. In detail, the partial image 811 shows some edges 951, 952, 953, and 954 of the object, and the partial image 812 shows the same edges as the edges 951, 952, 953, and 954 of the partial image 811. The controller 530 may obtain a motion of the object so that the partial image 811 and the partial image 812 have a predetermined shape at a first point of time, for example, a time point corresponding to an angle point of 180°.

Also, the partial image 821 shows some edges 961, 962, 963, and 964 of the object, and the partial image 822 shows the same edges as the edges 961, 962, 963, and 964 of the partial image 821. The controller 530 may obtain a motion of the object so that the partial image 821 and the partial image 822 have into a predetermined shape at the first point of time, for example, at a time point corresponding to an angle point of 180°.

In the same manner, the controller 530 may obtain a motion of the object so that a first partial image and a second partial image included in each of a plurality of partial image pairs have a predetermined shape at the first point of time. The controller 530 may obtain a motion of the object so that partial images included in a plurality of partial image pairs finally have a predetermined shape at the first point of time. For example, the controller 530 may estimate that a state of the object is like in an image 972 at the first point of time, for example, a time point corresponding to an angle point of 180°, based on partial images included in a plurality of partial image pairs. The controller 530 may obtain motion information corresponding to the estimated state of the object.

Also, although motion information is obtained by estimating a motion state of the object at the first point of time for convenience of explanation, the controller 530 may estimate a motion state of the object in the same manner as that described above at each of a plurality of points of time included in a full section and may obtain motion information based on the estimated motion state.

FIG. 10 is a graph for explaining an operation performed by the tomography imaging apparatus 500 to obtain information indicating a motion of an object according to another embodiment. In the graph of FIG. 10, the x-axis represents a rotation angle of the X-ray generator 106 and the y-axis represents a motion amount of the object at a point of time corresponding to each rotation angle. That is, the x-axis represents a full section that is an angle section. The y-axis represents a motion amount of the object which occurs at a subsequent point of time when an angle point of 0° is a start point.

As described with reference to FIG. 7, when 360° is divided by 45° into 8 angles, a full section may be a 360°-angle section and each partial angle section may be a 45°-angle section. As described with reference to FIGS. 9A and 9B, the controller 530 may estimate a motion state of an object at a time point based on a plurality of partial images included in a plurality of partial image pairs and may obtain motion information corresponding to the estimated motion state. In FIG. 10, for convenience of explanation, motion information is represented as a graph 1015 that is a motion curve indicating a motion amount of the object according to a time.

However, when a partial image is a 3D image, motion information may be represented as a motion vector field (MVF) indicating a change in a surface of the object according to a time. In detail, an MVF indicating a motion of the object at each time point included in a 360°-angle section that is a full angle section may be calculated, and the MVF according to each time point may be obtained as motion information.

Once the motion information is obtained, the controller 530 may estimate a motion amount of the object at a target point of time based on the motion information and may control a target image to be reconstructed based on the estimated motion amount. For example, when the target point of time is set to a point of time corresponding to a point 1031 of 180°, projection data obtained in a view of the point 1031 of 180° is not corrected and a surface of the object imaged by pieces of projection data obtained in views of other points or pieces of projection data obtained in other angle sections is corrected based on a weight value 1032 corresponding to the point 1031 of 180° of the graph 1015. The target image may be reconstructed by using the corrected projection data. For example, in the graph 1015 that is motion information, motion correction may be performed on a partial image obtained in each of a plurality of views or a plurality of pieces of projection data obtained in a plurality of views included in an angle section from 0° to 360° according to a motion corresponding to the weight value 1032 corresponding to the point 1031 of 180° that is a target point. Accordingly, a motion-corrected target image may be reconstructed.

An operation of reconstructing a target image based on motion information will be explained below in detail with reference to FIGS. 12 and 13.

Although motion information is represented as a graph in FIG. 10, motion information may be individually obtained in each view. Alternatively, motion information may be individually obtained in each voxel or pixel. Also, motion information may be individually obtained in each group of voxels or pixels.

The controller 630 may estimate a motion amount of an object at a target point of time based on motion information and may control a target image to be reconstructed based on the estimated motion amount. An operation of reconstructing a target image will be explained below in detail with reference to FIGS. 12 through 17. FIGS. 11A through 11C are views for explaining an operation performed by the tomography imaging apparatus 500 to obtain information indicating a motion of an object according to another embodiment. In detail, FIG. 11A is a view for explaining an operation of comparing a first partial image with a second image. FIG. 11B is a view illustrating a motion of an object included in the first partial image and the second partial image. FIG. 11C is a view for explaining a motion of an object in a time section between a first angle section and a second angle section.

The controller 530 may estimate a motion of an object at a first point of time based on a first partial image 1110 and a second partial image 1120.

Referring to FIG. 11A, the first partial image 1110 and the second partial image 1120 respectively correspond to the first partial image 932 and the second partial image 942 of FIG. 9A. However, for convenience of explanation, the first partial image 1110 and the second partial image 1120 are complete images.

The first partial image 1110 and the second partial image 1120 are tomography images of a moving object. Also, in FIG. 11A, one or more objects 1111 and 1112 or 1121 and 1122 included in one image are shown as circular solid objects.

In detail, in order to compare a motion of an object, the objects 1111 and 1112 included in the first partial image 1110 are compared with the objects 1121 and 1122 included in the second partial image 1120. According to a comparison result, as shown in a comparative image 1130, a motion of an object for a time section 1190 between a first angle section 1161 and a second angle section 1162 may be obtained. The first angle section 1161 and the second angle section 1162 respectively correspond to the first angle section 911 and the second angle section 912 of FIG. 9A.

In detail, the information indicating the motion of the object for the time section 1190 that is information corresponding to an MVF between the first partial image 1110 and the second partial image 1120 may include information indicating a motion amount of a surface of the object according to a time.

Referring to FIG. 11B, surfaces indicating the same body part of the object included in the first partial image 1110 and the second partial image 1120 may be compared with each other and a motion vector indicating a direction and a position difference value between the compared surfaces may be obtained. The motion vector may be used as a motion amount of the object. Information indicating a motion amount of a predetermined body part of the object and including motion vectors may be an MVF. That is, the MVF indicates a motion amount of a surface of the object.

The MVF is information obtained to extract a motion of the object, and the controller 530 may measure a motion amount of the object by using non-rigid registration. Alternatively, the controller 530 may measure a motion amount of the object by using any of various methods of measuring a motion such as rigid registration, optical flow, and/or feature matching.

The following will be explained on the assumption that non-rigid registration is used to obtain an MVF.

In detail, a plurality of control points are set over an image grid of the first partial image 1110 or the second partial image 1130 and an optimal motion vector at each of the control points is calculated. The term 'motion vector' refers to a vector including a direction and a magnitude of a motion. An MVF including motion vectors in all voxels is obtained by interpolating motion vectors at control points.

For example, B-spline free-form deformation may be used as a method of interpolating motion vectors. Also, an optimization method may be used as a method of calculating an optimal motion vector at each control point. In detail, the optimization method involves updating an MVF by repeatedly updating motion vectors at a plurality of control points, warping the first partial image 1110 or the second partial image 1120 based on the updated MVF, comparing a warped first partial image or second partial image with the first partial image 1120 or the second partial image 1110, ending repetition when a similarity between warped first partial image or second partial image and the first partial image 1120 or the second partial image 1110 is the highest, and calculating a motion vector. The similarity may be measured as a negative number of a sum of squared differences of brightness of two compared images.

Alternatively, a control point may be set on a surface of the object, control points indicating the same point of the object in the first partial image 1110 and the second partial image 1120 may be compared with each other, and a motion vector may be obtained. In detail, control points may be matched to each other to obtain a relative difference between the control points. The relative difference may be used as a motion vector at a current control point. An MVF indicating motion vectors in all voxels is obtained by interpolating motion vectors at control points. As described above, B-spline free-form deformation may be used as a method of interpolating motion vectors.

Referring to FIG. 11C, in a graph 1170, the x-axis represents an angle section or a time section between the first angle section 1161 and the second angle section 1162, and the y-axis represents a weight value W corresponding to a motion amount of the object. Hereinafter, an angle section or a time section including an angle section from the first angle section 1161 to the second angle section 1162 is referred to as a 'first time section 1190'.

In detail, the graph 1170 that is information corresponding to an MVF between the first partial image 1110 and the second partial image 1120 may be information indicating a motion amount of the object corresponding to each time point. In detail, the graph 1170 may be information indicating a motion amount of a surface of the object corresponding to each time point. The 'each time point' may be an arbitrary point of time included in the first time section 1190.

When a motion change amount of the second partial image 1120 obtained in the second angle section 1162 is measured by using the first partial image 1110 obtained in the first angle section 1161 that is a start section of the first time section 1190 as a reference image, a motion amount of the first partial image 1110 may be matched to 0% and a motion amount of the second partial image 1120 may be matched to 100%. A value of an MVF that is a motion amount between the first partial image 1110 and the second partial image 1120 is expressed with a weight value W. Also, a motion amount may be a sum of absolute values of all motion vectors in an MVF. Also, a motion amount may be turned into a weight value and may be expressed with the weight value.

Also, as shown in FIG. 11C, when a time and the weight value W indicating a motion amount of the object have a linear relationship, the weight value and the time may have a shape of the graph 1170. Alternatively, a shape of a graph corresponding to first information may be arbitrarily defined by a user or may be optimized and set in consideration of the object. For example, when the object is the heart, a shape of the graph 1170 may be non-linear according to a motion state of the heart at a point of time at which the object is to be reconstructed.

In detail, when a motion amount of an object and a time have a linear relationship, the data obtainer 510 may respectively match a zero MVF and an MVF indicating a motion amount between the first partial image 1110 and the second partial image 1120 to a first weight value and a second weight value. In detail, the zero MVF may correspond to a start point of the first time section 1190, and the MVF indicating a motion amount between the first partial image 1110 and the second partial image 1120 may correspond to an end point of the first time section 1190. Referring to FIG. 11C, in the graph 1170, a weight value of 0 indicating the zero MVF may be matched to a start point of 0° (t=0) of the first time section 1190 and a weight value of 1 indicating the MVF indicating a motion amount between the first partial image 1110 and the second partial image 1120 may correspond to an angle point of 180+a° (t=end) that is an end point of the first time section 1190. Also, a time and a weight value have a linear relationship.

A first point of time t1 corresponds to the first partial image 1110 and a second point of time t2 corresponds to the second partial image 1120. For example, it is assumed that raw data for restoring the first partial image 1110 is obtained in a section from 0 to 0.03 seconds in a section of 0.2 seconds corresponding to one cycle angle section 1160. The first point of time t1 may be an intermediate point of time of 0.015 seconds in a section from 0 to 0.03 seconds. That is, when a predetermined image is reconstructed by using raw data obtained in a predetermined time section, a point of time corresponding to the predetermined image may be an intermediate point of time in a predetermined time section. Also, the first partial image 1110 corresponding to the first point of time t1 may correspond to a view when the X-ray generator 116 sees the object at a position corresponding to the first point of time t1. Also, the second partial image 1120 corresponding to the second point of time t2 may correspond to a view when the X-ray generator 116 sees the object at a position corresponding to the second point of time t2.

Also, in the first information, when a weight value ranges from 0 to 1, a minimum weight value of 0 may correspond to a motion amount at a point or a point of time at which a size of the object in the first time section 1190 is the smallest, and a maximum weight value of 1 may correspond to a motion amount at a point or a point of time at which the object in the first time section 1190 is the largest.

Also, in the first information, a relationship between a motion amount and a time may be determined by a quadratic relationship or a relationship that is modeled by statistical information.

For example, a motion pattern of an object may be statistically modeled. In detail, when the object is the heart, a motion of the heart may be statistically modeled, and a shape of the graph 1170 in the first time section 1190 may be set to correspond to the modeled motion of the heart.

Also, a shape of a graph indicating a motion pattern of an object may vary according to the object. For example, when the object is the entire heart, a shape of the graph may reflect a motion pattern of the entire heart. Also, when the object is a coronary artery included in the heart, a shape of the graph may reflect a motion pattern of the coronary artery. Also, even when the object is the coronary artery included in the heart, a motion pattern may vary according to a position of the coronary artery included in the heart, and a shape of a graph that is motion information may be set to vary according to the position of the coronary artery. Also, when the object is a mitral valve (MV) included in the heart, a shape of a graph may reflect a motion pattern of the MV.

Also, a motion pattern may vary according to each of partial regions of an object to be tomography-imaged. In this case, in order to reflect different motion patterns according to partial regions, motion information of each of the partial regions may be obtained. A target image indicating the entire object may be reconstructed by performing motion correction on each of the partial regions by using the motion information obtained according to each of the partial regions. For example, when the object is the heart, motion patterns of a left ventricle, a right ventricle, a left atrium, and a right atrium may be different from one another. In this case, motion information of each of the left ventricle, the right ventricle, the left atrium, and the right atrium may be individually obtained, motion correction may be performed on a partial image of each of the left ventricle, the right ventricle, the left atrium, and the right atrium, and a target image indicating the heart may be reconstructed by combining motion-corrected partial images.

Also, in order for the graph 1170 indicating a motion of an object to more accurately reflect a motion change between the first partial image 1110 and the second partial image 1120, when the graph 1170 is to be obtained, a motion change of the object in an angle section between the first angle section 1161 and the second angle section 1162 may be estimated by using raw data obtained in the one cycle angle section 1160.

For example, the tomography imaging apparatus 500 compares estimated projection data obtained by performing forward projection on a target image reconstructed by using the graph 1170 at a target point of time with measured projection data obtained by using tomography imaging at the target point of time. The tomography imaging apparatus 500 may correct the graph 1170 to reduce an error between the estimated projection data and the measured projection data. As described above, the tomography imaging apparatus 500 may repeatedly correct the graph 1170 so that the graph 1170 accurately reflects a motion of the object.

FIG. 12 is a view for explaining a motion of an object estimated based on information indicating a motion of the object.

Since motion information includes information indicating a motion of an object according to a time, a state according to the motion of the object at a predetermined point of time may be estimated by using the motion information. In detail, a state change of the object in a full section, for example, a 360°-section, may be estimated by using motion information. For convenience of explanation, in FIG. 12, a° is 45° and only a state change of the object in an angle section from 0° to 225° is shown. For example, referring to the graph 1015 that is motion information of FIG. 10, an object 1205 moves at a constant velocity and expands at a constant velocity according to a time. A state change of the object in FIG. 12 is an expansion at a constant velocity. In FIG. 12, information indicating a motion amount of the object, for example, the graph 1015, may have a linear shape.

For example, when the object 1205 has a first size 1220 at a first point of time t11 corresponding to a first angle section 1211, the controller 530 may estimate that a size of the object at a second point of time t12 is changed by a first change amount 1242 from the first size 1220. Accordingly, the controller 530 may estimate that a size of the object at the second point of time t12 is a second size 1221.

Also, the controller 530 may estimate that a size of the object at a third point of time t13 is changed by a second change amount 1244 from the first size 1220, and thus a size of the object at the third point of time t13 is a third size 1222. The controller 530 may estimate that a size of the object at a fourth point of time t14 is changed by a third change amount 1246 from the first size 1220, and thus a size of the object at the fourth point of time t14 is a fourth size 1223.

Also, sizes of the object at the second point of time t12, the third point of time t13, and the fourth point of time t14 may be estimated by reducing the object having a fifth size 1230 based on motion information.

In detail, a state of an object including at least one of a size, a shape, and a position of the object at a target point of time included in a full section, for example, a time section corresponding to a 360°-angle section, may be estimated by using motion information. In FIG. 12, the controller 530 may estimate a state change amount of the object at the target point of time by using motion information and may generate a target image by warping the object based on the estimated state change amount.

The warping of the object refers to motion correction performed on the object and involves estimating a state of the object (for example, at least one of a size, a shape, and a position) at a target point of time by using motion information and reconstructing a target image by correcting a motion of the object according to the estimated state.

In detail, the controller 530 may estimate a motion amount of the object at a target point of time based on motion information and may control a target image to be reconstructed based on the estimated motion amount.

In detail, the controller 530 may reconstruct a target image by warping images according to a plurality of views indicating a part of the object based on motion information. An operation of reconstructing a target image by using warping will be explained below in detail with reference to FIGS. 14 through 17.

FIG. 13 is a view for explaining an operation of measuring a motion of an object according to an embodiment.

FIG. 13 is a detailed view for explaining an operation of obtaining a motion amount between a first partial image and a second partial image by using a data pair obtained from a partial angle pair.

Referring to FIG. 13, the X-ray generator 106 obtains a first partial image 1350 by using pieces of projection data corresponding to a first angle section 1301 obtained by rotating about an object 1305. The first partial image 1350 includes surfaces 1351 and 1352 included in a first solid object 1306 and surfaces 1353 and 1354 included in a second solid object 1307. Also, the X-ray generator 106 obtains a second partial image 1360 by using pieces of projection data corresponding to a second angle section 1302 obtained by rotating about the object 1305. The second partial image 1360 includes surfaces 1361 and 1632 included in the first solid object 1306 and surfaces 1363 and 1364 included in the second solid object 1307.

Pieces of projection data obtained in each predetermined angle section or each view included in one cycle angle section are used to obtain images of different surfaces or different regions of an object.

Since surfaces of the same body part of the object are displayed in the first partial image 1350 and the second partial image 1360, an MVF 1380 indicating a motion of the object is obtained by comparing the first partial image 1350 and the second partial image 1360 as in an image 1330. Since vectors 1381 and 1382 indicating a movement direction and a movement distance of the same body part surface are included in the MVF 1380, information indicating a motion of the object between a first point of time T1 and a second point of time T2 may be obtained by using the MVF 1380.

Since the first partial image 1350 and the second partial image 1360 are images reconstructed by using pieces of projection data obtained in partial angle sections, the first partial image 1350 and the second partial image 1360 may be images with a high time resolution and reduced motion artifacts. Accordingly, when the first partial image 1350 and the second partial image 1360 are compared with each other, information indicating a motion of the object between the first point of time T1 and the second point of time T2 that accurately reflects a motion of the object, for example, the graph 1170, may be obtained. Also, a state of the object at each time point, for example, a point of time T12, a point of time T13, or a point of time T14, may be estimated by using the motion information. Referring to FIG. 13, it may be estimated that the object 1305 has a state 1321 at the point of time T12, a state 1322 at the point of time T13, and a state 1323 at the point of time T14.

FIG. 14 is a view for explaining an operation of reconstructing a target image according to another embodiment.

In FIG. 14, a target image is reconstructed by using a predetermined point of time included in a section from t=0 to t=end corresponding to an angle section from 0° to 225° in a 360°-section that is a full section as a target point of time T_target. Also, the target point of time T_target is an intermediate point of time in the section from t=0 to t=end. Also, motion information 1480 of FIG. 14 may correspond to that of a section from t=0 to t=end in a full 360°-section of the graph 1015 that is motion information of FIG. 10.

The tomography imaging apparatus 500 may reconstruct a target image at a target point of time Ttarget by using, for example, an MVF according to motion information indicating a motion of an object.

A motion amount of the object at the target point of time Ttarget may be estimated by using the motion information 1480. Alternatively, a state including at least one of a size, a shape, and a position of the object at the target point of time Ttarget may be estimated by using the motion information 1480.

As described with reference to FIG. 13, pieces of projection data obtained in each view or each predetermined angle section included in one cycle angle section are used to obtain images of different surfaces or different regions of the object.

The tomography imaging apparatus 500 may perform motion correction by using motion information on regions of the object or surfaces of the object to be imaged by using pieces of projection data obtained in points of time other than the target point of time Ttarget, other than a surface of the object or a region of the object to be imaged by using projection data obtained at the target point of time Ttarget.

Also, in FIG. 14, a target image 1470 is reconstructed by using tomography data obtained in an angle section corresponding to a section from t=0 to t=end corresponding to a 180+a°-angle section by using a half reconstruction method. Also, hereinafter, the 180+a°-angle section that is a data section needed to reconstruct the target image 1470 that is one tomography image is referred to as 'one cycle angle section'.

In FIG. 14, for convenience of explanation, one cycle angle section is divided into five angle sections, and images obtained by performing back projection on pieces of projection data obtained in the five angle sections are shown. In detail, a partial image 1421 is obtained by performing back projection on pieces of projection data obtained in a first angle section 1401. A partial image 1431 is obtained by performing back projection on pieces of projection data obtained in a third angle section 1402. A partial image 1441 is obtained by performing back projection on pieces of projection data obtained in a fourth angle section 1403. A partial image 1451 is obtained by performing back projection on pieces of projection data obtained in a fifth angle section 1404. A partial image 1461 is obtained by performing back projection on pieces of projection data obtained in a second angle section 1405.

In FIG. 14, the first angle section 1401, the second angle section 1405, the partial image 1421, and the partial image 1461 may respectively correspond to the first angle section 911, the second angle section 912, the first partial image 932, and the second partial image 942 of FIG. 9A.

Referring to FIG. 14, a target point of time Ttarget is set to an intermediate point of time in a section from a point of time t=0 to a point of time t=end. Only surfaces 1442, 1443, 1444, and 1445 arranged in a lateral direction as shown in the partial image 1441 are imaged when projection data obtained in an angle section adjacent to the target point of time Ttarget is back-projected. Surfaces not shown in the partial image 1441 are imaged by using pieces of projection data obtained in angle sections other than the fourth angle section 1403 that includes the target point of time Ttarget in one cycle angle section.

The tomography imaging apparatus 500 may perform motion correction in order to minimize blur by using the motion information 1480 when imaging surfaces not shown in the partial image 1441.

In detail, surfaces or partial regions shown in the partial image 1421 obtained in the first angle section 1401 are corrected according to the motion information 1480. That is, in the motion information 1480, it is assumed that a motion amount W in the first angle section 1401 is 0 and a motion amount W1 of an object at the target point of time Ttarget 1481 is 0.5. A surface of the object at the target point of time Ttarget may be accurately obtained by warping the object included in the partial image 1421 corresponding to the first angle section 1401 by the motion amount W of 0.5. Accordingly, a corrected partial image 1422 is generated by performing motion correction on the partial image 1421 based on a motion amount 1424 which occurs from the start point of time t=0 to the target point of time Ttarget, with respect to a full motion amount 1423. The full motion amount 1423 may correspond to the motion amount W of 1 which occurs between t=0 and t=end in the motion information 1480, and the motion amount 1424 may correspond to a 'difference between the motion amount W at the start point of time t=0 corresponding to the first angle section 1401 and the motion amount W1 at the target point of time Ttarget'.

Motion correction is performed in other angle sections in the same manner as that performed in the first angle section 1401. In detail, a corrected partial image 1422 is generated by performing motion correction on the partial image 1431 obtained by performing back projection on pieces of projection data obtained in the third angle section 1402 based on a motion amount 1434 which occurs from a third point of time T12 to the target point of time Ttarget, with respect to the full motion amount 1423.

Also, a corrected partial image 1462 is generated by performing motion correction on the partial image 1461 obtained by performing back projection on pieces of projection data obtained in the second angle section 1405 based on a motion amount 1464 which occurs from the end point of time t=end to the target point of time Ttarget, with respect to the full motion amount 1423. Also, a corrected partial image 1452 is generated by performing motion correction on the partial image 1451 obtained by performing back projection on pieces of projection data obtained in the fifth angle section 1404 based on a motion amount 1454 which occurs from the fifth point of time T14 to the target point of time Ttarget, with respect to the full motion amount 1423.

Motion correction using pieces of projection data obtained at a point of time before the target point of time Ttarget and motion correction using pieces of projection data obtained at a point of time after the target point of time Ttarget may be performed in opposite directions. In detail, in the motion information 1480, motion correction is performed in a direction in which the motion amount W increases at a point of time before the target point of time Ttarget and motion correction is performed in a direction in which the motion amount W decreases at a point of time after the target point of time Ttarget. Accordingly, the full motion amount 1423 at a first point of time T1 and the full motion amount 1423 at a second point of time T2 are shown in opposite directions.

A target image corresponding to the target point of time Ttarget may be reconstructed by using the partial image 1441 obtained in the fourth angle section 1403 including the target point of time Ttarget and the corrected partial images 1422, 1432, 1452, and 1462. Since the corrected partial images 1422, 1432, 1452, and 1462 accurately reflect a motion state of the object at the target point of time Ttarget, the target image reconstructed after being motion-corrected by using the motion information may be generated to have minimized motion artifacts.

In FIG. 14, an operation of correcting a partial image may be referred to as warping. In detail, a state including at least one of a size, a shape, and/or a position of an object at a target point of time may be estimated by using motion information. A target image may be generated by warping the object based on an estimated state change amount. In detail, an operation of warping an object refers to an operation of estimating a state of an object (for example, at least one of a size, a shape, and a position) at a target point of time by using motion information and reconstructing a target image by correcting a motion of the object according to the estimated state. A warping operation will now be explained in detail with reference to FIGS. 15 through 17.

FIG. 15 is a view for explaining a warping operation used to reconstruct a target image according to an embodiment.

The tomography imaging apparatus 500 performs back projection by projecting filtered projection data obtained in a plurality of views included in one cycle angle section onto an image domain 1501 indicating an object in order to reconstruct a target image. The following will be explained on the assumption that back projection is performed on a region 1502 included in the image domain 1501. The 'region 1502' may be image data including pixel values as shown in FIG. 15, or may be an image itself that is obtained by using pixel values. Also, the 'region 1502' may be an image space itself for obtaining an image of an object. Although the region 1502 is a 2D region in FIG. 15, the region 1502 may be a 3D region.

In FIG. 15, filtered projection data 1510 obtained by projecting X-rays in a direction 1511 at a first point of time T1 (the point of time T1 of FIG. 14) in one cycle angle section is back-projected. Pieces of image data included in the region 1502 may be referred to as 'back-projected projection data'.

Referring to FIG. 15, the tomography imaging apparatus 500 may warp an image grid including a plurality of pixels for imaging an object based on motion information according to a motion amount of the object at a target point of time Ttarget and may reconstruct a target image by using the warped image grid.

In detail, referring to FIG. 15, the filtered projection data 1510 is projected onto an image grid included in the region 1502. The projecting of the filtered projection data 1510 onto the image grid that is an image space is referred to as 'back projection'.

Accordingly, pixel values 1513 are filled in the region 1502 as shown in FIG. 15. When an object does not move, even when an image is obtained by cumulatively projecting the filtered projection data 1510 according to views onto the image grid, motion artifacts may not occur on a reconstructed target image. However, when the object moves for one cycle angle section, there occurs a difference between surfaces indicating the same body part of the object in a plurality of pieces of filtered projection data obtained in a plurality of views. Accordingly, when an image is obtained by cumulatively projecting the filtered projection data 1510 according to views onto the image grid, motion artifacts occur on a reconstructed target image.

In order to minimize motion artifacts of a moving object in an embodiment, motion correction is performed as described with reference to FIG. 14. Warping of an image grid for motion correction will now be explained in detail.

Motion information may be represented as an MVF in a full angle section or the graph 1015 obtained according to MVF information. In FIG. 15, motion information used for motion correction is represented as an MVF indicating a motion of an object.

Also, motion correction of back-projected projection data obtained at the first point of time T1 may be performed based on an MVF 1520 corresponding to the motion amount 1424 used for motion correction of the partial image 1421 of the object at the first point of time T1 of FIG. 14.

The tomography imaging apparatus 500 warps the image grid 1530 for imaging the same body part as the region 1502 by using motion information indicating a motion of the object according to an MVF indicating a motion amount of the object which occurs from the first point of time T1 to a target point of time. For example, a left upper region in the image grid 1530 may be warped according to a vector 1381.

Accordingly, an image grid 1540 obtained by warping the image grid 1530 is generated. The tomography imaging apparatus 500 projects pixel values included in the filtered projection data 1510 onto the warped image grid 1540. Accordingly, pixel values are included in a region 1535 corresponding to the region 1502 as shown in FIG. 15. In the region 1535, a quadratic image grid 1541 marked by a dashed line is a general image grid that is not warped.

Continuously, the tomography imaging apparatus 500 re-samples the region 1535 including pixel values according to the warped image grid 1540 into a region 1545 including pixel values according to the quadratic image grid 1541. In detail, the tomography imaging apparatus 500 converts pixel values according to the warped image grid 1540 into pixel values according to Cartesian coordinates by performing interpolation using a quadratic image pixel matrix.

An operation of re-sampling pixel values of pixels 1542 and 1543 included in the warped image grid 1540 into a pixel value of a pixel 1554 included in the quadratic image grid 1541 will now be explained. Also, the pixels 1542 and 1543 included in the warped image grid 1540 are enlarged in a block 1547.

The pixel 1542 in the warped image grid 1540 has a signal value of '2' and the pixel 1543 in the warped image grid 1540 has a signal value of '1'. That is, since an image signal value included in the entire pixel 1542 is 2, a signal value '2' is distributed and included in the pixel 1542 according to an area ratio. Accordingly, a signal value of 1 may be included in a partial region 1561 that corresponds to a half of an entire area of the pixel 1542. Since an image signal value included in the entire pixel 1543 is 1, a signal value of 1 is distributed and included in the pixel 1543 according to an area ratio. Accordingly, a signal value of 0.5 may be included in a partial region 1562 that corresponds to a half of an entire area of the pixel 1543. Also, a signal value of 1.5 obtained by summing the signal value of 1 of the partial region 1561 and the signal value of 0.5 of the partial region 1562 may be included in a pixel 1554, according to quadratic image grids 1541 and 2251, including the partial region 1561 and the partial region 1562.

Accordingly, pixel values of a re-sampled region 1545 are arranged according to a quadratic image grid 1551. Accordingly, pixel values of pixels 1555 included in the re-sampled region 1545 may be generated by re-sampling all pixel values included in the region 1535.

Also, any of various other methods may be used to convert pixel values arranged according to a warped image grid into pixel values arranged according to a quadratic image grid.

Also, motion correction may be performed by using warping on each of all pieces of back-projected projection data corresponding to a plurality of views included in one cycle angle section. A target image may be reconstructed by cumulating the plurality of pieces of back-projected projection data that are motion-corrected.

However, motion correction using warping of an image grid may not be performed in each view. For example, motion correction may be performed in every predetermined angle section, or a plurality of views may be grouped and motion correction may be performed in every plurality of views included in one group.

As described above, the tomography imaging apparatus 500 may generate motion-corrected image data 1570 by using a warped image grid based on motion information. A motion-corrected target image may be reconstructed by using, for example, the motion-corrected image data 1570 corresponding to each view.

FIG. 16 is a view for explaining a warping operation used to reconstruct a target image according to another embodiment. In FIG. 16, a repeated explanation of the same elements and operations as those in FIG. 15 will not be given.

In detail, the tomography imaging apparatus 500 may generate a motion-corrected target image by warping a back-projected image according to motion information. In detail, the tomography imaging apparatus 500 may reconstruct a target image by warping a pixel corresponding to data obtained by using tomography imaging based motion information, during a back projection process. In detail, the tomography imaging apparatus 500 may warp a pixel according to a motion amount of an object at a target point of time Ttarget according to an MVF.

Referring to FIG. 16, pixels of an image (or image data) 1630 generated by back-projecting the filtered projection data 1510 are warped based on an MVF 1381. Accordingly, pixel values of pixels 1631 included in the image 1630 are generated as an image 1635 that is warped to correspond to a motion of an object at a target point of time Ttarget based on an MVF. In detail, filtered projection data 1611 corresponds to pixel values 1636 of pixels in the warped image 1635 and filtered projection data 1612 corresponds to pixel values 1637 of pixels in the warped image 1635.

A motion-corrected image 1655 is generated by re-sampling the warped image 1635 in the same manner as that of FIG. 15. Pixel values of pixels 1656 included in the motion-corrected image 1655 accurately reflect the motion of the object at the target point of time Ttarget. Accordingly, motion artifacts in a target image that is finally reconstructed may be minimized.

FIG. 17 is a view for explaining an operation of reconstructing a target image according to another embodiment. In FIG. 17, a repeated explanation of the same elements and operations as those in FIGS. 15 and 16 will not be given. The tomography imaging apparatus 500 may perform motion correction during a back projection process based on motion information. In detail, the tomography imaging apparatus 500 may warp a center of a voxel indicating an object based on motion information, may perform back projection based on a position of the warped voxel, and may reconstruct a target image. The voxel refers to one unit space in a virtual 3D grid space for imaging the object. In FIG. 17, a virtual space for imaging the object includes pixels that constitute a 2D grid space, instead of voxels that constitute a 3D grid space.

In detail, the tomography imaging apparatus 500 may determine which pixel value in a detector array has to be referred to when a pixel value of a predetermined position in an image to be reconstructed is affected by a motion at each point of time, by using an MVF from a target point of time Ttarget to each point of time. Regarding a voxel indicating an object at the target point of time, in order to back-project projection data filtered in a view of a point of time other than the target point of time to the voxel, a motion of the object has to be reflected and a position to which the voxel is to move to at the point of time has to be calculated. A movement amount of the voxel for compensating for the motion of the object may be calculated by using an inverse MVF of an MVF from the point of time to the target point of time. A position of the voxel may be moved by the calculated movement amount, and then which pixel value in the detector array has to be taken may be calculated.

In detail, referring to FIG. 17, the tomography imaging apparatus 500 generates an inverse MVF 1710 by inverting the MVF 1520 indicating a motion amount of an object at a target point of time Ttarget. A position of each pixel in a back-projected image 1720 is changed by using the inverse MVF 1710.

For example, positions of pixels in the back-projected image 1720 are changed based on motion vectors 1711, 2421, 2422, and 2423 included in the inverse MVF 1710. In detail, a pixel 1731 that is first from right in an uppermost row is moved based on a vector 1721 and a vector 1722. A pixel 1732 that is first from right in a fifth row in the back-projected image 1720 is moved based on a motion vector 1723. Also, a position of a pixel of a region 1727 whose motion is not detected in the inverse MVF 1710 is maintained.

Continuously, in consideration of a changed position of a pixel, the tomography imaging apparatus 500 calculates to which position of a detector array a pixel value of a pixel is projected, takes the projection data 1510 filtered at the calculated position, cumulates the projection data 1510 on the pixel (voxel), and obtains the back-projected image 1720.

For example, when a changed position of the pixel 1731 is considered, a center of a pixel 1751 that is first from right in an uppermost row in a back-projected image 1750 is obtained by using a pixel value at a point P1 of the filtered projection data 1510. Since the point P1 is not located at a center of a pixel 1756, first from right in an uppermost row, of the filtered projection data 1510 but is located close to a pixel 1755 that is second from right in the uppermost row, the point P1 is affected by the pixel 1756 and the pixel 1755. Accordingly, the pixel 1751 may have a pixel value of '0.2' as shown in FIG. 17 based on a pixel value of '0' of the pixel 1756 and a pixel value of '1' of the pixel 1755.

Also, similarly, when a changed position of the pixel 1732 is considered, a center of a pixel 1752 that is first from right in a fifth row in the back-projected image 1750 is located between surfaces of the pixel 1752 and an adjacent pixel 1757. Accordingly, the center of the pixel 1752 is affected at the same ratio from the pixel 1756 and the pixel 1755. Accordingly, the pixel 1752 may have a pixel value of '0.5' that is an intermediate value between a pixel value of '0' of the pixel 1756 and a pixel value of '1' of the pixel 1755.

As described above, the tomography imaging apparatus 500 may obtain a back-projected image that is motion-corrected by warping a voxel by using an inverse MVF, without using warping of FIGS. 15 and 16. The tomography imaging apparatus 500 may obtain a motion-corrected target image 1770 based on the back-projected image that is motion-corrected according to each view.

As described above, in an embodiment, when a full angle section, for example, a 360°-angle section, is divided into a plurality of partial angle pairs and a motion of an object at a time point is estimated based on a partial image pair corresponding to each of the partial angle pairs, the motion of the object is estimated by using a plurality of the partial image pairs with a high time resolution, thereby making it possible to accurately measure the motion of the object which occurs for a full section. Accordingly, motion information accurately indicating the motion of the object in the full section may be obtained, and thus the motion of the object at each point of time included in the full section may be more accurately measured. Motion artifacts may be reduced by performing motion correction based on a motion state of the object that is accurately measured. Accordingly, a target image with high quality may be reconstructed.

Also, the tomography imaging apparatus 500 may operate as follows, which will be explained with reference to FIGS. 18A and 18B.

FIGS. 18A and 18B are views illustrating a plurality of models used in the tomography imaging apparatus 500 according to an embodiment.

The data obtainer 510 may obtain a first partial image and a second partial image respectively corresponding to a first point of time and a second point of time by using pieces of data obtained in a first angle section and a second angle section that face each other by performing tomography imaging on a moving object.

The first partial image and the second partial image respectively correspond to the first partial image 932 and the second partial image 942 of FIG. 9A, and thus a detailed explanation thereof will not be given.

The image processor 520 measures a motion amount of the object for the first point of time and the second point of time by using the first partial image and the second partial image. An operation of measuring a motion amount of the object by using the first partial image and the second partial image is the same as that of FIGS. 11A and 11B, and thus a detailed explanation thereof will not be given. A target image indicating the object at a target point of time between the first point of time and the second point of time is reconstructed based on a plurality of models indicating a motion of the object between the first point of time and the second point of time set based on the measured motion amount.

Each of the plurality of models that is information indicating a motion of the object for a time section between the first point of time and the second point of time that are predetermined times may correspond to the graph 1170 that is information indicating a motion of the object of FIG. 11C. In detail, each of the plurality of models is a motion model of the object indicating a motion amount of the object according to a time, and may be represented as a graph (e.g., the graph 1170 of FIG. 11C) including a weight value corresponding to a motion amount according to a time.

However, the plurality of models may have different shapes. In detail, although the graph 1170 of FIG. 11C has a linear shape, graphs of the plurality of models may have various shapes.

In detail, the plurality of models may include at least one model indicating a motion shape of the object that moves at a non-constant velocity for the first point of time and the second point of time.

In detail, the plurality of models may have the same motion amount between the first point of time and the second point of time and may have different motion shapes of the object for a time between the first point of time and the second point of time. A motion amount between the first point of time and the second point of time in all of the plurality of models varies according to an MVF between the first partial image and the second partial image.

Referring to FIG. 18A, graphs of a plurality of models may have shapes shown in FIG. 18A.

Referring to FIG. 18A, a graph 1811 that has a linear shape, like the graph 1170 of FIG. 11C, is a model indicating a motion shape of an object that moves at a constant velocity. Graphs other than the graph 1811, for example, a graph 1810 is a motion model indicating that a motion velocity of the object is changed at a point of time corresponding to an angle point of 90° and a state of the object is changed before the angle point of 90° and is not changed after the angle point of 90°.

Also, referring to FIG. 18B, graphs of a plurality of models may have shapes as shown in FIG. 18B.

Referring to FIG. 18B, the graphs of the plurality of models show different motion shapes, and may include a graph 1850 indicating that a velocity of a motion is changed at an angle point of 45°, a graph 1851 indicating that a velocity of a motion is changed at angle points of 45° and 90°, and a graph 1852 indicating that a velocity of a motion is changed at an angle point of 135°.

In FIGS. 18A and 18B, for convenience of explanation, a plurality of models represent a motion amount for a 180°-angle section. However, when a tomography image is reconstructed by using a half reconstruction method, a plurality of models may represent a motion amount of an object for a 180+a°-angle section, and when a tomography image is reconstructed by using a full reconstruction method, a plurality of models may represent a motion amount of an object for a 360+a°-angle section.

Also, shapes of a plurality of models may be set based on a motion shape of an object to be tomography-imaged. For example, when the heart is to be tomography-imaged, shapes of a plurality of models may be set so that a plurality of motion shapes of the heart having a high frequency of occurrence are reflected.

Alternatively, shapes of a plurality of models may be set by a user. For example, the user may set shapes of a plurality of models through the user interface 550.

The controller 530 measures image quality of a plurality of target images that are reconstructed based on a plurality of models, and selects one from among the plurality of models based on the measured image quality. The controller 530 controls a final target image indicating the objet at a target point of time to be reconstructed based on the selected model.

In detail, the controller 530 may reconstruct a target image by performing image correction based on each of a plurality of models. Since a model corresponds to motion information and motion correction based on the motion information has been explained with reference to FIGS. 12 through 17, and thus a detailed explanation of motion correction based on a model will not be given.

Since the controller 530 reconstructs a target image by using each of a plurality of models, the tomography imaging apparatus 500 may obtain a plurality of target images respectively corresponding to the plurality of models. The controller 530 may select a model corresponding to a first target image with highest image quality from among the plurality of target images. The controller 530 may control a final target image that is motion-corrected to be reconstructed based on the selected model.

Image quality may be measured by using an image quality metric for measuring at least one from among an image blur amount and an image resolution. The image quality metric that is a quantitative standard for determining image quality may use a physical or psychological parameter.

For example, the image quality metric may use a physical parameter such as a modulation transfer function (MTF) or a psychological parameter such as a user's contrast sensitivity function (CSF).

Alternatively, image quality may be measured by using a histogram-based image blur metric. A histogram of a region to be measured by using a metric may be obtained and an image blur amount of the region may be measured by calculating an entropy by using the histogram.

The image quality metric is explained in detail in the thesis of C. Rohkohl, H. Bruder, K, Stierstorfer, and T. Flohr (Improving best-phase image quality in cardiac CT by motion correction with MAM optimization, Med. Phys., vol. 40, no. 3, 2013).

Image quality may be determined by combining standards for quality evaluation that are various parameters.

In detail, the controller 530 may measure image quality of each of a plurality of target images corresponding to a plurality of models according to an image quality metric and may select a model corresponding to a target image with highest image quality from among the measured image quality.

As described above, a target image with high quality may be finally obtained by selecting one from among a plurality of models based on image quality of a reconstructed image and performing motion correction by using the selected model.

Also, the tomography imaging apparatus 500 may operate as follows, which will be explained in detail with reference to FIGS. 19 through 26.

The data obtainer 410 may obtain a first image corresponding to a first point of time and a second image corresponding to a second point of time by performing tomography imaging on an object. An operation of obtaining the first image and the second image will be explained below in detail with reference to FIGS. 19 through 20.

The controller 430 may divide each of the first image and the second image into a plurality of regions, and may obtain a partial motion model indicating a motion of the object between the first point of time and the second point of time by using the first image and the second image in each of the plurality of regions. The controller 430 may obtain a full motion model indicating a motion of the object in a full region including the plurality of regions based on a plurality of the partial motion models respectively corresponding to the plurality of regions.

The image processor 420 may reconstruct a target image indicating the object at a target point of time between the first point of time and the second point of time based on the full motion model. Motion correction based on the full motion model that is motion information of the object is the same as that described with reference to FIGS. 12 through 17, and thus a detailed explanation thereof will not be given.

FIG. 19 is a view for explaining an operation of the tomography imaging apparatus 500 according to another embodiment.

The data obtainer 510 obtains a first image corresponding to a first point of time and obtains a second image corresponding to a second point of time. In detail, the first image and the second image are images obtained by performing tomography imaging on the same object at different points of time. Although the first image and the second image are obtained by the data obtainer 510 in an embodiment, the data obtainer 510 may obtain only tomography data needed to reconstruct the first image and the second image, and the image processor 520 may reconstruct the first image and the second image based on the obtained tomography data.

The following will be explained on the assumption that a sinogram including a plurality of pieces of projection data is raw data and a first image and a second image are 3D tomography images. Also, the first image and the second image are complete images reconstructed by using a half reconstruction method or a full reconstruction method.

In detail, when a user is to reconstruct a tomography image of an object at a point of time included in a predetermined time section, a first point of time may correspond to a lower limit value in the predetermined time section and a second point of time may correspond to an upper limit value of the predetermined time section. For example, when the user is to reconstruct a tomography image of the heart at one point of time included in a time section from t1 to t2, the first point of time may be t1 and the second point of time may be t2. Also, the time section between t1 and t2 is a full time section and the full time section indicates P1, P2, or P3. For example, a time section between t1 and t2 may be a cardiac cycle.

Referring to FIG. 19, the data obtainer 510 may obtain a sinogram 1921 in a first time section P11 corresponding to the first point of time t1, and may obtain a sinogram 1922 in a second time section P12 corresponding to the second point of time t2. A first image 1950 may be reconstructed by using the sinogram 1921 and a second image 1960 may be reconstructed by using the sinogram 1922. For example, the first point of time t1 may be an intermediate point of the first time section P11 and the second point of time t2 may be an intermediate point of the second time section P12.

In FIG. 19, a tomography image is reconstructed by using filtered back projection.

In detail, the data obtainer 510 gates a plurality of first time sections P11, P21, and P31 for generating the first image 1950 in a plurality of cycles of an ECG signal. The data obtainer 510 obtains sinograms 1921, 1931, and 1941 in the first time sections P11, P21, and P31. The data obtainer 510 gates a plurality of second time sections P12, P22, and P32 for generating the second image 1960 in a plurality of cycles of an ECG signal. The data obtainer 510 obtains sinograms 1922, 1932, and 1942 in the second time sections P12, P22, and P32. The data obtainer 510 may reconstruct the first image 1950 by back-projecting the sinograms 1921, 1931, and 1941 and may reconstruct the second image 1960 by back-projecting the sinograms 1922, 1932, and 1942.

Although sinograms obtained in a plurality of time sections are used in order to reconstruct the first image 1950 and the second image 1960 in FIG. 19, the first image 1950 and the second image 1960 may be images reconstructed by using sinograms obtained in one time section.

An operation of reconstructing the first image 1950 and the second image 1960 by using ECG gating will now be explained in detail with reference to FIGS. 20A and 20B.

FIGS. 20A and 20B are views for explaining an operation of obtaining a first image and a second image used to measure a motion of an object.

FIGS. 20A and 20B are views for explaining an operation of reconstructing a first image and a second image. In detail, FIG. 20A is a view for explaining an operation of generating a first image 2020. FIG. 20B is a view for explaining an operation of generating a second image 2050. In FIGS. 20A and 20B, the first image 2020 and the second image 2050 respectively correspond to the first image 1950 and the second image 1960 of FIG. 19.

In FIGS. 20A and 20B, the first image 2020 and the second image 2050 are 3D tomography images that reveal the heart with a volume. Also, reconstructed 3D tomography images may be reconstructed to indicate various views such as a sagittal view, a coronal view, and a transaxial view. Alternatively, a first image and a second image reconstructed by the tomography imaging apparatus 500 may be 2D tomography images.

Referring to FIG. 20A, the data obtainer 510 extracts a plurality of time sections P11, P21, P31, P41, and P51 in which a motion of the heart is minimized by gating an ECG signal 2000. The data obtainer 510 reconstructs a plurality of partial images, for example, first through fifth partial images 2021, 2022, 2023, 2024, and 2025, by using sinograms obtained in the extracted plurality of time sections P11, P21, P31, P41, and P51. In FIG. 20A, the time sections P11, P21, and P31 respectively correspond to the time sections P11, P21, and P31 of FIG. 19.

In detail, the data obtainer 510 reconstructs the first image section 2021 by using a sinogram obtained in the time section P11, reconstructs the second image section 2022 by using a sinogram obtained in the time section P21, and reconstructs the third image section 2023 by using a sinogram obtained in the time section P31. The data obtainer 510 reconstructs the fourth image section 2024 by using a sinogram obtained in the time section P41, and reconstructs the fifth image section 2025 by using a sinogram obtained in the time section P51.

The first image 2020 may be reconstructed by combining the reconstructed first through fifth image sections 2021, 2022, 2023, 2024, and 2025.

Referring to FIG. 20B, the data obtainer 510 extracts a plurality of time sections P12, P22, P32, P42, and P52 in which a motion of the heart is minimized by gating the ECG signal 2000. The data obtainer 510 reconstructs a plurality of partial images, for example, first through fifth partial images 2051, 2052, 2053, 2054, and 2055, by using sinograms obtained in the extracted plurality of time sections P12, P22, P32, P42, and P52. In FIG. 20B, the time sections P12, P22, and P32 respectively correspond to the time sections P12, P22, and P32 of FIG. 19.

In detail, the data obtainer 510 reconstructs the first image section 2051 by using a sinogram obtained in the time section P12, reconstructs the second image section 2052 by using a sinogram obtained in the time section P22, and reconstructs the third image section 2053 by using a sinogram obtained in the time section P32. The data obtainer 510 reconstructs the fourth image section 2054 by using a sinogram obtained in the time section P42 and reconstructs the fifth image section 2055 by using a sinogram obtained in the time section P52.

The second image 2050 may be reconstructed by combining the reconstructed first through fifth partial images 2051, 2052, 2053, 2054, and 2055.

A first image and a second image of FIGS. 19 through 20B that are tomography images reconstructed before motion correction may be referred to as 'initial images'.

The first image 2020 may be an image indicating an object at a first point of time t1 and reconstructed by using pieces of projection data obtained in a first time section. Also, the second image 2050 may be an image indicating the object at a second point of time t2 and reconstructed by using pieces of projection data obtained in a second time section.

The controller 530 divides each of the first image and the second image into a plurality of regions. An operation of dividing an image into a plurality of regions will now be explained in detail with reference to FIG. 21.

FIG. 21 is a view for explaining an operation of measuring a motion by using a first image and a second image according to an embodiment.

Referring to FIG. 21, a first image 2110 and a second image 2120 respectively correspond to the first image 1950 and the second image 1960 of FIG. 19. The controller 530 divides each of the first image 2110 and the second image 2120 into a plurality of regions as shown in FIG. 21. The number of divided regions may be determined in consideration of target image quality of a reconstructed tomography image and the performance of the tomography imaging apparatus 500. Alternatively, the number of the divided regions may be set by a user through the user interface 550.

The controller 530 obtains a partial motion model indicating a motion of an object according to each divided region of the first image 2110 and the second image 2120. In detail, the controller 530 may compare the first image 2110 with the second image 2120, may obtain a motion between the first image 2110 and the second image 2120, for example, an MVF, and then may obtain motion information according to each divided region.

The partial motion model is information indicating a motion of the object according to a time in each divided region, which will now be explained in detail with reference to FIGS. 22A through 22C.

FIGS. 22A through 22C are views for explaining an operation of measuring a motion by using a first image and a second image according to another embodiment.

In detail, FIG. 22A is a view for explaining an operation of comparing a first image 2210 with a second image 2220. FIG. 22B is a view illustrating a motion amount between the first image 23210 and the second image 2220. FIG. 22C is a view for explaining a partial motion model.

Hereinafter, a 'divided region in a first region (e.g., 2130 of FIG. 21)' is referred to as a 'first divided image' and a 'divided region in a second region (e.g., 2150 of FIG. 21)' is referred to as a 'second divided image'.

The first image 2210 may be an image indicating an object at a first point of time t1 and reconstructed by using pieces of projection data obtained in a first time section 2261. Also, the second image 2220 may be an image indicating the object at a second point of time t2 and reconstructed by using pieces of projection data obtained in a second time section 2262.

In FIG. 22A, the first image 2210 and the second image 2220 respectively correspond to the first image 2110 and the second image 2120 of FIG. 21.

The following will be explained on the assumption that the first image 2210 and the second image 2220 are 2D images and a surface of an object is shown as an edge in an image.

Referring to FIG. 22A, the first image 2210 and the second image 2220 are tomography images of a moving object. Also, in FIG. 22A, one or more objects 2211 and 2212 or 2221 and 2222 included in one image are shown as circular solid objects.

In detail, in order to compare a motion amount of an object, the objects 2211 and 2212 included in the first image 2210 are compared with the objects 2221 and 2222 included in the second image 2220. A motion amount of the object may be obtained according to a comparison result, as shown in a comparative image 2230.

An operation of obtaining a motion amount of an object by comparing two different images is the same as that described with reference to FIGS. 11A and 11B, and thus a detailed explanation thereof will not be given.

In FIG. 22C, partial motion information indicating a motion of an object according to a time in a divided partial region is represented as a graph 2270 by using the first image 2210 and the second image 2220. Also, in the graph 2270, a motion amount of the object for a time section 2260 has a value ranging from 0 to 1. Hereafter, a value of the Y-axis corresponding to a motion amount of an object in a partial motion model such as the graph 2270 of FIG. 22C is referred to as a 'weight value'. Also, a partial motion model that is information indicating a motion amount of an object of FIG. 22C corresponds to the graph of FIG. 11C, and thus a repeated explanation thereof will not be given.

A partial motion model indicating a motion amount of an object according to a time in the time section 2260 that is a full time section having the first time section 2261 as a start and the second time section 22621 as an end as shown in FIG. 22C may be obtained based on a motion amount of the object which occurs between a first point of time and a second point of time measured in FIG. 22B.

Also, as shown in FIG. 22C, a weight value and a time in a partial motion model may have a linear relationship.

Also, in a partial motion model, a shape of a graph indicating a relationship between a weight value and a time may correspond to a motion pattern of an object. For example, when the time section 2260 is relatively long, for example, when the time section 2260 has a value of 1 to 2 seconds, a relationship between a weight value and a time in a partial motion model may be determined by a quadratic relationship or a relationship that is modeled by statistical information.

For example, a motion pattern of an object may be statistically modeled. In detail, when the object is the heart, a motion of the heart may be statistically modeled and a shape of graph 2270 in a partial motion model may be set to correspond to the modeled motion of the heart.

Alternatively, a shape of a graph indicating a relationship between a weight value and a time in a partial motion model may be a preset shape. Alternatively, a shape of a graph indicating a relationship between a weight value and a time in a partial motion model may be set by a user through the user interface 650.

Also, a shape of the graph 2270 indicating a motion pattern of an object may vary according to a body part of the object. For example, when the object is the entire heart, a shape of a graph in a partial motion model may reflect a motion of a body part of the heart included in a corresponding region.

A partial motion model may be obtained for each of a plurality of divided regions. For example, when each of the first image 2110 and the second image 2120 of FIG. 21 are divided into 18 regions as shown in FIG. 21, 18 partial motion models corresponding to the 18 divided regions may be obtained.

A motion pattern of an object that is to be tomography-imaged may vary according to each of partial regions included in the object. In this case, a partial motion model of each partial region may be obtained to reflect different motion patterns according to the partial regions. Motion correction may be performed on a target image based on the partial motion models that are differently obtained according to the partial regions.

For example, when an object is the heart, motion patterns of a left ventricle, a right ventricle, a left atrium, and a right atrium may be different from one another. In this case, partial motion models of the left ventricle, the right ventricle, the left atrium, and the right atrium may be individually obtained, motion correction may be performed on partial images of the left ventricle, the right ventricle, the left atrium, and the right atrium, and a target image indicating the heart may be reconstructed by combining motion-corrected partial images.

In detail, the controller 530 may obtain a plurality of partial motion models respectively corresponding to a plurality of divided regions and may obtain a full motion model indicating a full motion of an object based on the partial motion models. In detail, the controller 530 may obtain the full motion model indicating a motion of each of a plurality of voxels included in a full region for a first point of time and a second point of time by interpolating at least two partial motion models from among the plurality of partial motion models.

A motion occurring in a partial region may affect other adjacent partial regions. Accordingly, when a full motion model is to be generated by combining partial motion models, the full motion model may be generated by interpolating a motion of one partial region and a motion of other partial regions.

For example, when a full motion model is to be generated by interpolating partial motion models, the controller 530 may set at least one control point on each partial region, and may interpolate a motion at one control point with a motion of at least one control point adjacent to the one control point.

Referring to FIG. 21, control points 2141, 2142, 2143, 2144, 2145, 2146, 2147, and 2148 are set in central pixels in divided regions. A full motion model may be obtained by interpolating a motion between the control pint 2141 located at a central portion of an image and a control point 2167 corresponding to the control point 2141 and a motion between the control points 2142, 2143, 2144, 2145, 2146, 2147, and 2148 included in divided regions adjacent to the control point 2141 and control points 2162, 2163, 2174, 2185, 2196, 2161, and 2168 included in divided regions adjacent to the control point 2167.

Also, a full motion model may include motion information of each of voxels included in a first image and a second image. That is, the full motion model may include information indicating a motion according to a time for each voxel.

Also, the controller 530 may obtain a full motion model by using a different method. In detail, the controller 530 may compare the first image 2110 with the second image 2120 and may obtain an MVF between the first image 2110 and the second image 2120. The MVF between the first image 2110 and the second image 2120 that is information indicating a motion of an object in a full time section including a first point of time and a second point of time may be a full motion model.

The full motion model indicating the MVF between the first image 2110 and the second image 2120 may be referred to as an 'initial motion model'. An initial motion model may be corrected based on a partial motion model indicating a motion of an object according to each divided region of FIGS. 22A through 22C. In detail, an initial motion model may be corrected based on a partial motion model to accurately reflect a motion in a divided region and the corrected initial motion model may be obtained as a full motion model.

Also, when an initial motion model or a partial motion model is to be obtained, a motion between the first image 2110 and the second image 2120 may be accurately measured when motion artifacts or blur of the first image 2110 and the second image 2120 are minimized. Accordingly, in order to reduce motion artifacts or blur of the first image 2110 and the second image 2120, a point of time at which a motion of an object is minimized may be selected as a first point of time and a second point of time. An operation performed by the tomography imaging apparatus 500 to select a first point of time and a second point of time will now be explained in detail with reference to FIGS. 23A through 24B.

FIGS. 23A through 23C are views for explaining an operation of setting points of time of a first image and a second image according to an embodiment.

The tomography imaging apparatus 500 may select two points of time at which a motion of an object in a predetermined time section are minimized as a first point of time t1 and a second point of time t2. The predetermined time section may be an R-R section that is a section between an R peak and another R peak of an ECG signal. The tomography imaging apparatus 500 may reconstruct an image at every second time interval (for example, a time interval between a point of time t11 and a point of time t12) in the predetermined time section, may measure a difference between an image that is reconstructed at one point of time and an image that is reconstructed at another point of time adjacent to the one point of time, and may select two points of time at which a motion of an object is minimized as a first point of time and a second point of time based on the measured difference.

Referring to FIG. 23A, the tomography imaging apparatus 500 reconstructs an image corresponding to a predetermined time interval in an ECG signal 2310. For example, the tomography imaging apparatus 500 reconstructs a tomography image 2321 by using a sinogram gated in a time section corresponding to the point of time t11 and reconstructs a tomography image 2322 by using a sinogram gated in a time section corresponding to the point of time t12. The tomography imaging apparatus 500 reconstructs a tomography image 2323 by using a sinogram gated in a time section corresponding to a point of time t(n−2) and reconstructs a tomography image 2324 by using a sinogram gated in a time section corresponding to a point of time t(n−1).

Referring to FIG. 23B, the tomography imaging apparatus 500 compares two images 2341 and 2342 corresponding to two adjacent points of time i and i+1 and generates a difference value 2343. The tomography imaging apparatus 500 generates a graph 2350 indicating the difference value 2343.

Referring to FIG. 23C, in the graph 2350, the x-axis represents a time and the y-axis represents the difference value 2343.

The tomography imaging apparatus 500 may obtain sections 2361 and 2362 in which a value of the y-axis in the graph 2350 is minimized, and may select points of time respectively corresponding to the sections 2361 and 2362 as the first point of time t1 and the second point of time t2. When a difference between two images corresponding to two adjacent points of time is the smallest, it means that a motion of an object between the two points of time is the smallest. Accordingly, a motion of an object is minimized in the section 2361 and the section 2362 in which a value of the y-axis is minimized. Accordingly, the tomography imaging apparatus 500 may obtain a section in which a motion of the heart is the most static and stable.

FIGS. 24A and 24B are views for explaining an operation of setting points of time of a first image and a second image according to another embodiment.

Referring to FIG. 24A, the tomography imaging apparatus 500 obtains projection data at every second time interval in a predetermined time section and measures a difference between projection data obtained in a time section corresponding to one point of time and projection data obtained at another point of time adjacent to the one point of time. The tomography imaging apparatus 500 may select two points of time at which a motion of an object is minimized as a first point of time and a second point of time.

Referring to FIG. 24A, a cardiac phase indicating one R—R cycle is set as 10% and when the cardiac phase is divided into 50, one interval is set as 2%.

The tomography imaging apparatus 500 obtains projection data at every time interval of 2% that is one interval. The tomography imaging apparatus 500 measures a difference value 2413 between a sinogram 2411 obtained by cumulating projection data obtained in a time section corresponding to one point of time and a sinogram 2412 obtained by cumulating projection data obtained in a time section corresponding to another point of time adjacent to the one point of time. For example, the sinogram 2411 may be a sinogram obtained for an interval of −2% to 0%, and the sinogram 2412 may be a sinogram obtained for an interval of 0% to 2%. A graph 2430 indicating the difference value 2413 is generated.

Referring to FIG. 24B, the x-axis of the graph 2430 represents a cardiac phase indicating an R—R cycle and the y-axis represents the difference value 2413.

The tomography imaging apparatus 50 may obtain points of time 2451 and 2452 at which a value of the y-axis that is a difference value in the graph 2430 is minimized and may select points of time corresponding to the points of time 2451 and 2452 as a first point of time t1 and a second point of time t2. Accordingly, the tomography imaging apparatus 500 may obtain a time section in which a motion of the heart is the most static and stable.

As shown in FIGS. 23A through 24B, the first point of time t1 and the second point of time t2 at which a motion of an object is minimized may be selected and a time section between the first point of time t1 and the second point of time t2 may be set as a full time section 2260.

Also, the tomography imaging apparatus 500 may correct a full motion model to increase an accuracy of the full motion model.

In detail, the controller 530 may estimate a target image corresponding to a target point of time based on a full motion model, may compare the estimated target image with a target image reconstructed by using data obtained by using tomography imaging, and may correct a full motion model based on a result of the comparison.

Referring to FIG. 22C, the tomography imaging apparatus 500 may compare data estimated by using a full motion model with actually measured data corresponding to a third point of time t3, at the third point of time t3 that is a point of time other than a first point of time t1 and a second point of time t2 in the full time section 2260, and may correct the full motion model to reduce a difference value. In detail, the tomography imaging apparatus 500 may move at every regular or irregular time interval in a time section between the first point of time t1 and the second point of time t2 and may perform motion correction on a full motion model at each point of time when the tomography imaging apparatus 500 moves.

In detail, the tomography imaging apparatus 500 may divide a time section between a first point of time t1 and a second point of time t2 into n parts, may move by a first time interval from at least one of the first point of time t1 and the second point of time t2, and may perform correction on a full motion model at each point of time when the tomography imaging apparatus 500 moves. In detail, the tomography imaging apparatus 500 may move by a first time interval from a first point of time t1 to a second point of time t2 and, when a point of time when the tomography imaging apparatus 500 moves is used as a third point of time t3, may perform correction on a full motion model at the third point of time t3. Alternatively, the tomography imaging apparatus 500 may move by a first time interval from a second point of time t2 to a first point of time t1, and when a point of time where the tomography imaging apparatus 500 moves is used as a third point of time t3, may perform correction on a full motion model at the third point of time t3.

For example, when a time section between a first point of time t1 and a second point of time t2 is divided into n parts, one time interval is (t2−t1)/n. Accordingly, correction may be performed on a full motion model at a point of time t1+(1/n)*(t2−t1) that is moved by one time interval from the first point of time t1, and correction may be performed again on the full motion model at a point of time t1+(2/n)*(t2−t1) that is moved by one time interval. As described above, an operation of correcting the full motion model in each of n time intervals included in a time section between the first point of time t1 and the second point of time t2 may be repeatedly performed.

Also, correction may be performed on a full motion model at a point of time t2−(1/n)*(t2−t1) that is moved by one time interval from the second point of time t2, and correction may be performed again on the full motion model at a point of time t2−(2/n)*(t2−t1) that is moved by one time interval. As described above, an operation of correcting the full motion model in each of n time intervals included in a time section between the first point of time t1 and the second point of time t2 may be repeatedly performed.

Also, the tomography imaging apparatus 500 may move by a first time interval from a first point of time t1 to a second point of time t2, and when a point of time when the tomography imaging apparatus 500 moves is used as a third point of time t3, may update a full motion model by correcting the full motion model at the third point of time t3. The tomography imaging apparatus 500 may move by a first time interval from the second point of time t2 to the first point of time t1, and when a point of time when the tomography imaging apparatus 500 moves is used as the third point of time t3, may update a full motion model by correcting the full motion model at the third point of time t3. The tomography imaging apparatus 500 may generate a final full motion model based on the two updated full motion models. In detail, the tomography imaging apparatus 500 may generate a final full motion model by averaging the two updated full motion models.

An operation of correcting a full motion model at a third point of time t3 in a time section between a first point of time t1 and a second point of time t2 will now be explained.

FIG. 25 is a view for explaining an operation of correcting a full motion model according to an embodiment.

Referring to FIG. 25, a graph 2510 indicates a full motion model before correction and a graph 2520 indicates a full motion model after correction. Also, a sinogram 2530 is obtained according to a time to correspond to a full time section P. The sinogram 2530 is a sinogram obtained by performing tomography imaging for the full time section P. That is, the sinogram 2530 that indicates data obtained by converting X-rays detected during tomography imaging is a measured data value. The sinogram 2530 may be obtained by performing tomography imaging in a retrospective mode or a prospective mode for the full time section P. Also, in each mode, the sinogram 2530 may be obtained by performing tomography imaging according to a spiral scan method or an axial scan method.

Also, a sinogram needed to reconstruct an image corresponding to a third point of time t3 may be a sinogram 2532 obtained for a time section corresponding to the third point of time t3. For example, when projection data is obtained by using a rebeamed parallel beam, in order to reconstruct an image corresponding to the third point of time t3, a sinogram obtained for a time section P3 corresponding to an angle section corresponding to an angle of 180+a° including the third point of time t3 is needed. Also, when a sinogram is obtained in a multi-detector system including a plurality of the X-ray generators 106, a plurality of sinograms respectively corresponding to the plurality of X-ray generators may be obtained for a time section corresponding to the third point of time t3.

The tomography imaging apparatus 500 may compare an estimated sinogram 2551 obtained by performing forward projection on an estimated third image 2550 obtained by using a full motion model with a measured sinogram 2561 obtained at the third point of time t3 and may correct the full motion model to reduce a difference between the estimated sinogram 2551 and the measured sinogram 2561. In detail, the tomography imaging apparatus 500 may correct the full motion model so that the estimated sinogram 2551 and the measured sinogram 2561 have the same value.

For example, when a difference between the measured sinograms 2532 and 2561 and the estimated sinogram 2551 decreases as a value of the y-axis in the full motion model before correction, which is indicated by the graph 2510, at the third point of time t3 increases, a weight value at the third point of time t3 in the full motion model may be increased from W1 to W1C.

Also, in the same manner, a weight value of the full motion model indicated by the graph 2510 may be corrected at a fourth point of time t4 that is moved by a predetermined time interval from the third point of time t3, and may be corrected at a fifth point of time t5 that is moved by a predetermined time interval from the fourth point of time t4.

As described above, when a measured sinogram and an estimated sinogram are compared with each other at a predetermined point of time and a full motion model is corrected based on a difference value calculated as a result of the comparison, the full motion model may be corrected in a full time section and a corrected full motion model indicated by the graph 2520 may be generated. The corrected full motion model indicated by the graph 2520 more accurately reflects a motion pattern of an object. Accordingly, when motion correction is performed to accurately reflect a state of the object at the third point of time t3 based on the corrected full motion model indicated by the graph 2520, an image corresponding to the third point of time t3 may be accurately reconstructed. In detail, when an image corresponding to the third point of time t3 is reconstructed by warping raw data obtained in order to reconstruct the image corresponding to the third point of time t3 or an image obtained by performing back projection on the obtained raw data based on the corrected full motion model indicated by the graph 2520, an image corresponding to a predetermined point of time may be easily and accurately reconstructed.

FIG. 26 is a view for explaining an operation of correcting a full motion model according to another embodiment.

Also, the tomography imaging apparatus 500 may compare a measured image generated by performing back projection on measured data obtained at a third point of time t3 with an estimated image and may correct a full motion model to reduce a difference between the estimated image and the measured image.

Referring to FIG. 26, a graph 2610 indicates a full motion model before correction and a graph 2620 indicates a full motion model after correction. Also, a sinogram 2630 is obtained in a full time section. The sinogram 2630 is a sinogram obtained by performing tomography imaging for a time corresponding to the full time section. That is, the sinogram 2630 is a data value measured by using tomography imaging. Also, a sinogram 2651 is a signogram needed to reconstruct an image corresponding to a third point of time t3.

Referring to FIG. 26, the tomography imaging apparatus 500 compares a measured image 2652 generated by back-projecting the sinogram 2651 obtained at a second point of time with an estimated image 2660 generated by warping at least one of a first image and a second image by using the full motion model before correction indicated by the graph 2610. The tomography imaging apparatus 500 may correct a full motion model to reduce a difference between the estimated image 2660 and the measured image 2652.

For example, when a difference between the measured image 2652 and the estimated image 2660 decreases as a value of the y-axis in the full motion model before correction, indicated by the graph 2610, at the third point of time t3 increases, a weight value at the third point of time t3 in the full motion model may be increased from W1 to W1C.

Also, in the same manner, a weight value of the full motion model indicated by the graph 2610 may be corrected at a fourth point of time t4 that is moved by a predetermined time interval from the third point of time t3 and may be corrected at a fifth point of time t5 that is moved by a predetermined time interval from the fourth point of time t4.

The third point of time t3 corresponding to a third image to be reconstructed by using a corrected full motion model may be a point of time that is moved by a predetermined interval from at least one of the first point of time t1 and the second point of time t2 as described with reference to FIGS. 16 and 17. Alternatively, the third point of time t3 may be set through the user interface 550. In detail, the display 580 may display a user interface screen (not shown) for selecting the third point of time t3 between the first point of time t1 and the second point of time t2. Accordingly, a user may select the third point of time t3 through the user interface 550.

As described above, the corrected full motion model indicated by the graph 2620 more accurately reflects a motion pattern of an object. Accordingly, like in FIG. 25, an image corresponding to the third point of time t3 may be accurately reconstructed by performing motion correction to accurately reflect a state of the object at the third point of time t3 based on the corrected full motion model indicated by the graph 2620.

FIG. 27 is a flowchart of a method 2700 of reconstructing a tomography image according to an embodiment. The method 2700 according to an embodiment includes the same operations as those of the tomography imaging apparatus 500 of FIGS. 1 through 17. Accordingly, when the method 2700 is described, a repeated explanation of the same elements and operations as those in FIGS. 1 through 17 will not be given.

Referring to FIG. 27, data obtained by performing tomography imaging on a moving object is divided into a plurality of data pairs corresponding to a plurality of facing partial angle pairs. In operation 2710, a partial image pair is reconstructed by using each of the plurality of data pairs. Operation 2710 is the same as that described with respect to FIGS. 7 and 8, and thus a repeated explanation thereof will not be given.

In operation 2720, motion information indicating a motion of an object in a full section including the plurality of facing partial angle pairs is obtained based on the plurality of partial image pairs corresponding to the plurality of data pairs. Operation 2720 may be performed by the controller 530. An operation of obtaining motion information is the same as that described in detail with reference to FIGS. 11A through 11C, and thus a repeated explanation thereof will not be given.

In operation 2730, a target image indicating the object at a target point of time is reconstructed based on the motion information. Operation 2730 may be performed by the image processor 520. An operation of reconstructing a target image by performing motion correction is the same as that described in detail with reference to FIGS. 12 through 17, and thus a repeated explanation thereof will not be given.

FIG. 28 is a flowchart of a method 2800 of reconstructing a tomography image according to another embodiment.

The method 2800 according to an embodiment includes the same operations as those of the tomography imaging apparatus 500 of FIGS. 18A and 18B. Accordingly, when the method 2800 is described, a repeated explanation of the same elements and operations as those in FIGS. 18A and 18B will not be given.

Referring to FIG. 28, in operation 2810, a first partial image and a second partial image respectively corresponding to a first point of time and a second point of time are obtained by using pieces of data obtained in a first angle section and a second angle section that face each other by performing tomography imaging on a moving object. Operation 2810 is the same as that described in detail with reference to FIGS. 7 and 8, and thus a repeated explanation thereof will not be given.

In operation 2820, a motion amount of an object between the first point of time and the second point of time is measured by using the first partial image and the second partial image. Operation 2820 may be performed by the controller 530 and is the same as that described in detail with reference to FIGS. 9A through 10, and thus a repeated explanation thereof will not be given.

In operation 2830, a target image indicating an object at a target point of time between the first point of time and the second point of time is reconstructed based on each of a plurality of models indicating the motion of the object between the first point of time and the second point of time set based on the motion amount. Operation 2830 may be performed by the image processor 820. Also, the plurality of models are the same as those described in detail with reference to FIGS. 18A and 18B, and thus a repeated explanation thereof will not be given.

In operation 2840, image quality of a plurality of the target images reconstructed based on the plurality of models is measured and one is elected from among the plurality of models based on the measured image quality. Operation 2840 may be performed by the controller 530.

In operation 2850, a final target image indicating the object at the target point of time is reconstructed based on the selected model. Operation 2850 may be performed by the image processor 520.

FIG. 29 is a flowchart of a method 2900 of reconstructing a tomography image according to another embodiment.

The method 2900 according to an embodiment includes the same operations as those of the tomography imaging apparatus 500 of FIGS. 19 through 26. Accordingly, when the method 2800 is described, a repeated explanation of the same elements and operations as those in FIGS. 19 through 26 will not be given.

Referring to FIG. 29, in operation 2910, a first image corresponding to a first point of time is obtained and a second image corresponding to a second point of time is obtained by performing tomography imaging on an object. Operation 2910 may be performed by the data obtainer 510 and is the same as that described in detail with reference to FIGS. 19 through 20B, and thus a repeated explanation thereof will not be given.

In operation 2920, each of the first image and the second image is divided into a plurality of regions and a partial motion model indicating a motion of the object between a first point of time and a second point of time in each of the plurality of regions is obtained by using the first image and the second image. Operation 2920 may be performed by the controller 530 and is the same as that described in detail with reference to FIGS. 21 through 22C, and thus a repeated explanation thereof will not be given.

In operation 2930, a full motion model indicating a motion of the object in a full section including the plurality of regions is obtained based on a plurality of the partial motion models respectively corresponding to the plurality of regions. Operation 2930 may be performed by the controller 530.

In operation 2940, a target image indicating the object at a target point of time between the first point of time and the second point of time is reconstructed based on the full motion model. Operation 2940 may be performed by the image processor 520.

As described above, a tomography imaging apparatus and a method of reconstructing a tomography image according to the one or more embodiments may increase an accuracy in measuring a motion of an object and may improve image quality of a reconstructed target image by performing motion correction.

The embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

more embodiments have been described with reference to the figures, it will be understood by those of ordinary skill in the art that various changes in form and details may be made therein without departing from the spirit and scope of the inventive concept as defined by the following claims. Accordingly, the above embodiments and all aspects thereof are examples only and are not limiting.

The invention claimed is:

1. A tomography imaging apparatus comprising:
   a data obtainer configured to obtain data by performing tomography imaging on a moving object;
   one or more processors configured to:
   divide the data into a plurality of data pairs corresponding to a plurality of facing partial angle pairs;
   reconstruct a partial image pair by using each of the plurality of data pairs;
   obtain motion information indicating a motion of the object in a full section including the plurality of facing partial angle pairs based on a plurality of the partial image pairs corresponding to the plurality of data pairs; and
   control a target image, indicating the object at a target point of time, to be reconstructed based on the motion information,
   wherein each of the plurality of facing partial angle pairs comprises a first angle section that is imaged at a first time, and a second angle section having a 180° angle difference between the first angle section that is imaged at a second time that is different than the first time.

2. The tomography imaging apparatus of claim 1, wherein the first angle section and the second angle section have a value less than 180°.

3. The tomography imaging apparatus of claim 2, wherein each of the plurality of partial image pairs comprises a first partial image reconstructed by using data obtained in the first angle section and a second partial image reconstructed by using data obtained in the second angle section.

4. The tomography imaging apparatus of claim 3, wherein the one or more processors are further configured to obtain the motion information indicating a motion of a surface of the object in the full section based on the plurality of partial image pairs.

5. The tomography imaging apparatus of claim 1, wherein the one or more processors are further configured to obtain the motion information indicating a motion of the object according to a time so that each of partial images included in the plurality of partial image pairs has a first shape at a first point of time included in the full section.

6. The tomography imaging apparatus of claim 1, wherein the one or more processors are further configured to reconstruct a three-dimensional (3D) partial image pair indicating the object in a 3D space.

7. The tomography imaging apparatus of claim 6, wherein the motion information is information indicating a motion of the object in the 3D space and a four-dimensional (4D) space including a time point.

8. The tomography imaging apparatus of claim 1, wherein the one or more processors are further configured to estimate a motion amount of the object at the target point of time based on the motion information and control the target image to be reconstructed based on the estimated motion amount.

9. The tomography imaging apparatus of claim 8, wherein the one or more processors are further configured to reconstruct the target image by warping a plurality of images according to views indicating parts of the object based on the motion information.

10. The tomography imaging apparatus of claim 1, wherein the full section has a value equal to or greater than 360°.

11. The tomography imaging apparatus of claim 1, wherein the data obtainer is further configured to obtain data of a full section having a value of at least 360°.

12. The tomography imaging apparatus of claim 1, wherein the one or more processors are further configured to divide the data of the full section into a plurality of data pairs, and the plurality of facing partial angle pairs collectively form the full section.

13. The tomography imaging apparatus of claim 1, wherein the full section includes four facing partial angle pairs each having a value of 45°.

14. A method of reconstructing a tomography image, the method comprising:
  dividing data obtained by performing tomography imaging on a moving object into a plurality of data pairs corresponding to a plurality of facing partial angle pairs and reconstructing a partial image pair by using each of the plurality of data pairs;
  obtaining motion information indicating a motion of the object in a full section comprising the plurality of facing partial angle pairs based on a plurality of the partial image pairs corresponding to the plurality of data pairs; and
  reconstructing a target image indicating the object at a target point of time based on the motion information,
  wherein each of the plurality of facing partial angle pairs comprises a first angle section that is imaged at a first time, and a second angle section having a 180° angle difference between the first angle section that is imaged at a second time that is different than the first time.

15. The method of claim 14, wherein the first angle section and the second angle section have a value less than 180°.

16. The method of claim 15, wherein each of the plurality of partial image pairs comprises a first partial image reconstructed by using data obtained in the first angle section and a second partial image reconstructed by using data obtained in the second angle section.

17. The method of claim 16, further comprising obtaining the motion information indicating a motion of a surface of the object in the full section based on the plurality of partial image pairs.

18. The method of claim 14, further comprising obtaining the motion information indicating a motion of the object according to a time so that each of partial images included in the plurality of partial image pairs has a first shape at a first point of time included in the full section.

19. The method of claim 14, further comprising, before the dividing of the data, obtaining the data of a full section having a value of at least 360° by performing tomography imaging on the moving object.

20. The method of claim 14, wherein the dividing of the data divides the data of the full section into a plurality of data pairs, and the plurality of facing partial angle pairs collectively form the full section.

* * * * *